(12) United States Patent
Wang et al.

(10) Patent No.: US 12,319,956 B2
(45) Date of Patent: Jun. 3, 2025

(54) METHODS AND SYSTEMS FOR TARGETED RNA CLEAVAGE AND TARGET RNA-PRIMED ROLLING CIRCLE AMPLIFICATION

(71) Applicant: 10x Genomics, Inc., Pleasanton, CA (US)

(72) Inventors: Su Wang, Berkeley, CA (US); Robert Henley, Castro Valley, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 18/789,541

(22) Filed: Jul. 30, 2024

(65) Prior Publication Data

US 2025/0043339 A1    Feb. 6, 2025

Related U.S. Application Data

(60) Provisional application No. 63/659,275, filed on Jun. 12, 2024, provisional application No. 63/516,786, filed on Jul. 31, 2023.

(51) Int. Cl.
*C12Q 1/6841* (2018.01)
*C12Q 1/6874* (2018.01)

(52) U.S. Cl.
CPC ......... *C12Q 1/6841* (2013.01); *C12Q 1/6874* (2013.01)

(58) Field of Classification Search
CPC .................................. C12Q 1/68; C07H 21/00
See application file for complete search history.

(56) References Cited

U.S. PATENT DOCUMENTS

| | | | |
|---|---|---|---|
| 5,635,352 A | 6/1997 | Urdea et al. | |
| 5,695,940 A | 12/1997 | Drmanac et al. | |
| 6,306,597 B1 | 10/2001 | Macevicz | |
| 6,534,266 B1 | 3/2003 | Singer | |
| 7,255,994 B2 | 8/2007 | Lao | |
| 7,345,159 B2 | 3/2008 | Ju et al. | |
| 7,473,767 B2 | 1/2009 | Dimitrov | |
| 7,534,991 B2 | 5/2009 | Miller et al. | |
| 7,544,794 B1 | 6/2009 | Benner | |
| 7,555,155 B2 | 6/2009 | Levenson et al. | |
| 7,566,537 B2 | 7/2009 | Balasubramanian et al. | |
| 7,655,898 B2 | 2/2010 | Miller | |
| 7,893,227 B2 | 2/2011 | Wu et al. | |
| 7,910,304 B2 | 3/2011 | Drmanac | |
| 7,941,279 B2 | 5/2011 | Hwang et al. | |
| 7,989,166 B2 | 8/2011 | Koch et al. | |
| 8,124,751 B2 | 2/2012 | Pierce et al. | |
| 8,199,999 B2 | 6/2012 | Hoyt et al. | |
| 8,268,554 B2 | 9/2012 | Schallmeiner | |
| 8,330,087 B2 | 12/2012 | Domenicali | |
| 8,415,102 B2 | 4/2013 | Geiss et al. | |
| 8,431,691 B2 | 4/2013 | McKernan et al. | |
| 8,460,865 B2 | 6/2013 | Chee et al. | |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,632,975 B2 | 1/2014 | Vander Horn et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,624,538 B2 | 4/2017 | Church et al. |
| 9,650,406 B2 | 5/2017 | Zhou et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,179,932 B2 | 1/2019 | Church et al. |
| 10,227,639 B2 | 3/2019 | Levner et al. |
| 10,246,700 B2 | 4/2019 | Dunaway et al. |

(Continued)

FOREIGN PATENT DOCUMENTS

| | | |
|---|---|---|
| EP | 4015647 | 6/2022 |
| WO | WO 2017/143155 | 8/2017 |

(Continued)

OTHER PUBLICATIONS

Hyjek et al., RNases H : Structure and mechanism. DNA Repair 84:(2019) 102672 (Year: 2019).*
Takahashi et al., RNase H-assisted RNA-primed rolling circle amplifcation for targeted RNA sequence detection. Scientific Reports 8:7770 (Year: 2018).*
Takahashi et al., RNase H-assisted RNA-primed rolling circle amplifcation for targeted RNA sequence detection. Scientific Reports 8:7770(Supplementary Information) (Year: 2018).*
Wang et al., Structure and mechanism of T4 Polynucleotide kinase :an RNA repair enzyme. The EMBO Journal 21(14) :3873-3880 (Year: 2002).*

(Continued)

*Primary Examiner* — Ethan C Whisenant
(74) *Attorney, Agent, or Firm* — Morrison & Foerster LLP

(57) ABSTRACT

The present disclosure relates in some aspects to methods, systems, and kits for analyzing a biological sample comprising generating a rolling circle amplification product (RCP) using a target ribonucleic acid (RNA) as a primer. In some aspects, RNase H and a nucleic acid oligonucleotide are used to generate a free 3' end of the target RNA to prime RCA.

27 Claims, 21 Drawing Sheets

(56) References Cited

U.S. PATENT DOCUMENTS

| | | |
|---|---|---|
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,174,281 B1 | 11/2021 | Graham et al. |
| 11,287,422 B2 | 3/2022 | Previte et al. |
| 11,434,525 B2 | 9/2022 | Glezer |
| 11,459,603 B2 | 10/2022 | Tyagi et al. |
| 11,499,185 B2 | 11/2022 | Vijayan et al. |
| 11,643,679 B2 | 5/2023 | Glezer et al. |
| 11,999,999 B2 | 6/2024 | Ju et al. |
| 2011/0223585 A1 | 9/2011 | Gullberg et al. |
| 2013/0288249 A1 | 10/2013 | Gullbert |
| 2013/0323729 A1 | 12/2013 | Landegren et al. |
| 2016/0108458 A1 | 4/2016 | Frei et al. |
| 2016/0305856 A1 | 10/2016 | Boyden et al. |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2021/0017587 A1 | 1/2021 | Cai et al. |
| 2021/0115504 A1 | 4/2021 | Cai et al. |
| 2021/0198727 A1* | 7/2021 | Kuhnemund ........ C12Q 1/6844 |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282306 A1 | 9/2022 | Bava et al. |
| 2022/0282316 A1 | 9/2022 | Bava |
| 2022/0282319 A1 | 9/2022 | Verheyen |
| 2022/0372570 A1 | 11/2022 | Costa |
| 2022/0380838 A1 | 12/2022 | Kuhnemund et al. |
| 2022/0403458 A1 | 12/2022 | Bava |
| 2023/0002808 A1 | 1/2023 | Mignardi |
| 2023/0012607 A1 | 1/2023 | Kuhnemund et al. |
| 2023/0013775 A1 | 1/2023 | Chen et al. |
| 2023/0015226 A1 | 1/2023 | Chen et al. |
| 2023/0026886 A1 | 1/2023 | Chen |
| 2023/0031305 A1 | 2/2023 | Neuta et al. |
| 2023/0031996 A1 | 2/2023 | Neuta et al. |
| 2023/0035685 A1 | 2/2023 | Neuta et al. |
| 2023/0037182 A1 | 2/2023 | Bava et al. |
| 2023/0039148 A1 | 2/2023 | Verheyen |
| 2023/0041485 A1 | 2/2023 | Neuta et al. |
| 2023/0044650 A1 | 2/2023 | Dockter |
| 2023/0057571 A1 | 2/2023 | Costa et al. |
| 2023/0061542 A1 | 3/2023 | Kuhnemund |
| 2023/0084407 A1 | 3/2023 | Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0242974 A1 | 8/2023 | Costa et al. |
| 2023/0279465 A1 | 9/2023 | He et al. |
| 2023/0279475 A1 | 9/2023 | Kuhnemund et al. |
| 2023/0279480 A1 | 9/2023 | Kuhnemund |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Schall-Levin |
| 2023/0323430 A1 | 10/2023 | Shastry |
| 2023/0323437 A1 | 10/2023 | Chen et al. |
| 2023/0374573 A1* | 11/2023 | Qian .................... C12Q 1/6844 |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Bava |
| 2024/0026427 A1 | 1/2024 | Kuhnemund et al. |
| 2024/0026439 A1 | 1/2024 | Sasaki |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen |
| 2024/0060119 A1 | 2/2024 | Bava |
| 2024/0084373 A1 | 3/2024 | Shastry |
| 2024/0084378 A1 | 3/2024 | Marks et al. |
| 2024/0101978 A1 | 3/2024 | Boghospor et al. |

(56) References Cited

U.S. PATENT DOCUMENTS

| | | |
|---|---|---|
| 2024/0132938 A1 | 4/2024 | Kuhnemund |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |
| 2024/0263219 A1 | 8/2024 | Kuhnemund |
| 2024/0263220 A1 | 8/2024 | Olofsson |
| 2024/0264155 A1 | 8/2024 | Costa |

FOREIGN PATENT DOCUMENTS

| | | |
|---|---|---|
| WO | WO 2019/199579 | 10/2019 |
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/240025 | 12/2020 |
| WO | WO 2020/254519 | 12/2020 |
| WO | WO 2021/123282 | 6/2021 |
| WO | WO 2021/123286 | 6/2021 |
| WO | WO 2021/138676 | 7/2021 |
| WO | WO 2021/155063 | 8/2021 |
| WO | WO 2021/168326 | 8/2021 |
| WO | WO 2022/056078 | 3/2022 |
| WO | WO 2023/108139 | 6/2023 |
| WO | WO 2023/141476 | 7/2023 |
| WO | WO 2023/172915 | 9/2023 |
| WO | WO 2023/192302 | 10/2023 |
| WO | WO 2024/148300 | 7/2024 |

OTHER PUBLICATIONS

Bibikova et al., "Quantitative gene expression profiling in formalin-fixed, paraffin-embedded tissues using universal bead arrays," Am J Pathol. Nov. 2004;165(5):1799-807.
Capodieci et al., "Gene expression profiling in single cells within tissue," Nat Methods. (2005) 2(9): 663-5.
Chen et al., "Efficient in situ barcode sequencing using padlock probe-based BaristaSeq," Nucleic Acids Res. (2018) 46(4): e22.
Conze et al., "Single molecule analysis of combinatorial splicing," Nucleic Acids Res. (2010) 38(16): e163.
Femino et al., "Visualization of single RNA transcripts in situ," Science. (1998) 280(5363): 585-90.
Gao et al., "Rolling circle amplification integrated with suspension bead array for ultrasensitive multiplex immunodetection of tumor markers," Anal Chim Acta. (2019): 1048:75-84.
Gavrilovic et al., "Automated classification of multicolored rolling circle products in dual-channel wide-field fluorescence microscopy," Cytometry A. (2011) 79(7): 518-27.
Geiss et al., "Direct multiplexed measurement of gene expression with color-coded probe pairs," Nat Biotechnol. (2008) 26(3):317-25.
Goh, J.J.L. et al. (Jul. 2020, e-pub. Jun. 15, 2020). "Highly Specific Multiplexed RNA Imaging in Tissues With Split-FISH," Nat Methods 17(7):689-693. doi: 10.1038/s41592-020-0858-0. Epub Jun. 15, 2020.
Goransson et al., "A single molecule array for digital targeted molecular analyses," Nucleic Acids Res. 2009 37(1):e7. doi: 10.1093/nar/gkn921.
Gunderson et al. "Decoding randomly ordered DNA arrays." Genome research 14.5 (2004): 870-877.

Han et al., "Quantum-dot-tagged microbeads for multiplexed optical coding of biomolecules," Nat Biotechnol. (2001) 19(7): 631-5.
Itzkovitz et al., "Single-molecule transcript counting of stem-cell markers in the mouse intestine," Nat Cell Biol. (2011) 14(1): 106-14.
Itzkovitz et al., "Validating Transcripts with Probes and Imaging Technology," Nat Methods. (2011) 8(4 Suppl): S12-S19.
Kielpinski et al., "RNase H sequence preferences influence antisense oligonucleotide efficiency," Nucleic Acids Res. (2017) 45(22):12932-12944.
Lagunavicius et al., "Novel application of Phi29 DNA polymerase: RNA detection and analysis in vitro and in situ by target RNA-primed RCA," RNA. (2009) 15(5):765-71.
Larsson et al. "In situ detection and genotyping of individual mRNA molecules," Nat Methods. (2010) 7(5):395-397.
Levsky et al., "Fluorescence in situ hybridization: past, present and future," J Cell Sci. (2003) 116(Pt 14): 2833-8.
Levsky et al., "Single-cell gene expression profiling," Science. (2002) 297(5582): 836-40.
Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.
Maierhorfer et al., "Multicolor deconvolution microscopy of thick biological specimens," Am J Pathol. (2003) 162(2): 373-9.
McGinn et al., "New technologies for DNA analysis—a review of the READNA Project," N Biotechnol. (2016) 33(3): 311-30. doi: 10.1016/j.nbt.2015.10.003.
Meade et al. "Multiplexed DNA detection using spectrally encoded porous SiO2 photonic crystal particles," Anal Chem. (2009) 81(7): 2618-25.
Murakami et al., "Sensitive RNA detection by combining three-way junction formation and primer generation-rolling circle amplification," Nucleic Acids Res. (2012) 40(3):e22.
Payne et al. "In situ genome sequencing resolves DNA sequence and structure in intact biological samples," Science. (2021) 371(6532): eaay3446. doi: 10.1126/science.aay3446. Epub Dec. 31, 2020.
Raj et al., "Imaging individual mRNA molecules using multiple singly labeled probes," Nat Methods. (2008) 5(10): 877-879.
Rouhanifard et al. "ClampFISH detects individual nucleic acid molecules using click chemistry-based amplification," Nat Biotechnol. (2018) 17 pages. doi: 10.1038/nbt.4286.
Rozi et al., "The mechanism and improvements to the isothermal amplification of nucleic acids, at a glance," Anal Biochem. (2021) 631:114260.
Sun et al., "Integrating barcoded neuroanatomy with spatial transcriptional profiling enables identification of gene correlates of projections," Nat Neurosci. (2021) 24(6):873-885.
Sun et al., "Composite organic-inorganic nanoparticles as Raman labels for tissue analysis," Nano Lett. (2007) 7(2): 351-6.
Takei et al., (Feb. 2021, e-pub Jan. 27, 2021). "Integrated Spatial Genomics Reveals Global Architecture of Single Nuclei," Nature 590(7845):344-350, 53 pages. doi: 10.1038/s41586-020-03126-2.
Wählby et al., "Sequential immunofluorescence staining and image analysis for detection of large numbers of antigens in individual cell nuclei," Cytometry. (2002) 47(1): 32-41.
Weibrecht et al., "Simultaneous visualization of both signaling cascade activity and end-point gene expression in single cells," PLoS One. (2011) 6(5): e20148.
Wilson et al., "Encoded microcarriers for high-throughput multiplexed detection," Angew Chem Int Ed Engl. (2006) 18;45(37): 6104-17.
Wu et al. "RollFISh Achieves Robust Quantification of Single-Molecule RNA Biomarkers in Paraffin-Embedded Tumor Tissue Samples," Commun Biol. (2018) 1:(209):1-8. doi: 10.1038/s42003-018-0218-0.
Wu et al., "Properties of cloned and expressed human RNase H1," J Biol Chem. (1999) 274(40):28270-28278.
Zhao et al., "Advances of multiplex and high throughput biomolecular detection technologies based on encoding microparticles," Sci China Chem. (2011) 54(8):1185.

* cited by examiner

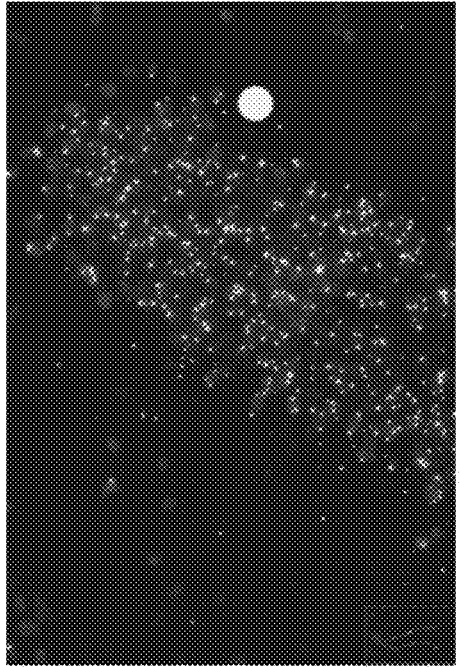
FIG. 3H
RNase H; with separate primer and no oligonucleotide
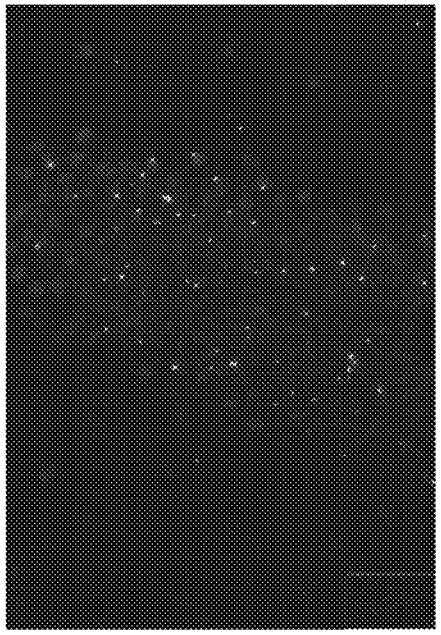
FIG. 3J
No separate oligonucleotide and no separate primer (with 1U RNase H during RCA)
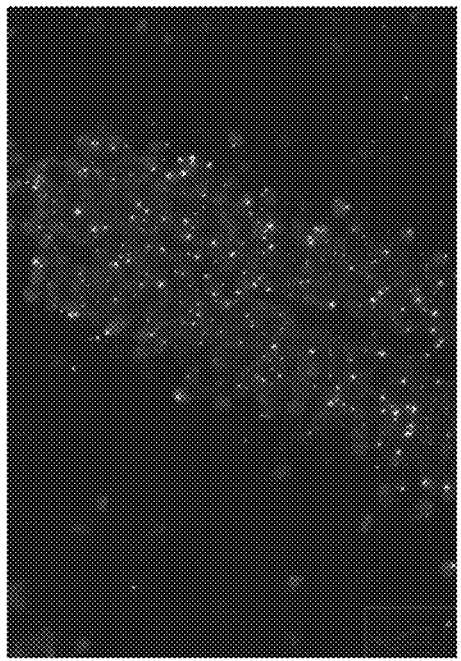
FIG. 3G
Separate primer (no RNase H)
FIG. 3I
No separate oligonucleotide and no separate primer (with 0.1U RNase H during RCA)

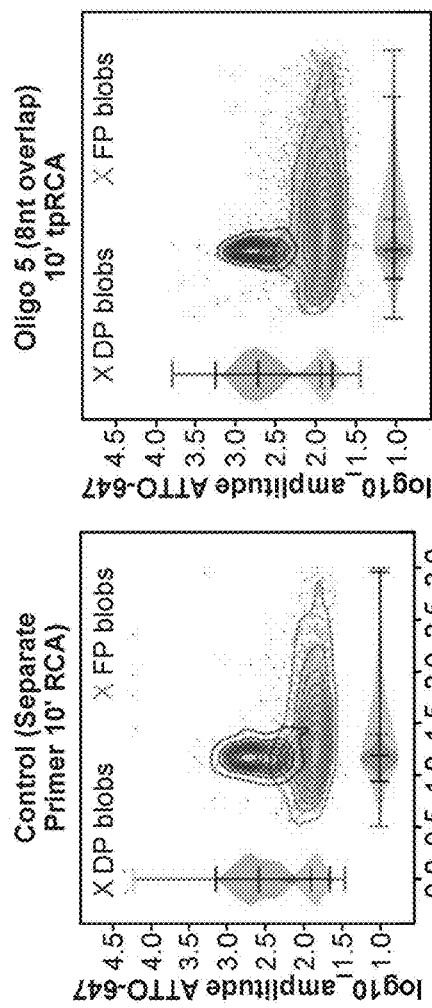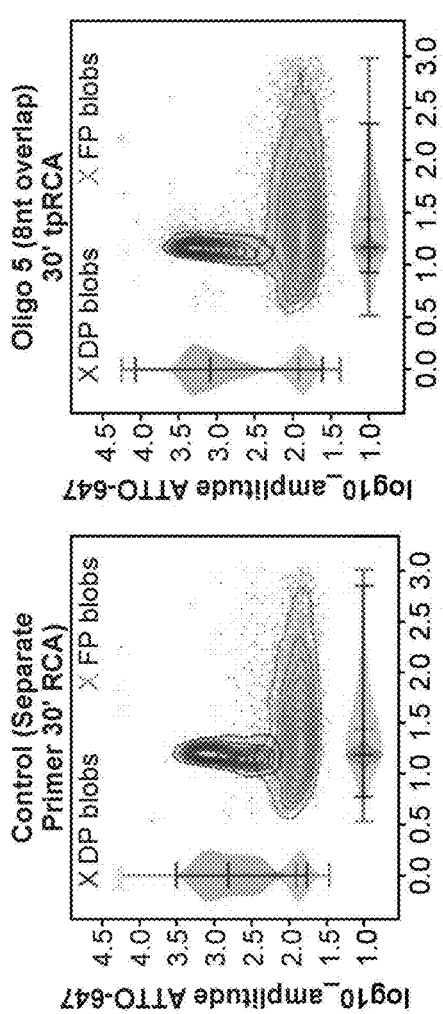

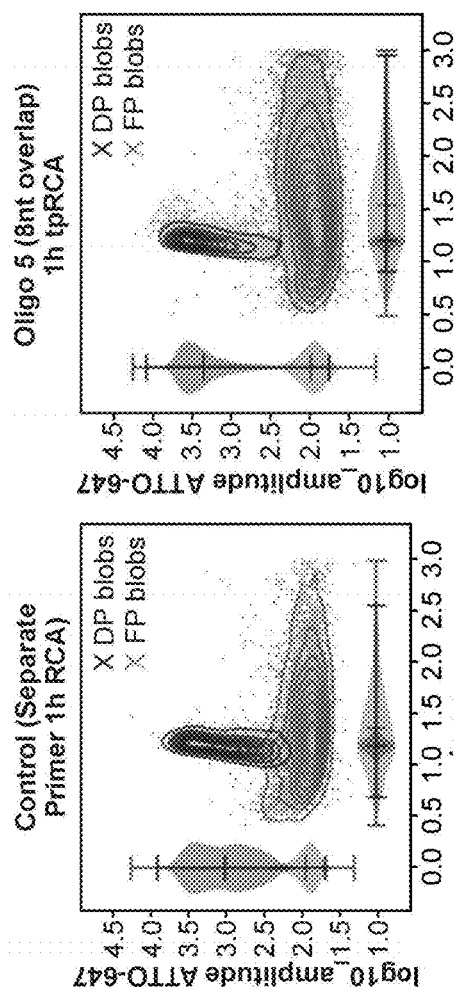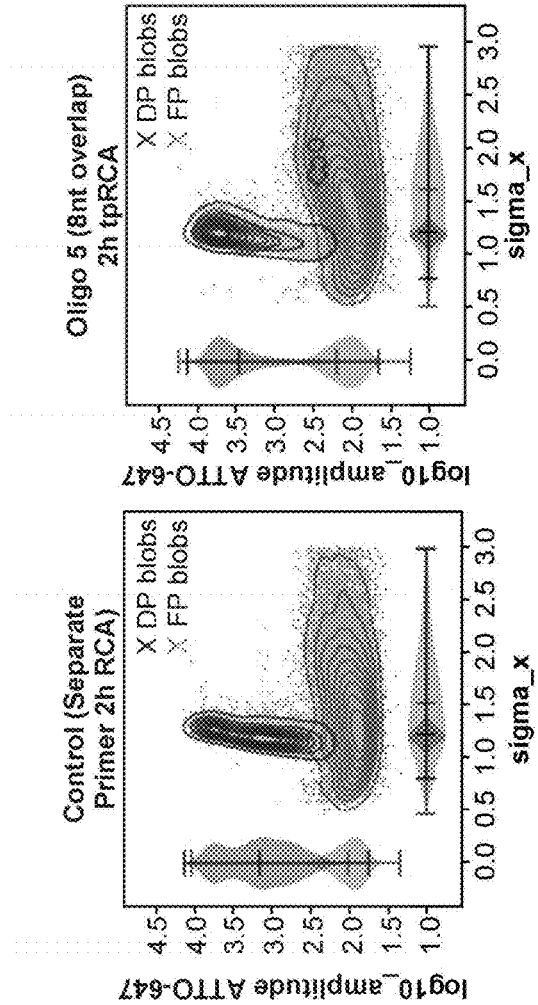

Expression in dentate gyrus
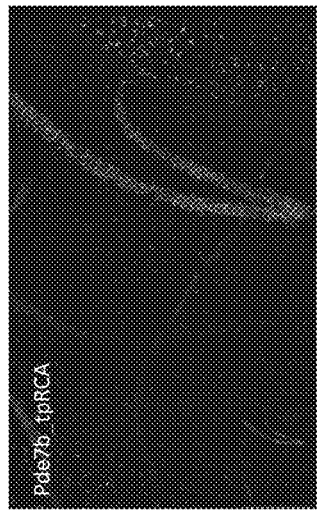
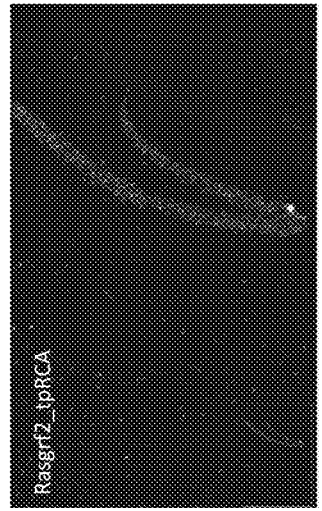
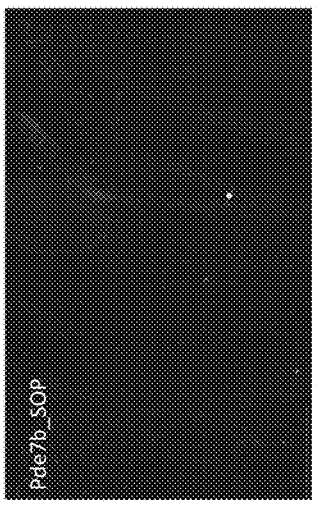
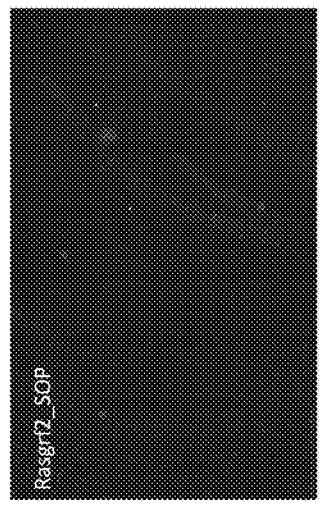
FIG. 7A

METHODS AND SYSTEMS FOR TARGETED RNA CLEAVAGE AND TARGET RNA-PRIMED ROLLING CIRCLE AMPLIFICATION

CROSS-REFERENCE TO RELATED APPLICATIONS

This application claims priority to U.S. Provisional Patent Application No. 63/516,786, filed Jul. 31, 2023, entitled "METHODS AND SYSTEMS FOR TARGETED RNA CLEAVAGE AND TARGET RNA-PRIMED ROLLING CIRCLE AMPLIFICATION," and U.S. Provisional Patent Application No. 63/659,275, filed Jun. 12, 2024, entitled "METHODS AND SYSTEMS FOR TARGETED RNA CLEAVAGE AND TARGET RNA-PRIMED ROLLING CIRCLE AMPLIFICATION," each of which is herein incorporated by reference in its entirety for all purposes.

FIELD

The present disclosure relates in some aspects to methods for in situ analysis of target nucleic acids in a biological sample.

BACKGROUND

Methods are available for analyzing nucleic acids in a biological sample in situ, such as in a cell or a tissue sample. For instance, advances in single molecule fluorescent hybridization (smFISH) have enabled nanoscale-resolution imaging of RNA in cells and tissues. Rolling circle amplification (RCA)-based detection methods allow detection of target nucleic acids such as RNA in cells and tissues. However, in some cases RCA-based assay methods for in situ analysis may suffer from low sensitivity, specificity, and/or detection efficiency. Improved methods for in situ analysis are needed. The present disclosure addresses these and other needs.

SUMMARY

RCA-based detection methods provide a powerful tool for detection of analytes at their relative spatial locations (e.g., in situ) in biological samples. However, RCA-based detection methods may suffer from low sensitivity, specificity, and/or detection efficiency. In some aspects, RCA product (RCP) heterogeneity may partially originate from a heterogenous micro-environment (e.g., secondary structures of mRNA and mRNA-protein interactions, which could both influence the polymerase activity, such as strand displacement, hindrance of processivity, etc.), asynchronous RCA, heterogeneous processivity of RCA, etc. One approach to improved RCA-based detection is to make the reaction simpler and to promote a more homogenous amplification system for the polymerase, by eliminating the use of separate nucleic acid primers. In some aspects, provided herein are methods for analyzing a biological sample wherein a nucleic acid oligonucleotide is used to provide a DNA-RNA duplex for RNase H cleavage of a target RNA in the DNA-RNA duplex. The cleaved target RNA itself can then be used to prime RCA of a circular probe or a circularized probe generated from a circularizable probe or probe set (e.g., target-primed RCA). In some aspects, using the cleaved target RNA to prime RCA results in an RCP that is covalently linked to a sequence of the target RNA. In some aspects, the methods provided herein achieve better RCP homogeneity in size and/or intensity, improved sensitivity, elevated median intensity, better signal-to-noise ratios, and/or improved localization of detected RCPs. Also provided herein are systems and kits for target-primed RCA.

In some aspects, provided herein is a method of analyzing a biological sample, comprising: a) contacting the biological sample with a nucleic acid oligonucleotide, wherein the nucleic acid oligonucleotide hybridizes to an oligonucleotide hybridization region in a target ribonucleic acid (RNA); b) contacting the biological sample with an RNase H to cleave the target RNA in the oligonucleotide hybridization region to generate a cleaved target RNA; c) contacting the biological sample with a circular probe or a circularizable probe or probe set, wherein the circular probe or the circularizable probe or probe set comprises a target recognition sequence complementary to a target sequence in the target RNA, wherein the circular probe or the circularizable probe or probe set hybridizes to the target RNA; wherein the oligonucleotide hybridization region is adjacent to the 3' end of the target sequence or is overlapping with the 3' end of the target sequence; d) performing rolling circle amplification of the circular probe or of a circularized probe generated from the circularizable probe or probe set to generate a rolling circle amplification product (RCP) using the cleaved target RNA as a primer; and e) detecting the RCP in the biological sample.

Provided herein is a method comprising hybridizing a nucleic acid oligonucleotide to an oligonucleotide hybridization region in a target ribonucleic acid (RNA) in a biological sample; cleaving the target RNA with an RNase H in the oligonucleotide hybridization region to generate a cleaved target RNA; hybridizing a circular probe or a circularizable probe or probe set comprising a target recognition sequence complementary to a target sequence in the target RNA; wherein the oligonucleotide hybridization region is adjacent to the 3' end of the target sequence or is overlapping with the 3' end of the target sequence; performing rolling circle amplification of the circular probe or of a circularized probe generated from the circularizable probe or probe set to generate a rolling circle amplification product (RCP) using the cleaved target RNA as a primer; and detecting the RCP in the biological sample.

In some embodiments, the biological sample is contacted with the nucleic acid oligonucleotide and with the RNase H simultaneously before contacting the biological sample with the circular probe or the circularizable probe or probe set. In any of the embodiments herein, the method can comprise washing the biological sample after contacting the biological sample with the Rnase H and before contacting the biological sample with the circular probe or the circularizable probe or probe set.

In some embodiments, the method comprises reacting at least one RNA in the biological sample with a polynucleotide kinase (PNK). In some embodiments, the method comprises reacting at least one RNA in the biological sample with the PNK before contacting the biological sample with the circular probe or the circularizable probe or probe set. In some embodiments, the method comprises reacting at least one RNA in the biological sample with the PNK before contacting the biological sample with the nucleic acid oligonucleotide and the RNase H. In some embodiments, the method comprises reacting at least one RNA in the biological sample with the PNK after contacting the biological sample with the nucleic acid oligonucleotide and the RNase H. In some embodiments, the PNK is a T4 Polynucleotide Kinase (T4 PNK) or a T7 Polynucleotide Kinase (T7-PNK). In some embodiments, the PNK is a T4 PNK.

In some embodiments, the oligonucleotide hybridization region and the target sequence overlap by about 1 to about 20 nucleotides. In some embodiments, the oligonucleotide hybridization region and the target sequence overlap by about 8 to about 10 nucleotides. In some embodiments, the oligonucleotide hybridization region and the target sequence overlap by at least 8 nucleotides, at least 9 nucleotides, or at least 10 nucleotides. In some embodiments, the oligonucleotide hybridization region and the target sequence overlap by no more than 15 nucleotides, no more than 12 nucleotides, or no more than 10 nucleotides.

In any of the embodiments herein, the method may comprise performing the rolling circle amplification without contacting the biological sample with a DNA primer that hybridizes to the circular probe or the circularized probe. In any of the embodiments herein, the target recognition sequence of the circularizable probe or probe set comprises a split recognition sequence comprising a first hybridization region having a first ligatable end and a second hybridization region having a second ligatable end, wherein the first hybridization region hybridizes to a 5' portion of the target sequence, and the second hybridization region hybridizes to a 3' portion of the target sequence, and the method can comprise ligating the first ligatable end to the second ligatable end to generate the circularized probe. In any of the embodiments herein, the 5' portion of the target sequence and the 3' portion of the target sequence can each be about 15 to about 30 nucleotides in length. In some embodiments, the 5' portion of the target sequence and the 3' portion of the target sequence are each about 20 nucleotides in length. In any of the embodiments herein, the oligonucleotide hybridization region and the 3' portion of the target sequence can overlap by about 8 to about 10 nucleotides.

In any of the embodiments herein, the target RNA is attached directly or indirectly to the biological sample or to a matrix embedding the biological sample. In any of the embodiments herein, the target RNA is crosslinked in the biological sample or in a matrix embedding the biological sample. In any of the embodiments herein, the RCP is covalently linked to the target RNA.

In any of the embodiments herein, the RNase H can comprise an RNase H1 and/or an RNase H2. In any of the embodiments herein, contacting the biological sample with the RNase H can comprise contacting the biological sample with between about 0.5 enzyme units (U) and about 50 U of the RNase H. In any of the embodiments herein, contacting the biological sample with the RNase H can comprise contacting the biological sample with between about 0.5 enzyme units (U) and about 10 U of the RNase H.

In any of the embodiments herein, the oligonucleotide hybridization region can comprise an AA or AU sequence, wherein the AA or AU sequence is 1, 2, 3, 4, 5, or 6 nucleotides downstream of a cytosine or a guanine. In any of the embodiments herein, the oligonucleotide hybridization region can comprise a sequence of at least 2, 3, 4, or more cytosines and/or guanines beginning at a position 2, 3, 4, 5, or 6 nucleotides upstream of the AA or AU sequence. In any of the embodiments herein, the oligonucleotide hybridization region can comprise a CAAG sequence.

In any of the embodiments herein, the oligonucleotide hybridization region is about 10 to about 20 nucleotides in length, or about 15 to about 20 nucleotides in length. In any of the embodiments herein, the nucleic acid oligonucleotide is about 10 to about 20 nucleotides in length, or about 15 to about 20 nucleotides in length. In any of the embodiments herein, the nucleotide sequence 5' and adjacent to the oligonucleotide hybridization region can comprise a sequence of 1, 2, 3, 4, or more guanines and/or cytosines. In any of the embodiments herein, the oligonucleotide hybridization region comprises 1, 2, 3, 4, or more guanines and/or cytosines within 5-8 nucleotides of its 3' end. In any of the embodiments herein, the nucleic acid oligonucleotide is single-stranded. In any of the embodiments herein, the nucleic acid oligonucleotide comprises at least 4, 5, 6, 7, or 8 consecutive deoxyribonucleotides. In any of the embodiments herein, the nucleic acid oligonucleotide is a deoxyribonucleic acid (DNA) oligonucleotide.

In any of the embodiments herein, performing the rolling circle amplification can comprise incubating the biological sample with a polymerase for a duration of between about 30 minutes and about 2 hours. In any of the embodiments herein, the method can comprise contacting the biological sample with a polymerase in a first reaction mixture comprising a di-cation that is not a co-factor of the polymerase or is a non-catalytic co-factor of the polymerase, and then contacting the biological sample with a second reaction mixture comprising a catalytic cofactor of the polymerase to perform the rolling circle amplification. In any of the embodiments herein, the di-cation that is not a co-factor of the polymerase is $Ca^{2+}$. In some instances, the non-catalytic co-factor of the polymerase is $Ca^{2+}$ or $Sr^{2+}$. In any of the embodiments herein, the di-cation that is not a co-factor of the polymerase may inhibit the polymerase activity and/or an exonuclease activity of the polymerase. In some instances, the non-catalytic co-factor of the polymerase inhibits the polymerase activity and/or an exonuclease activity of the polymerase. In some embodiments, the first reaction mixture is substantially free of a catalytic cofactor of the polymerase. In any of the embodiments herein, the first reaction mixture is substantially free of a catalytic cofactor of the polymerase selected from the group consisting of $Mg^{2+}$, $Co^{2+}$, and $Mn^{2+}$. In any of the embodiments herein, the first reaction mixture is substantially free of a catalytic cofactor of the polymerase selected from the group consisting of $Co^{2+}$ and $Mn^{2+}$. In any of the embodiments herein, the first reaction mixture comprises a chelating agent. In some embodiments, the chelating agent comprises EDTA, EGTA, BAPTA, DTPA, or a combination thereof. In any of the embodiments herein, the second reaction mixture comprises deoxynucleotide triphosphates (dNTPs) and/or nucleotide triphosphates (NTPs). In any of the embodiments herein, the second reaction mixture comprises a catalytic cofactor of the polymerase. In some embodiments, the catalytic cofactor of the polymerase is a di-cation selected from the group consisting of $Mg^{2+}$, $Co^{2+}$, and $Mn^{2+}$. In some instances, the second reaction mixture comprises $Mg^{2+}$.

In some embodiments, the circularizable probe or probe set comprises one or more ribonucleotides. In any of the embodiments herein, the one or more ribonucleotides is at and/or near a ligatable 3' end of the circularizable probe or probe set. In any of the embodiments herein, a 3' terminal nucleotide of the circularizable probe or probe set hybridized to the target RNA is a ribonucleotide.

In some embodiments, a 3' end and a 5' end of the circularizable probe or probe set are ligated using the target RNA as a template. In some embodiments, the 3' end and the 5' end of the circularizable probe or probe set are ligated without gap filling prior to ligation. In some embodiments, the ligation of the 3' end and the 5' end is preceded by gap filling. In some embodiments, the gap for gap filling is 1, 2, 3, 4, or 5 nucleotides. In any of the embodiments herein, the circularizable probe or probe set is circularized by ligation selected from the group consisting of enzymatic ligation, chemical ligation, template dependent ligation, and template independent ligation. In any of the embodiments herein, the ligation can template dependent ligation. In any of the embodiments herein, the ligation is enzymatic ligation, wherein the enzymatic ligation comprises using a ligase having an RNA-templated DNA ligase activity and/or an RNA-templated RNA ligase activity. In any of the embodiments herein, the enzymatic ligation comprises using a ligase selected from the group consisting of a Chlorella virus DNA ligase (PBCV DNA ligase), a T4 RNA ligase, a T4 DNA ligase, and a single-stranded DNA (ssDNA) ligase.

In some embodiments, the RCP is generated using a polymerase selected from the group consisting of Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof.

In some embodiments, the RCP is immobilized in the biological sample and/or crosslinked to one or more other molecules in the biological sample. In any of the embodiments herein, the method can comprise imaging the biological sample to detect the RCP. In any of the embodiments herein, the imaging comprises detecting a signal associated with a fluorescently labeled probe that directly or indirectly binds to the RCP. In any of the embodiments herein, a sequence of the RCP is analyzed at a location in the biological sample or a matrix embedding the biological sample. In any of the embodiments herein, the sequence of the RCP is analyzed by sequential hybridization, sequencing by hybridization, sequencing by ligation, sequencing by synthesis, sequencing by binding, or a combination thereof. In any of the embodiments herein, the sequence of the RCP product can comprise one or more barcode sequences or complements thereof. In any of the embodiments herein, the one or more barcode sequences or complements thereof can correspond to the target RNA.

In some aspects, provided herein is a method of analyzing a biological sample, comprising: a) contacting the biological sample with a plurality of nucleic acid oligonucleotides, wherein a first oligonucleotide of the plurality hybridizes to a first oligonucleotide hybridization region in a first target ribonucleic acid (RNA) in the biological sample, and a second oligonucleotide of the plurality hybridizes to a second oligonucleotide hybridization region in a second target RNA in the biological sample; b) contacting the biological sample with an RNase H to cleave the first and second target RNAs in their respective oligonucleotide hybridization regions; c) contacting the biological sample with a plurality of circular probes or circularizable probes or probe sets, wherein a first circular probe or first circularizable probe or probe set of the plurality comprises a first target recognition sequence complementary to a first target sequence in the first target RNA, wherein a second circular probe or second circularizable probe or probe set of the plurality comprises a second target recognition sequence complementary to a second target sequence in the second target RNA, wherein the first and second circular probe or the first and second circularizable probe or probe set hybridize to their respective target RNAs, wherein the first oligonucleotide hybridization region is adjacent to the 3' end of the first target sequence or is overlapping with the 3' end of the first target sequence, and wherein the second oligonucleotide hybridization region is adjacent to the 3' end of the second target sequence or is overlapping with the 3' end of the second target sequence; d) performing rolling circle amplification of the first and second circular probe or of a first and second circularized probe generated from the first and second circularizable probes or probe sets to generate a first and second rolling circle amplification product (RCP) using the cleaved target RNAs as primers; and e) detecting the first and second RCPs in the biological sample. In any of the embodiments herein, the nucleic acid oligonucleotides can individually comprise at least 4, 5, 6, 7, or 8 consecutive deoxyribonucleotides. In any of the embodiments herein, the nucleic acid oligonucleotides is deoxyribonucleic acid (DNA) oligonucleotides.

In some embodiments, provided herein is a method of analyzing a biological sample, comprising: a) contacting the biological sample with a nucleic acid oligonucleotide, wherein the nucleic acid oligonucleotide hybridizes to an oligonucleotide hybridization region in a target ribonucleic acid (RNA); b) contacting the biological sample with an RNase H, wherein the RNase H cleaves the target RNA in the oligonucleotide hybridization region to generate a cleaved target RNA; c) incubating the biological sample with a polynucleotide kinase (PNK); d) contacting the biological sample with a circular probe or a circularizable probe or probe set, wherein the circular probe or the circularizable probe or probe set comprises a target recognition sequence complementary to a target sequence in the target RNA, wherein the circular probe or the circularizable probe or probe set hybridizes to the target RNA; wherein the oligonucleotide hybridization region is adjacent to the 3' end of the target sequence or is overlapping with the 3' end of the target sequence; e) performing rolling circle amplification of the circular probe or of a circularized probe generated from the circularizable probe or probe set to generate a rolling circle amplification product (RCP) using the cleaved target RNA as a primer; and f) detecting the RCP in the biological sample. In some embodiments, performing the rolling circle amplification comprises contacting the biological sample with a polymerase in a first reaction mixture comprising a di-cation that is not a co-factor of the polymerase, and then contacting the biological sample with a second reaction mixture comprising a cofactor of the polymerase to perform the rolling circle amplification. In some embodiments, the di-cation that is not a co-factor of the polymerase is barium, strontium, iron, cobalt, nickel, tin, zinc, or europium.

In some embodiments, detecting the first and second RCPs in the biological sample comprises detecting barcode sequences or complements thereof in the first and second RCPs. In some embodiments, detecting the barcode sequences or complement thereof comprises: contacting the biological sample with a universal pool of detectably labeled probes and a first pool of intermediate probes, wherein the intermediate probes of the first pool of intermediate probes comprise hybridization regions complementary to the barcode sequences or complements thereof and reporter regions complementary to a detectably labeled probe of the universal pool of detectably labeled probes; detecting complexes formed between the barcode sequences or complements thereof, the intermediate probes of the first pool of intermediate probes, and the detectably labeled probes; and removing the intermediate probes of the first pool of intermediate probes and the detectably labeled probes. In any of the embodiments herein, detecting the barcode sequences or complements thereof further comprises: contacting the test biological sample with the universal pool of detectably labeled probes and a second pool of intermediate probes, wherein the intermediate probes of the second pool of intermediate probes comprise hybridization regions complementary to the barcode sequences or complements thereof and reporter regions complementary to a detectably labeled probe of the universal pool of detectably labeled probes; and detecting complexes formed between the barcode sequences or complements thereof, the intermediate probes of the second pool of intermediate probes, and the detectably labeled probes.

In some embodiments, each barcode sequence or complement thereof is assigned a series of signal codes that identifies the barcode sequence or complement thereof, and detecting the barcode sequences or complements thereof can comprises decoding the barcode sequences of complements thereof by detecting the corresponding sequences of signal codes detected from sequential hybridization, detection, and removal of sequential pools of intermediate probes and the universal pool of detectably labeled probes. In any of the embodiments herein, the series of signal codes comprises fluorophore sequences assigned to the corresponding barcode sequences or complements thereof. In any of the embodiments herein, the detectably labeled probes are fluorescently labeled.

In some embodiments, the biological sample is a fixed and/or permeabilized biological sample. In any of the embodiments herein, the biological sample is a tissue sample. In any of the embodiments herein, the biological sample is a formalin-fixed, paraffin-embedded (FFPE) tissue sample. In any of the embodiments herein, the biological sample is a frozen tissue sample or a fresh tissue sample. In any of the embodiments herein, the tissue sample is a tissue slice between about 1 µm and about 50 µm in thickness. In some embodiments, the tissue slice is between about 5 µm and about 35 µm in thickness. In any of the embodiments herein, the biological sample is crosslinked. In any of the embodiments herein, the biological sample is embedded in a hydrogel matrix. In any of the embodiments herein, the biological sample is cleared. In any of the embodiments herein, the biological sample is a biological sample that is not embedded in a hydrogel matrix.

In some aspects, provided herein is a kit for analyzing a biological sample, comprising: a) a nucleic acid oligonucleotide, wherein the nucleic acid oligonucleotide is complementary to an oligonucleotide hybridization region in a target ribonucleic acid (RNA); b) a circular probe or a circularizable probe or probe set, wherein the circular probe or the circularizable probe or probe set comprises a target recognition sequence complementary to a target sequence in the target RNA, wherein the target sequence in the target RNA overlaps with the oligonucleotide hybridization region in the target RNA by between 1 and 20 nucleotides; and c) an RNase H for cleaving the oligonucleotide hybridization region of the target RNA when hybridized to the nucleic acid oligonucleotide.

In some aspects, provided herein is a system for analyzing a biological sample, comprising: a) a nucleic acid oligonucleotide, wherein the nucleic acid oligonucleotide is complementary to an oligonucleotide hybridization region in a target ribonucleic acid (RNA); b) a circular probe or a circularizable probe or probe set, wherein the circular probe or the circularizable probe or probe set comprises a target recognition sequence complementary to a target sequence in the target RNA, wherein the target sequence in the target RNA overlaps with the oligonucleotide hybridization region in the target RNA by between 1 and 20 nucleotides; c) an RNase H for cleaving the oligonucleotide hybridization region of the target RNA when hybridized to the nucleic acid oligonucleotide; and d) a polymerase for performing rolling circle amplification of the circular probe or a circularized probe generated from the circularizable probe or probe set, using the cleaved target RNA as a primer.

In any of the embodiments of the kit or system herein, the oligonucleotide hybridization region and the target sequence can overlap by about 8 to about 10 nucleotides. In any of the embodiments of the kit or system herein, the oligonucleotide hybridization region and the target sequence can overlap by at least 8 nucleotides, at least 9 nucleotides, or at least 10 nucleotides. In any of the embodiments of the kit or system herein, the oligonucleotide hybridization region and the target sequence may overlap by no more than 15 nucleotides, no more than 12 nucleotides, or no more than 10 nucleotides. In any of the embodiments of the kit or system herein, the target recognition sequence of the circularizable probe or probe set is a split recognition sequence comprising a first hybridization region having a first ligatable end and a second hybridization region having a second ligatable end, wherein the first hybridization region is complementary to a 5' portion of the target sequence, and the second hybridization region is complementary to a 3' portion of the target sequence. In any of the embodiments of the kit or system herein, the 5' portion of the target sequence and the 3' portion of the target sequence can each be about 15 to about 30 nucleotides in length. In some embodiments, the 5' portion of the target sequence and the 3' portion of the target sequence can each be about 20 nucleotides in length. In any of the embodiments of the kit or system herein, the oligonucleotide hybridization region and the 3' portion of the target sequence can overlap by about 8 to about 10 nucleotides. In some embodiments, the kit or system further comprises a polynucleotide kinase (PNK).

In some instances, the polymerase is in a first reaction mixture comprising a non-catalytic metal of the polymerase and the kit or system further comprises a second reaction mixture comprising a catalytic cofactor of the polymerase to perform the rolling circle amplification. In some instances, the non-catalytic metal is barium, strontium, iron, cobalt, nickel, tin, zinc, or europium. In some instances, the non-catalytic metal is calcium or strontium. In some instances, the non-catalytic metal is strontium. In some instances, the non-catalytic metal is $Ca^{2+}$. In some instances, the first reaction mixture is substantially free of a catalytic cofactor of the polymerase, optionally wherein the catalytic cofactor is selected from the group consisting of $Mg^{2+}$, $Co^{2+}$, and $Mn^{2+}$. In some instances, the catalytic cofactor is a di-cation selected from the group consisting of $Mg^{2+}$, $Co^{2+}$, and $Mn^{2+}$. In some instances, the system comprises reagents for performing sequencing by ligation, sequencing by synthesis, sequencing by binding, or a combination thereof. In some instances, the system comprises a universal pool of detectably labeled probes.

BRIEF DESCRIPTION OF THE DRAWINGS

The drawings illustrate certain features and advantages of this disclosure. These embodiments are not intended to limit the scope of the appended claims in any manner.

FIGS. 3A-3J provide fluorescent images of mouse brain tissue sections showing RCPs detected using fluorescently labeled probes, wherein the RCPs were generated using the indicated target-primed RCA or control conditions. FIG. 3A provides a fluorescent image of a mouse brain tissue section showing RCPs detected using fluorescently labeled probes, wherein the RCPs were generated using Oligo 3. FIG. 3B provides a fluorescent image of a mouse brain tissue section showing RCPs detected using fluorescently labeled probes, wherein the RCPs were generated using Oligo 4. FIG. 3C provides a fluorescent image of a mouse brain tissue section showing RCPs detected using fluorescently labeled probes, wherein the RCPs were generated using Oligo 5. FIG. 3D provides a fluorescent image of a mouse brain tissue section showing RCPs detected using fluorescently labeled probes, wherein the RCPs were generated using Oligo 6. FIG. 3E provides a fluorescent image of a mouse brain tissue section showing RCPs detected using fluorescently labeled probes, wherein the RCPs were generated using Oligo 7. FIG. 3F provides a fluorescent image of a mouse brain tissue section showing RCPs detected using fluorescently labeled probes, wherein the RCPs were generated using Oligo 8. FIG. 3G provides a fluorescent image of a mouse brain tissue section showing RCPs detected using fluorescently labeled probes, wherein the RCPs were generated using a separate primer and no RNase H. FIG. 3H provides a fluorescent image of a mouse brain tissue section showing RCPs detected using fluorescently labeled probes, wherein the RCPs were generated using RNase H with a separate primer and no oligonucleotide. FIG. 3I provides a fluorescent image of a mouse brain tissue section showing RCPs detected using fluorescently labeled probes, wherein the RCPs were generated using 0.1U RNase H with no separate oligonucleotide and no separate primer. FIG. 3J provides a fluorescent image of a mouse brain tissue section showing RCPs detected using fluorescently labeled probes, wherein the RCPs were generated using 1U RNase H with no separate oligonucleotide and no separate primer.

FIGS. 4A-4H show the sigma (size) and amplitude (signal intensity) distributions for double positive detected RCPs ("DP blobs" detected in two channels) and false positives ("FP blobs") detected using each of the indicated target-primed ("tpRCA") or control (separate primer) RCA conditions. FIG. 4A shows the sigma (size) and amplitude (signal intensity) distributions for double positive detected RCPs ("DP blobs" detected in two channels) and false positives ("FP blobs") detected after RCA for 10 minutes using a separate primer. FIG. 4B shows the sigma (size) and amplitude (signal intensity) distributions for double positive detected RCPs ("DP blobs" detected in two channels) and false positives ("FP blobs") detected after tpRCA for 10 minutes using Oligo 5. FIG. 4C shows the sigma (size) and amplitude (signal intensity) distributions for double positive detected RCPs ("DP blobs" detected in two channels) and false positives ("FP blobs") detected after RCA for 30 minutes using a separate primer. FIG. 4D shows the sigma (size) and amplitude (signal intensity) distributions for double positive detected RCPs ("DP blobs" detected in two channels) and false positives ("FP blobs") detected after tpRCA for 30 minutes using Oligo 5. FIG. 4E shows the sigma (size) and amplitude (signal intensity) distributions for double positive detected RCPs ("DP blobs" detected in two channels) and false positives ("FP blobs") detected after RCA for 1 hour using a separate primer. FIG. 4F shows the sigma (size) and amplitude (signal intensity) distributions for double positive detected RCPs ("DP blobs" detected in two channels) and false positives ("FP blobs") detected after tpRCA for a hour using Oligo 5. FIG. 4G shows the sigma (size) and amplitude (signal intensity) distributions for double positive detected RCPs ("DP blobs" detected in two channels) and false positives ("FP blobs") detected after RCA for 2 hours using a separate primer. FIG. 4H shows the sigma (size) and amplitude (signal intensity) distributions for double positive detected RCPs ("DP blobs" detected in two channels) and false positives ("FP blobs") detected after tpRCA for 2 hours using Oligo 5.

FIG. 5A provides cumulative distribution function curves for detected RCP sizes for target-primed RCA compared to control with 10 minutes RCA incubation. FIG. 5B provides cumulative distribution function curves for detected RCP sizes for target-primed RCA compared to control with 30 minutes RCA incubation. FIG. 5C provides cumulative distribution function curves for detected RCP sizes for target-primed RCA compared to control with 1 hour RCA incubation.

FIGS. 7A-7B provide fluorescent images of mouse brain tissue sections showing the results of target-primed RCA compared to control (separate primer) for detection of the indicated genes in the dentate gyrus, detected using a single probe per target RNA. FIG. 7A provides fluorescent images of mouse brain tissue sections showing the results of target-primed RCA compared to control (separate primer) for detection of Bdnf, Pde7b, or Rasgrf2 in the dentate gyrus, detected using a single probe per target RNA. FIG. 7B provides fluorescent images of mouse brain tissue sections showing the results of target-primed RCA compared to control (separate primer) for detection of Npy2r, Pdyn, or Thsd7a in the dentate gyrus, detected using a single probe per target RNA.

FIG. 11A provides a fluorescent image of a human pancreas tissue section showing the detection of a panel of 1,000 genes under the control condition. FIG. 11B provides a fluorescent image of a human pancreas tissue section showing the results of target-primed RCA for detection of a panel of 1,000 genes. FIG. 11C provides a fluorescent image of a human kidney tissue section showing the detection of a panel of 5,000 genes under the control condition. FIG. 11D provides a fluorescent image of a human kidney tissue section showing the results of target-primed RCA for detection of a panel of 5,000 genes.

DETAILED DESCRIPTION

Figure 1:
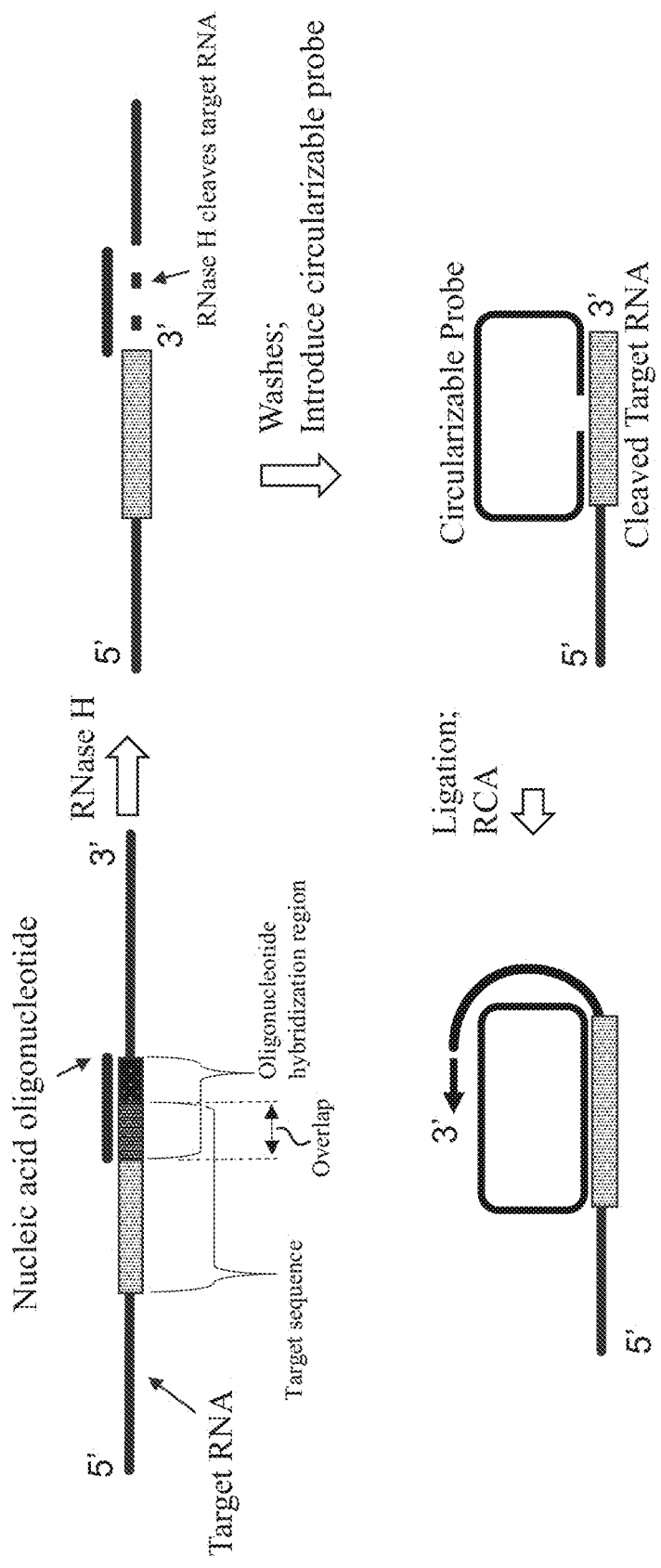
FIG. 1 depicts provides a schematic illustration of a method for target-primed RCA using a nucleic acid oligonucleotide to hybridize to a target RNA for RNase H cleavage of the target RNA, wherein the cleaved target RNA is used to prime RCA of a circular or circularized probe hybridized to the target RNA. As shown in the figure, the oligonucleotide hybridization region can overlap with the target sequence for the circular or circularized probe.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Provided herein are methods, compositions, kits, and systems for target RNA-primed rolling circle amplification of circular or circularized probes or probe sets. In some aspects, the methods disclosed herein allow targeting of RNase H activity to a particular region in a target RNA that is adjacent to or overlapping with a target sequence for the primary probe or probe set (which can be circular or circularizable, e.g., by ligation). For example, a nucleic acid oligonucleotide is designed to hybridize to a complementary oligonucleotide hybridization region in the target RNA. The nucleic acid oligonucleotide can be a DNA oligonucleotide, or can comprise at least 3, 4, 5, 6, 10, or more contiguous DNA bases to provide a DNA-RNA duplex upon hybridization to the target RNA. Formation of the DNA-RNA duplex allows RNase H to cleave the target RNA within the duplex region (e.g., within the oligonucleotide hybridization region) to generate a cleaved target RNA. Optionally, one or more washes can be performed to remove the nucleic acid oligonucleotide and/or the RNase H before contacting the biological sample with the circular or circularizable probe or probe set. In some embodiments, the circular or circularizable probe or probe set hybridizes to the cleaved target RNA, and the cleaved target RNA is used to prime RCA (optionally after one, two, or more ligations to circularize the circularizable probe or probe set).

Provided herein is a method of analyzing a biological sample by contacting the biological sample with a nucleic acid oligonucleotide, wherein the nucleic acid oligonucleotide hybridizes to an oligonucleotide hybridization region in a target ribonucleic acid (RNA); contacting the biological sample with an RNase H to cleave the target RNA in the oligonucleotide hybridization region to generate a cleaved target RNA; and after cleavage, hybridizing a circular probe or a circularizable probe or probe set to a target sequence in the cleaved target RNA.

In some aspects, the methods for target-primed RCA provided herein simplify the reaction by eliminating the need for a separate primer. In some cases, a primer-binding sequence is omitted from the circular or circularizable probe or probe set (e.g., padlock probe). This can save space in the primary probe or probe set (e.g., saving 20 nucleotides space for a 20 nucleotide primer-binding sequence), which can be used for other purposes, such as to reduce the overall length, and/or introduce other sequences with various detection schemes into the probe or probe set.

Another advantage of the provided methods in some aspects is that the resulting RCPs are covalently attached to their respective cleaved target RNAs (or a portion of their cleaved target RNAs). In some aspects, this increases positional stability of the RCPs in the biological sample and improves accuracy of localization for detected target genes based on detection of RCPs associated with the target genes. In some cases, by cutting the site next to the target recognition sequence where the probe binds the target RNA may lead to the reduction of the tension and/or hinderance from a heavily entangled mRNA in its micro-environment, and may promote a more relaxed and uniform milieu for the polymerase.

In some aspects, the present application provides designs for nucleic acid oligonucleotides that achieve highly sensitive target-primed RCA, resulting in improved sensitivity (number of detected RCPs), signal intensity, and homogeneity (e.g., narrower size and intensity distributions) compared to RCA reactions using a separate primer. Example 1, for example, demonstrates that nucleic acid oligonucleotides designed to hybridize to oligonucleotide hybridization regions having an 8-10 nucleotide overlap with a target sequence for the circular or circularizable probe or probe set to be amplified achieve the greatest increase in signal intensity and number of detected RCPs compared to control. Without being bound by theory, the special advantages of using nucleic acid oligonucleotides that bind to regions overlapping the target sequence for RNase H cutting may be because the exonuclease activity of Phi29 is slow on RNA. Therefore, cleaved target RNA that is able to hybridize to the circular or circularized probe and primer RCA without requiring further exonucleolytic cleavage may prime RCA more efficiently.

In some aspects, the present application also provides designs for circular or circularizable probes for use with the nucleic acid oligonucleotides in methods of target-primed RCA. In some embodiments, the GC content in the target recognition sequence (complementary to the target sequence) of the circular or circularizable probe or probe set is designed for strong hybridization to the target RNA, even after RNase H cleavage within a region that overlaps with the target sequence. To illustrate the advantages of this design in certain embodiments, consider the following example: if a target mRNA is cut by RNase H using a nucleic acid oligonucleotide that hybridizes to a region overlapping the target sequence of a padlock probe, the remaining docking site for the 3' arm of the padlock (originally 20 nucleotides in length) may no longer be 20 nucleotides in length. For example, the RNase H may cleave and remove at least 1, 2, 3, 4, 5, 6, 7, 8, 9, or 10 nucleotides from the 3' end of the target sequence. This reduction in the target sequence length after cleavage would influence the hybridization efficiency (e.g., reducing efficiency of hybridization at 50° C.). In some embodiments, the circularizable probe or probe set and the nucleic acid oligonucleotide are designed such that there is a G/C lock at the end of the mRNA molecule after cutting. In some embodiments, the presence of the G/C lock at the end of the cleaved target RNA assists with hybridization of the 3' portion of the target recognition sequence, improving ligation efficiency for RCA.

Additional aspects of the methods, compositions, kits, and systems disclosed herein are described in the sections below.

II. Methods for Target-Primed RCA

In some aspects, provided herein are methods for target RNA-primed rolling circle amplification of circular or circularized probes, using RNase H and a nucleic acid oligonucleotide to provide a DNA-RNA duplex upon hybridization to the target RNA, for cleavage of the target RNA by the RNase H. As illustrated in FIG. 1, in some embodiments, the method comprises hybridizing a nucleic acid oligonucleotide to an oligonucleotide hybridization region in a target RNA to form a DNA-RNA duplex with at least a portion of the oligonucleotide hybridization region. RNase H can then cleave the target RNA within the oligonucleotide hybridization region, as shown in FIG. 1. In some embodiments, one or more washes are then performed, and the biological sample is contacted with a circularizable probe such as a padlock probe which is allowed to hybridize to the target RNA, as illustrated in FIG. 1. Although a padlock probe as the circularizable probe design is illustrated in FIG. 1, the probe can be any circular or circularizable probe or probe set that can be used to provide a template for RCA (e.g., a circularizable probe or probe set can be circularized by one, two, three, four or more ligations). After incubating the sample to allow the circularizable probe to hybridize to the target RNA, the probe can be ligated (circularized), and RCA can be performed using the cleaved target RNA to prime RCA. FIG. 1A also illustrates how the target sequence for the circular or circularizable probe or probe set can overlap with the oligonucleotide hybridization region (e.g., by 1, 2, 3, 4, 5, 6, 7, 8, 9, 10, or more nucleotides). In some cases, this design (overlapping oligonucleotide hybridization region and target sequence) allows for target-primed RCA without any or without substantial exonuclease activity by the polymerase.

In some embodiments, provided herein is a method of analyzing a biological sample, comprising: a) contacting the biological sample with a nucleic acid oligonucleotide, wherein the nucleic acid oligonucleotide hybridizes to an oligonucleotide hybridization region in a target ribonucleic acid (RNA); b) contacting the biological sample with an RNase H to cleave the target RNA in the oligonucleotide hybridization region to generate a cleaved target RNA; c) contacting the biological sample with a circular probe, wherein the circular probe comprises a target recognition sequence complementary to a target sequence in the target RNA, wherein the circular probe hybridizes to the target RNA; wherein the oligonucleotide hybridization region is adjacent to the 3' end of the target sequence or is overlapping with the 3' end of the target sequence; d) performing rolling circle amplification of the circular probe to generate a rolling circle amplification product (RCP) using the cleaved target RNA as a primer; and e) detecting the RCP in the biological sample. In some embodiments, the method comprises washing the biological sample after contacting the biological sample with the circular probe. In some embodiments, the sequence of the circular probe comprises a sequence complementary to the 3' sequence of the oligonucleotide hybridization region of the target RNA. In some instances, a circular probe may provide certain benefits, for example, increased specificity, reduce probe-to-probe interactions, increase efficiency by not requiring a ligation, and/or reduce hybridization times for the probe to the target RNA.

In some embodiments, the biological sample is contacted with the oligonucleotide and with the RNase H simultaneously or sequentially (in either order) before contacting the sample with the circular probe or the circularizable probe or probe set. In some embodiments, the biological sample is contacted with the oligonucleotide and with the RNase H before contacting the sample with the circular probe or the circularizable probe or probe set. In some embodiments, the method comprises washing the biological sample after contacting the biological sample with the RNase H and before contacting the biological sample with the circular probe or the circularizable probe or probe set. In some embodiments, RNase inactivating agents or inhibitors can be added to the sample after cleave the target RNA. In some embodiments, the oligonucleotide hybridization region and the target sequence overlap by about 1 to about 20 nucleotides or by about 8 to about 10 nucleotides. The nucleic acid oligonucleotide can be as described in any of the embodiments in Section II.A.

In some embodiments, provided herein is a method of analyzing a biological sample, comprising: a) contacting the biological sample with a nucleic acid oligonucleotide, wherein the nucleic acid oligonucleotide hybridizes to an oligonucleotide hybridization region in a target ribonucleic acid (RNA); b) contacting the biological sample with an RNase H to cleave the target RNA in the oligonucleotide hybridization region to generate a cleaved target RNA; c) contacting the biological sample with a circularizable probe, wherein the circularizable probe comprises a target recognition sequence complementary to a target sequence in the target RNA, wherein the circularizable probe hybridizes to the target RNA; wherein the oligonucleotide hybridization region is adjacent to the 3' end of the target sequence or is overlapping with the 3' end of the target sequence; d) performing rolling circle amplification of a circularized probe generated from the circularizable probe to generate a rolling circle amplification product (RCP) using the cleaved target RNA as a primer; and e) detecting the RCP in the biological sample. In some embodiments, the biological sample is contacted with the oligonucleotide and with the RNase H simultaneously or sequentially (in either order) before contacting the sample with the circular probe or the circularizable probe or probe set. In some embodiments, the method comprises washing the biological sample after contacting the biological sample with the RNase H and before contacting the biological sample with the circular probe or the circularizable probe or probe set. In some embodiments, the oligonucleotide hybridization region and the target sequence overlap by about 1 to about 20 nucleotides or by about 8 to about 10 nucleotides. The nucleic acid oligonucleotide can be as described in any of the embodiments in Section II.A.

In some embodiments, provided herein is a method of analyzing a biological sample, comprising: a) contacting the biological sample with a nucleic acid oligonucleotide, wherein the nucleic acid oligonucleotide hybridizes to an oligonucleotide hybridization region in a target ribonucleic acid (RNA); b) contacting the biological sample with an RNase H to cleave the target RNA in the oligonucleotide hybridization region to generate a cleaved target RNA; c)

contacting the biological sample with a circularizable probe set, wherein the circularizable probe set comprises a target recognition sequence complementary to a target sequence in the target RNA, wherein the circularizable probe set hybridizes to the target RNA; wherein the oligonucleotide hybridization region is adjacent to the 3' end of the target sequence or is overlapping with the 3' end of the target sequence; d) performing rolling circle amplification of a circularized probe generated from the circularizable probe set to generate a rolling circle amplification product (RCP) using the cleaved target RNA as a primer; and e) detecting the RCP in the biological sample. In some embodiments, the biological sample is contacted with the oligonucleotide and with the RNase H simultaneously or sequentially (in either order) before contacting the sample with the circular probe or the circularizable probe or probe set. In some embodiments, the method comprises washing the biological sample after contacting the biological sample with the RNase H and before contacting the biological sample with the circular probe or the circularizable probe or probe set. In some embodiments, the oligonucleotide hybridization region and the target sequence overlap by about 1 to about 20 nucleotides or by about 8 to about 10 nucleotides. The nucleic acid oligonucleotide can be as described in any of the embodiments in Section II.A.

In some embodiments, provided herein is a method of analyzing a biological sample, comprising: a) contacting the biological sample with a nucleic acid oligonucleotide, wherein the nucleic acid oligonucleotide hybridizes to an oligonucleotide hybridization region in a target ribonucleic acid (RNA); b) contacting the biological sample with an RNase H to cleave the target RNA in the oligonucleotide hybridization region to generate a cleaved target RNA; c) contacting the biological sample with a circular probe, wherein the circular probe comprises a target recognition sequence complementary to a target sequence in the target RNA, wherein the circular probe hybridizes to the target RNA; wherein the oligonucleotide hybridization region is overlapping with the 3' end of the target sequence; d) performing rolling circle amplification of the circular probe to generate a rolling circle amplification product (RCP) using the cleaved target RNA as a primer; and e) detecting the RCP in the biological sample. In some embodiments, the oligonucleotide hybridization region and the target sequence overlap by about 8 to about 10 nucleotides. In some embodiments, the target sequence is between about 20 and about 60, between about 20 and 50, or between about 30 and about 45 nucleotides in length. In some embodiments, the target sequence is about 25, 30, 35, 40, or 45 nucleotides in length, or any length in a range having endpoints selected from the group consisting of 25, 30, 35, 40, or 45 nucleotides in length. In some embodiments, the oligonucleotide hybridization region is between about 10 and about 30, between about 10 and about 25, between about 15 and about 30, between about 15 and about 25, between about 10 and about 20, or between about 15 and about 25 nucleotides in length. The nucleic acid oligonucleotide can be as described in any of the embodiments in Section II.A.

In some embodiments, provided herein is a method of analyzing a biological sample, comprising: a) contacting the biological sample with a nucleic acid oligonucleotide, wherein the nucleic acid oligonucleotide hybridizes to an oligonucleotide hybridization region in a target ribonucleic acid (RNA); b) contacting the biological sample with an RNase H to cleave the target RNA in the oligonucleotide hybridization region to generate a cleaved target RNA; c) contacting the biological sample with a circularizable probe, wherein the circularizable probe comprises a target recognition sequence complementary to a target sequence in the target RNA, wherein the circularizable probe hybridizes to the target RNA; wherein the oligonucleotide hybridization region is overlapping with the 3' end of the target sequence; d) performing rolling circle amplification of a circularized probe generated from the circularizable probe to generate a rolling circle amplification product (RCP) using the cleaved target RNA as a primer; and e) detecting the RCP in the biological sample. In some embodiments, the oligonucleotide hybridization region and the target sequence overlap by about 8 to about 10 nucleotides. In some embodiments, the oligonucleotide hybridization region and the target sequence overlap by about 8 to about 10 nucleotides. In some embodiments, the target sequence is between about 20 and about 60, between about 20 and 50, or between about 30 and about 45 nucleotides in length. In some embodiments, the target sequence is about 25, 30, 35, 40, or 45 nucleotides in length, or any length in a range having endpoints selected from the group consisting of 25, 30, 35, 40, or 45 nucleotides in length. In some embodiments, the oligonucleotide hybridization region is between about 10 and about 30, between about 10 and about 25, between about 15 and about 30, between about 15 and about 25, between about 10 and about 20, or between about 15 and about 25 nucleotides in length. The nucleic acid oligonucleotide can be as described in any of the embodiments in Section II.A.

In some embodiments, provided herein is a method of analyzing a biological sample, comprising: a) contacting the biological sample with a plurality of nucleic acid oligonucleotides, wherein each of the nucleic acid oligonucleotides hybridize to an oligonucleotide hybridization region in a target ribonucleic acid (RNA). In some embodiments, the plurality of nucleic acid oligonucleotides comprises a first nucleic acid oligonucleotide that hybridizes to a first oligonucleotide hybridization region in the target RNA and a second nucleic acid oligonucleotide that hybridizes to a second oligonucleotide hybridization region in the target RNA. In some embodiments, the first and second oligonucleotide hybridization regions are separated by about 150 to 500 nucleotides, separated by about 150 to 400 nucleotides, separated by about 150 to 300 nucleotides, separated by about 150 to 200 nucleotides, separated by about 200 to 400 nucleotides, separated by about 300 to 400 nucleotides, or separated by about 200 to 300 nucleotides. In some embodiments, the first and second oligonucleotide hybridization regions are separated by less than about 500 nucleotides, less than about 400 nucleotides, less than about 300 nucleotides, or less than about 200 nucleotides. In some embodiments, the first and second oligonucleotide hybridization regions each overlap by about 8 to about 10 nucleotides with the corresponding first and second target sequences. respectively. In some embodiments, the first and second oligonucleotide hybridization regions are separated by about 200 to 300 nucleotides. In some embodiments, the first and second oligonucleotide hybridization regions are separated by greater than about 200 nucleotides, greater than about 250 nucleotides, greater than about 300 nucleotides, greater than about 350 nucleotides, or greater than about 400 nucleotides.

In some embodiments, provided herein is a method of analyzing a biological sample, comprising: a) contacting the biological sample with a nucleic acid oligonucleotide, wherein the nucleic acid oligonucleotide hybridizes to an oligonucleotide hybridization region in a target ribonucleic acid (RNA); b) contacting the biological sample with an RNase H to cleave the target RNA in the oligonucleotide hybridization region to generate a cleaved target RNA; c) contacting the biological sample with a circularizable probe set, wherein the circularizable probe set comprises a target recognition sequence complementary to a target sequence in the target RNA, wherein the circularizable probe set hybridizes to the target RNA; wherein the oligonucleotide hybridization region is overlapping with the 3' end of the target sequence; d) performing rolling circle amplification of a circularized probe generated from the circularizable probe set to generate a rolling circle amplification product (RCP) using the cleaved target RNA as a primer; and e) detecting the RCP in the biological sample. In some embodiments, the oligonucleotide hybridization region and the target sequence overlap by about 8 to about 10 nucleotides. In some embodiments, the oligonucleotide hybridization region and the target sequence overlap by about 8 to about 10 nucleotides. In some embodiments, the target sequence is between about 20 and about 60, between about 20 and 50, or between about 30 and about 45 nucleotides in length. In some embodiments, the target sequence is about 25, 30, 35, 40, or 45 nucleotides in length, or any length in a range having endpoints selected from the group consisting of 25, 30, 35, 40, or 45 nucleotides in length. In some embodiments, the oligonucleotide hybridization region is between about 10 and about 30, between about 10 and about 25, between about 15 and about 30, between about 15 and about 25, between about 10 and about 20, or between about 15 and about 25 nucleotides in length. The nucleic acid oligonucleotide can be as described in any of the embodiments in Section II.A.

In some embodiments, provided herein is a method of analyzing a biological sample, comprising: a) contacting the biological sample with plurality of nucleic acid oligonucleotides, wherein a first oligonucleotide of the plurality hybridizes to a first oligonucleotide hybridization region in a first target ribonucleic acid (RNA) in the biological sample, and a second oligonucleotide of the plurality hybridizes to a second oligonucleotide hybridization region in a second target RNA in the biological sample; b) contacting the biological sample with an RNase H, wherein the RNase H cleaves the first and second target RNAs in their respective oligonucleotide hybridization regions; c) contacting the biological sample with a plurality of circularizable probes, wherein a first circularizable probe of the plurality comprises a first target recognition sequence complementary to a first target sequence in the first target RNA, wherein a second circularizable probe of the plurality comprises a second target recognition sequence complementary to a second target sequence in the second target RNA, wherein the first and second circularizable probe hybridize to their respective target RNAs, wherein the first oligonucleotide hybridization region is adjacent to the 3' end of the first target sequence or is overlapping with the 3' end of the first target sequence, and wherein the second oligonucleotide hybridization region is adjacent to the 3' end of the second target sequence or is overlapping with the 3' end of the second target sequence; d) performing rolling circle amplification of a first and second circularized probe generated from the first and second circularizable probes, respectively, to generate a first and second rolling circle amplification product (RCP) using the cleaved target RNAs as primers; and e) detecting the first and second RCPs in the biological sample. The nucleic acid oligonucleotide can be as described in any of the embodiments in Section II.A.

In some embodiments, provided herein is a method of analyzing a biological sample, comprising: a) contacting the biological sample with plurality of nucleic acid oligonucleotides, wherein a first oligonucleotide of the plurality hybridizes to a first oligonucleotide hybridization region in a first target ribonucleic acid (RNA) in the biological sample, and a second oligonucleotide of the plurality hybridizes to a second oligonucleotide hybridization region in a second target RNA in the biological sample; b) contacting the biological sample with an RNase H, wherein the RNase H cleaves the first and second target RNAs in their respective oligonucleotide hybridization regions; c) contacting the biological sample with a plurality of circularizable probes, wherein a first circularizable probe of the plurality comprises a first target recognition sequence complementary to a first target sequence in the first target RNA, wherein a second circularizable probe of the plurality comprises a second target recognition sequence complementary to a second target sequence in the second target RNA, wherein the first and second circularizable probe hybridize to their respective target RNAs, wherein the first oligonucleotide hybridization region is overlapping with the 3' end of the first target sequence, and wherein the second oligonucleotide hybridization region is overlapping with the 3' end of the second target sequence; d) performing rolling circle amplification of a first and second circularized probe generated from the first and second circularizable probes, respectively, to generate a first and second rolling circle amplification product (RCP) using the cleaved target RNAs as primers; and e) detecting the first and second RCPs in the biological sample. The nucleic acid oligonucleotide can be as described in any of the embodiments in Section II.A.

In some embodiments, provided herein is a method of analyzing a biological sample, comprising: a) contacting the biological sample with plurality of nucleic acid oligonucleotides, wherein a first oligonucleotide of the plurality hybridizes to a first oligonucleotide hybridization region in a first target ribonucleic acid (RNA) in the biological sample, and a second oligonucleotide of the plurality hybridizes to a second oligonucleotide hybridization region in a second target RNA in the biological sample; b) contacting the biological sample with an RNase H, wherein the RNase H cleaves the first and second target RNAs in their respective oligonucleotide hybridization regions; c) contacting the biological sample with a plurality of circularizable probe sets, wherein a first circularizable probe set of the plurality comprises a first target recognition sequence complementary to a first target sequence in the first target RNA, wherein a second circularizable probe set of the plurality comprises a second target recognition sequence complementary to a second target sequence in the second target RNA, wherein the first and second circularizable probe sets hybridize to their respective target RNAs, wherein the first oligonucleotide hybridization region is overlapping with the 3' end of the first target sequence, and wherein the second oligonucleotide hybridization region is overlapping with the 3' end of the second target sequence; d) performing rolling circle amplification of a first and second circularized probe generated from the first and second circularizable probe sets, respectively, to generate a first and second rolling circle amplification product (RCP) using the cleaved target RNAs as primers; and e) detecting the first and second RCPs in the biological sample. The nucleic acid oligonucleotide can be as described in any of the embodiments in Section II.A. In some embodiments, provided herein is a method of analyzing a biological sample, comprising contacting the biological sample with plurality of nucleic acid oligonucleotides, wherein each oligonucleotide of the plurality of nucleic acid oligonucleotides hybridizes to target ribonucleic acid (RNA) of a plurality of target RNAs (e.g., different analytes) in the biological sample. In some embodiments, the plurality of nucleic acid oligonucleotides comprises at least 2, at least 5, at least 10, at least 25, at least 50, at least 75, at least 100, at least 300, at least 1,000, at least 3,000, at least 10,000, at least 30,000, at least 50,000, at least 100,000, at least 250,000, at least 500,000, or at least 1,000,000 distinguishable nucleic acid oligonucleotides. In some embodiments, the plurality of nucleic acid oligonucleotides comprises at least 250 distinguishable nucleic acid oligonucleotides. In some embodiments, the plurality of nucleic acid oligonucleotides comprises at least 500 distinguishable nucleic acid oligonucleotides. In some embodiments, subsets of the plurality of nucleic acid oligonucleotides may be complementary to different sequences of the same target RNA. For example, at least 2, 3, 4, 5, 6, 7, 8, 9, or 10 nucleic acid oligonucleotides may hybridize to non-overlapping sequences of the same target RNA.

In some embodiments, detecting the first and second RCPs in the sample comprises detecting barcode sequences or complements thereof in the first and second RCPs. In some embodiments, detecting the barcode sequences or complement thereof comprises sequential hybridization cycles of intermediate probes that hybridize to barcode sequences or subunits thereof in the RCP, and detectably labeled probes that bind directly or indirectly to the intermediate probes. For example, in some embodiments, detecting the barcode sequences or complements thereof in the RCPs comprises: contacting the test biological sample with a universal pool of detectably labeled probes and a first pool of intermediate probes, wherein the intermediate probes of the first pool of intermediate probes comprise hybridization regions complementary to the barcode sequence or complements thereof and reporter regions complementary to a detectably labeled probe of the universal pool of detectably labeled probes; detecting complexes formed between the barcode sequences or complements thereof, the intermediate probes of the first pool of intermediate probes, and the detectably labeled probes; and removing the intermediate probes of the first pool of intermediate probes and the detectably labeled probes. In some embodiments, detecting the barcode sequences or complements thereof further comprises: contacting the test biological sample with the universal pool of detectably labeled probes and a second pool of intermediate probes, wherein the intermediate probes of the second pool of intermediate probes comprise hybridization regions complementary to the barcode sequences or complements thereof and reporter regions complementary to a detectably labeled probe of the universal pool of detectably labeled probes; and detecting complexes formed between the barcode sequences or complements thereof, the intermediate probes of the second pool of intermediate probes, and the detectably labeled probes. In some embodiments, each barcode sequence or complement thereof is assigned a series of signal codes that identifies the barcode sequence or complement thereof, and detecting the barcode sequences or complements thereof comprises decoding the barcode sequences of complements thereof by detecting the corresponding sequences of signal codes detected from sequential hybridization, detection, and removal of sequential pools of intermediate probes and the universal pool of detectably labeled probes. In some embodiments, the series of signal codes are fluorophore sequences assigned to the corresponding target RNA.

In some embodiments, detecting the first and second RCPs in the sample comprises detecting a series of barcode sequences (e.g., subunits of a barcode sequence that together identify the RCP and corresponding target RNA) in the first and second RCPs. In some embodiments, detecting the series of barcode sequences comprises sequential hybridization of probes to different barcode sequences or subunits present in an RCP in a pre-determined order. For example, a first detectably labeled probe can be hybridized to a first barcode sequence or barcode subunit in an RCP and detected (e.g., by imaging the biological sample). After detection of the first detectably labeled probe, the probe can be removed by washing, or a detectable label associated with the first detectably labeled probe can be quenched or removed by cleavage (e.g., cleavage of a disulfide linker connecting the detectable label to the probe). Next, a second detectably labeled probe can be hybridized to a second barcode sequence or barcode subunit in the RCP and detected (e.g., by imaging the biological sample). In some cases, the RCP is assigned a series of signal codes that identify the corresponding target RNA. For example, in some embodiments, the first detected signal for the first detectably labeled probe hybridized to the first barcode sequence or barcode subunit corresponds to the first signal code in the series, and the second detected signal for the second detectably labeled probe hybridized to the second barcode sequence or barcode subunit corresponds to the second signal code in the series. In some embodiments, the series of signal codes are fluorophore sequences assigned to the corresponding target RNA.

In some embodiments, the method does not comprise contacting the biological sample with a DNA primer that hybridizes to the circular probe or the circularized probe. In some aspects, this saves space in the length of the circular probe, circularizable probe, or circularizable probe set that is used to provide a template for RCA. Given cost constraints for synthesizing longer nucleic acid probes, eliminating the requirement for a primer hybridization region has significant practical advantages. Shorter probes can be used without reducing the number or length of barcode sequences for detection of RCPs produced using the probes as templates, or additional or longer barcode sequences can be included without increasing the length of the nucleic acid probes.

In some embodiments wherein the primary probe is a circularizable probe, the target recognition sequence of the circularizable probe is a split recognition sequence comprising a first hybridization region having a first ligatable end and a second hybridization region having a second ligatable end, wherein the first hybridization region hybridizes to a 5' portion of the target sequence, and the second hybridization region hybridizes to a 3' portion of the target sequence, and the method comprises ligating the first ligatable end to the second ligatable end to generate the circularized probe. Similarly, in some embodiments wherein a circularizable probe set is used (e.g., comprising two or more nucleic acid probes that can be ligated together to form a circularized probe) the target recognition sequence of the circularizable probe set is a split recognition sequence comprising a first hybridization region in a first nucleic acid molecule having a first ligatable end and a second hybridization region in a second nucleic acid molecule having a second ligatable end, wherein the first hybridization region hybridizes to a 5' portion of the target sequence, and the second hybridization region hybridizes to a 3' portion of the target sequence, and the method comprises ligating the first ligatable end to the second ligatable end to connect the first nucleic acid molecule and the second nucleic acid molecule. The other ends of the first nucleic acid molecule and the second nucleic acid molecule can also be ligated (optionally, in a nucleic acid templated ligation using a separate oligonucleotide as a splint) to generate a circularized probe from the circularizable probe set. In some embodiments, the 5' portion of the target sequence and the 3' portion of the target sequence are each about 15 to about 30 nucleotides in length. In some embodiments, the 5' portion of the target sequence and the 3' portion of the target sequence are each about 20 nucleotides in length.

In some embodiments, the oligonucleotide hybridization region and the 3' portion of the target sequence overlap by about 8 to about 12 nucleotides. For example, in FIG. 2, Oligo 5 overlaps with the 3' portion of the target sequence by 8 nucleotides, and Oligo 6 overlaps with the 3' portion of the target sequence by 10 nucleotides. In some embodiments, the 3' portion of the target sequence is between about 15 and about 30 nucleotides in length, between about 15 and about 25 nucleotides in length, between about 18 and about 24 nucleotides in length, or between about 18 and about 22 nucleotides in length.

A. Oligonucleotides for RNase H Cutting

In some aspects, the present application provides designs for nucleic acid oligonucleotides capable of forming DNA-RNA duplexes for RNase H cutting in at least a portion of an oligonucleotide hybridization region in a target RNA. In some embodiments, the nucleic acid oligonucleotides can be used to achieve highly sensitive target-primed RCA, resulting in improved sensitivity (number of detected RCPs), signal intensity, increased positional stability in the biological sample, improved accuracy of localization, improved signal to noise, and homogeneity (e.g., narrower size and intensity distributions) compared to RCA reactions using a separate primer. Example 1, for example, demonstrates that nucleic acid oligonucleotides designed to hybridize to oligonucleotide hybridization regions having an 8-10 nucleotide overlap with a target sequence for the circular or circularizable probe or probe set to be amplified achieve the greatest increase in signal intensity and number of detected RCPs compared to control.

In some embodiments, the oligonucleotide hybridization region and the target sequence overlap by about 1 to about 20, about 1 to about 15, about 1 to about 10, about 2 to about 10, about 2 to about 9, about 2 to about 8, about 3 to about 15, about 3 to about 10, about 5 to about 15, about 5 to about 10, about 8 to about 12 nucleotides or about 8 to about 10 nucleotides. In some embodiments, the oligonucleotide hybridization region and the target sequence overlap by at least 6 nucleotides, at least 7 nucleotides, 8 nucleotides, at least 9 nucleotides, or at least 10 nucleotides. In some embodiments, the oligonucleotide hybridization region and the target sequence overlap by no more than 15 nucleotides, no more than 12 nucleotides, or no more than 10 nucleotides. In some embodiments, the oligonucleotide hybridization region and the target sequence overlap by about 6 to 10 nucleotides. In some embodiments, the oligonucleotide hybridization region and the target sequence overlap by about 8 to 10 nucleotides. In some embodiments, the oligonucleotide hybridization region and the target sequence overlap by 8 nucleotides. In some embodiments, the oligonucleotide hybridization region and the target sequence overlap by 6 nucleotides. In some examples, the oligonucleotide hybridization region and the target sequence overlap is such that the cutting position is around 6-8 nucleotides from the (3') end of oligonucleotide. In some examples, the cutting position is between 7-9 nucleotides from the (3') end of oligonucleotide. In some examples, the cutting position is between 6-7 nucleotides from the (3') end of oligonucleotide. In some embodiments, the oligonucleotide hybridization region and the target sequence overlap is such that the cutting position is at the 3'end of the bound nucleic acid probes and/or probe sets (e.g., circular probes or circularizable probes or probe sets). In some embodiments, the melting temperature $T_m$ of the nucleic acid oligonucleotide about 60° C. to about 70° C., about 65° C. to about 70° C., about 60° C. to about 75° C., about 65° C. to about 68° C. In some embodiments, the melting temperature $T_m$ of the oligonucleotide is about 65° C. In some embodiments, the melting temperature $T_m$ of the oligonucleotide is at least 65° C. In some embodiments, the melting temperature $T_m$ of the oligonucleotide is at least 70° C.

In some embodiments, the nucleic acid oligonucleotide is single-stranded. In some embodiments, the nucleic acid oligonucleotide comprises at least 4, 5, 6, 7, or 8 consecutive deoxyribonucleotides. In some embodiments, the nucleic acid oligonucleotide is a deoxyribonucleic acid (DNA) oligonucleotide. In some cases, the nucleic acid oligonucleotide is a single-stranded DNA (ssDNA) oligonucleotide.

In some embodiments, the nucleic acid oligonucleotide is designed to hybridize to an oligonucleotide hybridization region comprising a preferred sequence motif for cutting by an RNase H, such as any of the preferred sequence motifs described in Section II.B. In some embodiments, the oligonucleotide hybridization region comprises an AA or AU sequence, wherein the AA or AU sequence is 1, 2, 3, 4, 5, or 6 nucleotides downstream of a cytosine or a guanine. In some cases, the oligonucleotide hybridization region comprises a sequence of at least 2, 3, 4, or more cytosines and/or guanines beginning at a position 2, 3, 4, 5, or 6 nucleotides upstream of the AA or AU sequence. In some instances, the oligonucleotide hybridization region comprises a CAAG sequence.

In some embodiments, the oligonucleotide hybridization region is about 10 to about 35, about 10 to about 30, about 15 to about 30, about 15 to about 35, about 20 to about 35, about 25 to about 35, about 5 to about 25, about 10 to about 20, about 15 to about 25, about 5 to about 15, about 8 to about 18, about 10 to about 18, or about 15 to about 20 nucleotides in length. In some embodiments, the oligonucleotide is about 10 to about 30, about 15 to about 30, about 5 to about 25, about 10 to about 20, about 15 to about 25, about 5 to about 15, about 8 to about 18, about 10 to about 18, or about 15 to about 20 nucleotides in length. In some embodiments, the oligonucleotide is about 20 to about 35 nucleotides in length. In some embodiments, the oligonucleotide is about 20 to about 30 nucleotides in length. In some embodiments, the length of the nucleic acid oligonucleotide is about 10 to about 40, about 10 to about 35, about 10 to about 30, about 20 to about 40, about 20 to about 35, about 20 to about 30, or about 20 to about 25 nucleotides. In some embodiments, the length of the nucleic acid oligonucleotide is about 20 to about 34 nucleotides. In some embodiments, the length of the nucleic acid oligonucleotide is at least 15 nucleotides, at least 16 nucleotides, 17 nucleotides, at least 18 nucleotides, 19 nucleotides or at least 20 nucleotides. In some instances, a nucleic acid oligonucleotide design begins with a 20 nucleotide sequence with the oligonucleotide hybridization region and the target sequence overlapping by 6 to 10 nucleotides, and extending the nucleic acid oligonucleotide length until a melting temperature $T_m$ of 65° C. is achieved. In some instances, the nucleic acid oligonucleotide is extended from 20 nucleotides to up to 34 nucleotide total in length. In some instances, a nucleic acid oligonucleotide design begins with a 20 nucleotide sequence with the oligonucleotide hybridization region and the target sequence overlapping by 6 nucleotides, and extending the nucleic acid oligonucleotide length until a melting temperature $T_m$ of 65° C. is achieved.

In some aspects, the nucleic acid oligonucleotide is designed such that the nucleotide sequence 5' and adjacent to the oligonucleotide hybridization region comprises a sequence of 1, 2, 3, 4, or more guanines and/or cytosines. In some embodiments, the oligonucleotide hybridization region comprises 1, 2, 3, 4, or more guanines and/or cytosines within 5-8 nucleotides of its 3' end. In some embodiments, the oligonucleotide hybridization region comprises 1, 2, 3, 4, or more guanines and/or cytosines within 6-7 nucleotides of its 3' end. In some embodiments, the oligonucleotide hybridization region comprises 1, 2, 3, 4, or more guanines and/or cytosines within 6 nucleotides of its 3' end. In some aspects, the nucleic acid oligonucleotide is designed to provide a G/C lock between the adjacent or overlapping target sequence in the target RNA and a complementary sequence in a primary probe, including after cleavage of the target RNA by the RNase H.

In some aspects, the nucleic acid oligonucleotide is designed such that upon hybridization of the nucleic acid oligonucleotide to the oligonucleotide hybridization region, the RNase H cleaves the target RNA at a position 5-8 nucleotides from the 3' end of the hybridized nucleic acid oligonucleotide. In some aspects, the nucleic acid oligonucleotide is designed such that upon hybridization of the nucleic acid oligonucleotide to the oligonucleotide hybridization region, the RNase H cleaves the target RNA at a position 6-7 nucleotides from the 3' end of the hybridized nucleic acid oligonucleotide.

B. RNase H

In some embodiments, the method comprises contacting the biological sample with an RNase H. Any suitable RNase H for cleaving RNA in an nucleic acid duplex (e.g., within the oligonucleotide hybridization region hybridized to the nucleic acid oligonucleotide) can be used. The RNase H enzyme and its family of enzymes include two classes, type 1 and type 2 RNase H based on the difference in their amino acid sequence. Type 1 RNases H include prokaryotic and eukaryotic RNases H1 and retroviral RNase H. Type 2 RNases H include prokaryotic and eukaryotic RNases H2 and bacterial RNase H3. These RNases H exist in a monomeric form, except for eukaryotic RNases H2, which exist in a heterotrimeric form. All of these enzymes share the characteristic that they are able to cleave the RNA component of an RNA:DNA heteroduplex or within a DNA:DNA duplex containing RNA base(s) within one or both of the strands. The cleaved product yields a free 3'-OH for both classes of RNase H. In some embodiments, RNase H1 requires more than a single RNA base within an RNA:DNA duplex for optimal activity. In some embodiments, RNase HII requires only a single RNA base in an RNA:DNA duplex.

In some embodiments, the RNase H enzyme comprises RNase H1 (commercially available from NEB, Inc.) or RNase H3. An exemplary RNase H enzyme includes E. coli RNase HII (available for example from NEB, Inc. (product M0288)). In some embodiments, the RNase is an RNase HII. In some embodiments, the RNase can be E. coli RNase H (available, for example, from NEB, Inc., for example product M0297), which also cleaves a ribo-base when hybridized to DNA and leaves a 3'-hydroxyl end. In some embodiments, the RNase H is a thermostable RNase H (available, for example, from NEB, e.g., product M0523). In some embodiments, the RNase H is a mammalian RNase H, such as any of those described in US20050164234, the content of which is herein incorporated by reference in its entirety.

An enzyme with RNase HII characteristics has been purified to near homogeneity from human placenta (Frank et al., Nucleic Acids Res., 1994, 22, 5247-5254). This protein has a molecular weight of approximately 33 kDa and is active in a pH range of 6.5-10, with a pH optimum of 8.5-9. The enzyme requires $Mg^{2+}$ and is inhibited by $Mn^{2+}$ and n-ethyl maleimide. The products of cleavage reactions have 3' hydroxyl and 5' phosphate termini. In some embodiments, the method comprises contacting the biological sample with a nucleic acid oligonucleotide, wherein the nucleic acid oligonucleotide hybridizes to an oligonucleotide hybridization region in a target ribonucleic acid (RNA); contacting the biological sample with an RNase H to cleave the target RNA in the oligonucleotide hybridization region to generate a cleaved target RNA; and incubating the biological sample with the RNase H before contacting the biological sample with a circular probe or a circularizable probe or probe set, wherein the circular probe or the circularizable probe or probe set comprises a target recognition sequence complementary to a target sequence in the target RNA. In some embodiments, the method comprises incubating the biological sample with the RNase H at a temperature below 60° C. (e.g. at room temperature or about 20-50° C., 20-30° C., 20-40° C., 25-40° C., 30-40° C., 35-40° C., or 40-50° C.). In some embodiments, the method comprises incubating the biological sample with RNase H at about 37° C. In some embodiments, the method comprises incubating the biological sample with RNase H at about 37° C. for a duration of between about 10 minutes and about 2 hours, between about 10-120, 10-90, 10-60, 10-30, 20-90, 20-60, 20-30, or 30-60 minutes. In some embodiments, the method comprises incubating the biological sample with RNase H at about 37° C. for a duration of less than 30 minutes. In some embodiments, the method comprises incubating the biological sample with RNase H at about 37° C. for a duration of about 20-35 minutes.

In some embodiments, the cleaving step is performed at a temperature below 60° C. (e.g. at room temperature or about 20-50° C., 20-30° C., 20-40° C., 25-40° C., 30-40° C., 35-40° C., or 40-50° C.). In some embodiments, the cleaving step is performed by incubating the biological sample with RNase H at about 37° C. In some embodiments, the cleaving step is performed by incubating the biological sample with RNase H at about 37° C. for a duration of between about 10 minutes and about 2 hours, between about 10-120, 10-90, 10-60, 10-30, 20-90, 20-60, 20-30, or 30-60 minutes. In some embodiments, the cleaving step is performed by incubating the biological sample with RNase H at about 37° C. for a duration of less than 30 minutes. In some embodiments, the cleaving step is performed by incubating the biological sample with RNase H at about 37° C. for a duration of about 20 minutes.

In some embodiments, the provided methods comprise contacting the biological sample with RNase H at a concentration of about at least $1\times10^{-5}$, $1\times10^{-4}$, $1\times10^{-3}$, $1\times10^{-2}$, $1\times10^{-1}$, 1 U/µL, or higher. In some embodiments, the RNase H concentration is less than 1, $1\times10^{-1}$, $1\times10^{-2}$, $1\times10^{-3}$, $1\times10^{-4}$, $1\times10^{-5}$ U/µL, or less. In some embodiments, the RNase H concentration is between about $1\times10^{-5}$ and about $1\times10^{-4}$, between about $1\times10^{-4}$ and about $1\times10^{-3}$, between about $1\times10^{-3}$ and about $1\times10^{-2}$, between about $1\times10^{-2}$ and about $1\times10^{-1}$, between about $1\times10^{-1}$ and about 1, between about $1\times10^{-1}$ and about $1\times10^{-3}$, between about $1\times10^{-4}$ and about $1\times10^{-2}$, between about $1\times10^{-3}$ and about $1\times10^{-1}$ U/µL, or between about $1\times10^{-2}$ and about 1 U/µL. In some embodiments, the RNase H concentration is about $1\times10^{-4}$, $3\times10^{-4}$, $1\times10^{-3}$, $3\times10^{-3}$, $1\times10^{-2}$, $3\times10^{-2}$, or $1\times10^{-1}$ U/µL. In some embodiments, the RNase H concentration is about $1\times10^{-2}$, $3\times10^{-2}$, or $1\times10^{-1}$ U/µL. In some embodiments, the RNase H concentration is about $1\times10^{-2}$ U/µL.

In some embodiments, the provided methods comprise contacting the biological sample with between about 0.5 enzyme units (U) and about 100 U of the RNase H. In some embodiments, the biological sample is contacted with between about 0.5 and about 100, between about 0.5 and about 80, between about 0.5 and about 60, between about 0.5 and about 50, between about 0.5 and about 40, between about 0.5 and about 30, between about 0.5 and about 20, between about 0.5 and about 10, between about 0.5 and about 8, between about 0.5 and about 5, between about 0.5 and about 5, between about 0.5 and about 3, between about 2 and about 10, between about 2 and about 8, between about 2 and about 6, between about 2 and about 5, between about 2 and about 4, between about 3 and about 8, between about 3 and about 6, between about 4 and about 8, between about 4 and about 6, between about 4 and about 5.5, between about 4.5 and about 5.5, between about 4.5 and about 6, between about 10 and about 100, between about 10 and about 50, between about 10 and about 30, between about 10 and about 20, between about 20 and about 100, between about 20 and about 50, between about 20 and about 40, between about 20 and about 30, between about 30 and about 100, between about 30 and about 80, or between about 30 and about 50 U of RNase H. In some embodiments, the amount of RNase H contacted with the biological sample is dependent on the amount of nucleic acid oligonucleotide to be cleaved in the biological sample.

In some embodiments, the RNase H is incubated with the biological sample in a buffer comprising magnesium chloride. In some embodiments, the RNase H is incubated with the biological sample in a buffer comprising magnesium chloride, potassium chloride, dithiothreitol (DTT), and a buffering agent (e.g., Tris-HCL).

In some embodiments, the RNase H comprises an RNase H1 and/or an RNase H2. In some embodiments, the method comprises contacting the biological sample with an RNase H1 and an RNase H2.

In some embodiments, the RNase H is RNase H1. In some embodiments, the RNase H is an endoribonuclease that specifically hydrolyzes the phosphodiester bonds of RNA which is hybridized to DNA. In some embodiments, the RNase H does not digest single or double-stranded DNA. In some embodiments, the RNase H requires at least four contiguous bases of RNA for digestion of the RNA hybridized to DNA. In some embodiments, the RNase H does not digest a di-ribonucleotide-containing DNA sequence (e.g., one that is DNA-annealed). In some embodiments, the RNase H does not digest a mono-ribonucleotide-containing DNA sequence (e.g., one that is DNA-annealed). In some embodiments, the RNase H digests a target RNA but does not digest a circular or circularizable probe (e.g., a DNA probe or a probe comprising one or more RNA bases on a DNA backbone) hybridized to the target RNA, such that the digested target RNA can function as an RCA primer using the circular or circularized probe (generated from the circularizable probe) as an RCA template.

In some embodiments, the RNase H is RNase H2. In some embodiments, the RNase H is an endoribonuclease that preferentially nicks 5' to one or more ribonucleotides (e.g., a single ribonucleotide, a diribonucleotide sequence, etc.) within the context of a DNA duplex, leaving 5' phosphate and 3' hydroxyl ends. In some embodiments, the RNase H nicks at multiple sites along an RNA portion hybridized to a DNA. In some embodiments, the RNase H digests a DNA-annealed di-ribonucleotide-containing DNA sequence, whereas the RNA-annealed di-ribonucleotide-containing DNA sequence is not digested. In some embodiments, the RNase H digests a DNA-annealed mono-ribonucleotide-containing DNA sequence, whereas RNA-annealed mono-ribonucleotide-containing DNA sequence is not digested. In some embodiments, the RNase H digests a target RNA but does not digest a circular or circularizable probe (e.g., a DNA probe or a probe comprising one or more RNA bases on a DNA backbone) hybridized to the target RNA, such that the digested target RNA can function as an RCA primer using the circular or circularized probe (generated from the circularizable probe) as an RCA template.

In some embodiments, the RNase H cleaves RNA in RNA-DNA duplexes. In some embodiments, the RNase H is a bacterial RNase H or analog or derivative thereof (e.g., *Escherichia coli* RNase H or an analog or derivative thereof). In some embodiments, the RNase H is a eukaryotic RNase H or analog or derivative thereof (e.g., human RNase H or an analog or derivative thereof). In some embodiments, the RNase H is a viral RNase H or analog or derivative thereof, such as an HIV-derived RNase H. RNase H sequence preferences are described, for example, in Kielpinski et al., "RNase H sequence preferences influence antisense oligonucleotide efficiency." *Nucleic Acids Res.* 2017 Dec. 15; 45(22):12932-12944, the content of which is herein incorporated by reference in its entirety.

In some embodiments, the RNase H exhibits a sequence preference for cleavage, and the oligonucleotide hybridization region is designed to contain a preferred sequence motif for RNase H cleavage. In some embodiments, the oligonucleotide hybridization region comprises an AA or AU sequence, wherein the AA or AU sequence is 1, 2, 3, 4, 5, or 6 nucleotides downstream of a cytosine or a guanine. In some embodiments, the oligonucleotide hybridization region comprises a sequence of at least 2, 3, 4, or more cytosines and/or guanines beginning at a position 2, 3, 4, 5, or 6 nucleotides upstream of the AA or AU sequence. In some embodiments, the oligonucleotide hybridization region comprises a CAAG sequence. In some embodiments, the oligonucleotide hybridization region is about 10 to about 20 nucleotides in length, or about 15 to about 20 nucleotides in length. In some embodiments, the nucleotide sequence 5' and adjacent to the oligonucleotide hybridization region comprises a sequence of 1, 2, 3, 4, or more guanines and/or cytosines. In some embodiments, the oligonucleotide hybridization region comprises 1, 2, 3, 4, or more guanines and/or cytosines within 5, 6, 7, or 8 nucleotides of its 3' end.

C. Nucleic Acid Probes

Disclosed herein in some aspects are nucleic acid probes and/or probe sets (e.g., circular probes or circularizable probes or probe sets) that are introduced into a cell or used to otherwise contact a biological sample such as a tissue sample. The probes may comprise any of a variety of entities that can hybridize to a nucleic acid, typically by Watson-Crick base pairing, such as DNA, RNA, LNA, PNA, etc. The nucleic acid probe typically contains a sequence (e.g., hybridization region such as a target recognition sequence) that can directly or indirectly bind to at least a portion of a target nucleic acid. The nucleic acid probe or probe set may be able to bind to a specific target nucleic acid (e.g., an mRNA, or other nucleic acids as discussed herein). In some embodiments, RCA products of the circular probes or circularized probes generated from the circularizable probes or probe sets are detected using a detectable label, and/or by using secondary nucleic acid probes able to bind to the RCA products or sequences thereof.

In some aspects, some biological samples (e.g., FFPE) or processing of biological samples may result in RNAs with 3' phosphates being present in the biological sample. In some embodiments, the method comprises a phosphatase treatment to repair RNA and provide 3' OH groups (e.g., for phi29 to initiate polymerization). In some embodiments, the biological sample is treated to repair 3' RNA ends (e.g., after incubating the sample with the RNase H). In some aspects, the biological sample comprises nucleic acids damaged from chemical degradation. In some embodiments, the method comprises incubating the biological sample with a polynucleotide kinase (e.g., T4 PNK) and a nucleotide triphosphate (e.g., ATP) prior to hybridizing a nucleic acid probe (e.g., a circular or circularizable probe). In some embodiments, the method comprises incubating the biological sample with a polynucleotide kinase (e.g., T4 PNK) in a buffer that does not comprise nucleotide triphosphate (e.g., ATP) prior to hybridizing a nucleic acid probe (e.g., a circular or circularizable probe). In some embodiments, the method comprises incubating the biological sample with a polynucleotide kinase (e.g., T4 PNK) in a buffer that does not comprise nucleotide triphosphate (e.g., ATP) at a pH between about 6 and about 7 (e.g., about pH 6.5) prior to hybridizing a nucleic acid probe (e.g., a circular or circularizable probe). In some aspects, the biological sample comprises nucleic acids with 2'3' cyclic phosphate, which can also be repaired by a phosphatase treatment (e.g., T4 PNK). In some cases, the repair comprises a plurality of DNA damage repair treatments (e.g., abasic regions or oxidized bases).

In some embodiments, before step (a), the method further comprises converting the 5' end group of least one RNA in the biological sample into a 5'-phosphate group. In some embodiments, the method further comprises reacting at least one RNA in the biological sample with a polynucleotide kinase to provide the RNA comprising a 5'-phosphate group. In some embodiments, the polynucleotide kinase comprises a T4 Polynucleotide Kinase (T4 PNK). In some embodiments, the polynucleotide kinase comprises a T7 Polynucleotide Kinase (T7-PNK). In some embodiments, the polynucleotide kinase is a T4 PNK or a T7-PNK. In some embodiments, the polynucleotide kinase is T4 PNK. In some embodiments, the polynucleotide kinase is T7 PNK. In some embodiments, the biological sample is a formalin-fixed paraffin-embedded (FFPE) tissue section. In some embodiments, the biological sample comprises fragmented RNA. In some embodiments, the method comprises converting the 5' end groups (e.g., 5'-OH of fragmented RNAs) of least a plurality of RNAs in the biological sample into 5'-phosphate groups. In some embodiments, the biological sample is incubated with T4 PNK enzyme at 0.5 U/μL for 1 hour at 37° C. In some embodiments, the biological sample is incubated with the polynucleotide kinase at a pH between about 6 and about 8, between about 6 and about 7, or between about 7 and about 8. In some embodiments, the biological sample is incubated with the polynucleotide kinase at a pH of about 6.5

In some embodiments, the PNK is contacted with the biological sample in the presence of magnesium. In some embodiments, the PNK comprises the N-terminal Pnk domain of T4 PNK. In some embodiments, the PNK is a T4 PNK or a homolog thereof. In some embodiments, the PNK is a T7 PNK or a homolog thereof. In some embodiments, the PNK is a *Runella slithyformis* HD-Pnk or a homolog thereof.

In some embodiments, the provided methods comprise incubating the biological sample with T4 PNK at a concentration of about at least 0.05 U/μL, 0.1 U/μL, 0.3 U/μL, 0.5 U/μL, 0.7 U/μL, 0.9 U/μL, or higher. In some embodiments, the T4 PNK concentration is less than 5 U/μL. In some embodiments, the T4 PNK concentration is less than 1 U/μL. In some embodiments, the T4 PNK concentration is between about 0.05 U/μL and about 5 U/μL, between about 0.1 U/μL and about 5 U/μL, between about 0.1 U/μL and about 1 U/μL, between about 0.3 U/μL and about 2 U/μL, between about 0.3 U/μL and about 1 U/μL, or between about 0.3 U/μL and about 0.8 U/μL. In some embodiments, the T4 PNK concentration is about 0.05 U/μL, 0.1 U/μL, 0.3 U/μL, 0.5 U/μL, or 1 U/μL. In some embodiments, the biological sample is incubated with 0.5 U/μL T4 PNK enzyme. In some embodiments, the biological sample is contacted with the PNK and between any one of about 0.1-10, 0.5-5, 0.5-2, 0.7-1, or 1-2 mM nucleoside triphosphate (e.g., ATP). In some embodiments, the biological sample is contacted with the PNK in a buffer that does not have nucleoside triphosphate (e.g., ATP).

In some embodiments, more than one type of primary nucleic acid probes are contacted with a sample. In some embodiments, the primary probes comprise circular probes and/or circularizable probes (such as padlock probes) or circularizable probe sets. In some embodiments, more than one type of secondary nucleic acid probes may be contacted with a sample, e.g., simultaneously or sequentially in any suitable order, such as in sequential probe hybridization/unhybridization cycles. In some embodiments, the secondary probes may comprise probes that bind to a product (e.g., an RCA product) of a primary probe targeting an analyte (e.g., an RNA molecule). In some embodiments, more than one type of higher order nucleic acid probes may be contacted with a sample, e.g., simultaneously or sequentially in any suitable order, such as in sequential probe hybridization/unhybridization cycles. In some embodiments, more than one type of detectably labeled nucleic acid probes may be contacted with a sample, e.g., simultaneously or sequentially in any suitable order, such as in sequential probe hybridization/unhybridization cycles. In some embodiments, the detectably labeled probes may comprise probes that bind to one or more primary probes, one or more secondary probes, one or more higher order probes, one or more intermediate probes between a primary/second/higher order probes, and/or one or more detectably or non-detectably labeled probes. In some embodiments, at least 2, at least 5, at least 10, at least 25, at least 50, at least 75, at least 100, at least 300, at least 1,000, at least 3,000, at least 10,000, at least 30,000, at least 50,000, at least 100,000, at least 250,000, at least 500,000, or at least 1,000,000 distinguishable nucleic acid probes (e.g., primary, secondary, higher order probes, and/or detectably labeled probes) are contacted with a sample, e.g., simultaneously or sequentially in any suitable order. In some embodiments, at least 500, at least 1,000, at least 2,000, at least 3,000 distinguishable nucleic acid probes (e.g., primary circular or circularizable probes) are contacted with a sample. In some embodiments, a plurality of distinguishable nucleic acid probes may be complementary to different sequences of the same target RNA. For example, at least 2, 3, 4, 5, 6, 7, 8, 9, or 10 distinguishable nucleic acid probes may each have different target recognition sequences complementary to non-overlapping target sequences of the same target RNA.

Between any of the probe contacting steps disclosed herein, the method may comprise one or more intervening reactions and/or processing steps, such as modifications of a target nucleic acid, modifications of a probe or product thereof (e.g., via hybridization, ligation, extension, amplification, cleavage, digestion, branch migration, primer exchange reaction, click chemistry reaction, crosslinking, attachment of a detectable label, activating photo-reactive moieties, etc.), removal of a probe or product thereof (e.g., cleaving off a portion of a probe and/or unhybridizing the entire probe), signal modifications (e.g., quenching, masking, photo-bleaching, signal enhancement (e.g., via FRET), signal amplification, etc.), signal removal (e.g., cleaving off or permanently inactivating a detectable label), crosslinking, de-crosslinking, and/or signal detection.

The target recognition sequence (e.g., hybridization region) of a probe may be positioned anywhere within the probe. For instance, the target recognition sequence of a primary probe such as a circularizable probe that binds to a target nucleic acid can be 5' or 3' to any barcode sequence in the primary probe. Likewise, the target recognition sequence of a secondary probe (which binds to an RCA product of a circular or circularized primary probe) can be 5' or 3' to any barcode sequence in the secondary probe. In some embodiments, the target recognition sequence comprises a sequence that is substantially complementary to a portion of a target nucleic acid (a target sequence). In some embodiments, the target recognition sequence and the target sequence are at least 50%, at least 60%, at least 70%, at least 75%, at least 80%, at least 85%, at least 90%, at least 92%, at least 94%, at least 95%, at least 96%, at least 97%, at least 98%, at least 99%, or 100% complementary.

The target recognition sequence of a primary nucleic acid probe may be designed with reference to a target nucleic acid (e.g., a cellular RNA such as an mRNA) that is present or suspected of being present in a sample. In some embodiments, more than one target recognition sequence is used to identify a particular target RNA. The more than one target-binding sequence can be in the same probe or in different probes. For instance, multiple probes can be used, sequentially and/or simultaneously, that can bind to (e.g., hybridize to) different regions of the same target RNA. In some embodiments, a single RCA product is associated with a particular target RNA (e.g., by providing a panel of circular probes or circularizable probes or probe sets, wherein each probe or probe set is designed to hybridize to a different target RNA in the biological sample).

In some embodiments, a circular probe is a probe that is pre-circularized prior to hybridization to a target RNA. In some embodiments, a circularizable probe is a probe that is circularized upon hybridization to a target RNA and/or one or more other probes such as a splint. In some embodiments, a circularizable probe set comprises at least a first nucleic acid probe and a second nucleic acid probe that is circularized upon hybridization to a target RNA and another probe such as a splint (e.g., the first and second nucleic acid probes are ligated to each other, optionally using the target RNA and a separate nucleic acid splint to form a circularized probe).

In some embodiments, the method comprises detecting the RCA product by hybridizing one or more linear probes to the RCA product. In some embodiments, a linear probe is one that comprises a target recognition sequence (e.g., a sequence complementary to a barcode sequence or subunit thereof in the RCA product) and a sequence that does not hybridize to a target nucleic acid, such as a 5' overhang, a 3' overhang, and/or a linker or spacer (which may comprise a nucleic acid sequence or a non-nucleic acid moiety). In some embodiments, the sequence (e.g., the 5' overhang, 3' overhang, and/or linker or spacer) is non-hybridizing to the target nucleic acid but may hybridize to one another and/or one or more other probes, such as detectably labeled probes. In some embodiments, a linear probe is one that comprises a target recognition sequence (e.g., a sequence complementary to a barcode sequence or subunit thereof in the RCA product) and an optically detectable label.

In some embodiments, the circularizable probe or probe set comprises one, two, three, four, or more ribonucleotides. In some embodiments, a circularizable probe or probe set disclosed herein can comprise one, two, three, four, or more ribonucleotides in a DNA backbone. In any of the embodiments herein, the one or more ribonucleotides can be at and/or near a ligatable 3' end of the circularizable probe or probe set. In some embodiments, a circularizable probe disclosed herein can comprise one, two, three, four, or more ribonucleotides in a DNA backbone, wherein the one or more ribonucleotides are at a ligatable 3' end of the circularizable probe (e.g., a ligatable 3' end in a target recognition sequence of the circularizable probe, wherein the ligatable 3' end can be ligated to a ligatable 5' end in a target recognition sequence of the circularizable probe to generate a circularized probe). In some embodiments, a 3' terminal nucleotide of the circularizable probe hybridized to the target RNA is a ribonucleotide. In some embodiments, a 3' terminal nucleotide of the circularizable probe set hybridized to the target RNA is a ribonucleotide. In some embodiments, a 3' end and a 5' end of the circularizable probe or probe set are ligated using the target RNA as a template.

In some embodiments, a probe disclosed herein (e.g., circularizable probe or probe set) comprises a 5' flap which may be recognized by a structure-specific cleavage enzyme, e.g., an enzyme capable of recognizing the junction between single-stranded 5' overhang and a DNA duplex, and cleaving the single-stranded overhang. It will be understood that the branched three-strand structure which is the substrate for the structure-specific cleavage enzyme may be formed by 5' end of one probe part and the 3' end of another probe part when both have hybridized to the target nucleic acid molecule, as well as by the 5' and 3' ends of a one-part probe. Enzymes suitable for such cleavage include Flap endonucleases (FENS), which are a class of enzymes having endonucleolytic activity and being capable of catalyzing the hydrolytic cleavage of the phosphodiester bond at the junction of single- and double-stranded DNA. Thus, in some embodiment, cleavage of the additional sequence 5' to the first target-specific binding site is performed by a structure-specific cleavage enzyme, e.g., a Flap endonuclease. Suitable Flap endonucleases are described in Ma et al. 2000. *JBC* 275, 24693-24700 and in US 2020/0224244 (herein incorporated by reference in their entireties) may include *P. furiosus* (Pfu), *A. fulgidus* (Afu), *M. jannaschii* (Mja) or *M. thermoautotrophicum* (Mth). In other embodiments an enzyme capable of recognizing and degrading a single-stranded oligonucleotide having a free 5' end may be used to cleave an additional sequence (5' flap) from a structure as described above. Thus, an enzyme having 5' nuclease activity may be used to cleave a 5' additional sequence. Such 5' nuclease activity may be 5' exonuclease and/or 5' endonuclease activity. A 5' nuclease enzyme is capable of recognizing a free 5' end of a single-stranded oligonucleotide and degrading said single-stranded oligonucleotide. A 5' exonuclease degrades a single-stranded oligonucleotide having a free 5' end by degrading the oligonucleotide into constituent mononucleotides from its 5' end. A 5' endonuclease activity may cleave the 5' flap sequence internally at one or more nucleotides. Further, a 5' nuclease activity may take place by the enzyme traversing the single-stranded oligonucleotide to a region of duplex once it has recognized the free 5' end, and cleaving the single-stranded region into larger constituent nucleotides (e.g., dinucleotides or trinucleotides), or cleaving the entire 5' single-stranded region, e.g., as described in Lyamichev et al. 1999. *PNAS* 96, 6143-6148 for Taq DNA polymerase and the 5' nuclease thereof. Preferred enzymes having 5' nuclease activity include Exonuclease VIII, or a native or recombinant DNA polymerase enzyme from *Thermus aquaticus* (Taq), *Thermus thermophilus* or *Thermus flavus*, or the nuclease domain therefrom.

Any suitable circularizable probe or probe set may be used to generate the RCA template which is used to generate the RCA product. In some embodiments, a circularizable probe is in the form of a linear molecule having ligatable ends which may be circularized by ligating the ends together directly or indirectly, e.g., to each other, or to the respective ends of an intervening ("gap") oligonucleotide or to an extended 3' end of the circularizable probe. A circularizable probe may also be provided in two or more parts, namely two or more molecules (e.g., oligonucleotides) which may be ligated together to form a circle. When said RCA template is circularizable it is circularized by ligation prior to RCA. Ligation may be templated using a ligation template, and in the case of padlock and molecular inversion probes and such like the target analyte may provide the ligation template, or it may be separately provided. The circularizable RCA template (or template part or portion) will comprise at its respective 3' and 5' ends regions of complementarity to corresponding cognate complementary regions (or binding sites) in the ligation template, which may be adjacent where the ends are directly ligated to each other, or non-adjacent, with an intervening "gap" sequence, where indirect ligation is to take place.

In some embodiments (e.g., wherein the circularizable probe is a padlock probe) the ends of the circularizable probe are brought into proximity to each other by hybridization to adjacent sequences on a target nucleic acid molecule (such as a target analyte), which acts as a ligation template, thus allowing the ends to be ligated together to form a circular nucleic acid molecule, allowing the circularized circularizable probe to act as template for an RCA reaction. In such an example the terminal sequences of the circularizable probe which hybridize to the target nucleic acid molecule will be specific to the target analyte in question, and will be replicated repeatedly in the RCA product. They may therefore act as a marker sequence indicative of that target analyte. Accordingly, it can be seen that the marker sequence in the RCA product may be equivalent to a sequence present in the target analyte itself. Alternatively, a marker sequence (e.g., tag or barcode sequence) may be provided in the non-target complementary parts of the circularizable probe. In still a further embodiment, the marker sequence may be present in the gap oligonucleotide which is hybridized between the respective hybridized ends of the circularizable probe, where they are hybridized to non-adjacent sequences in the target molecule. Such gap-filling padlock probes are akin to molecular inversion probes.

In some embodiments, similar circular RCA template molecules can be generated using molecular inversion probes. Like padlock probes, these are also typically linear nucleic acid molecules capable of hybridizing to a target nucleic acid molecule (such as a target analyte) and being circularized. The two ends of the molecular inversion probe may hybridize to the target nucleic acid molecule at sites which are proximate but not directly adjacent to each other, resulting in a gap between the two ends. The size of this gap may range from only a single nucleotide in some embodiments, to larger gaps of 100 to 500 nucleotides, or longer, in other embodiments. Accordingly, it is necessary to supply a polymerase and a source of nucleotides, or an additional gap-filling oligonucleotide, in order to fill the gap between the two ends of the molecular inversion probe, such that it can be circularized.

As with the circularizable probe, the terminal sequences of the molecular inversion probe which hybridize to the target nucleic acid molecule, and the sequence between them, will be specific to the target analyte in question, and will be replicated repeatedly in the RCA product. They may therefore act as a marker sequence indicative of that target analyte. Alternatively, a marker sequence (e.g., tag or barcode sequence) may be provided in the non-target complementary parts of the molecular inversion probe.

In some embodiments, the probes disclosed herein may be invader probes, e.g., for generating a circular nucleic acid such as a circularized probe. Such probes are of particular utility in the detection of single nucleotide polymorphisms. The detection method of the present disclosure may, therefore, be used in the detection of a single nucleotide polymorphism, or indeed any variant base, in the target nucleic acid sequence. Probes for use in such a method may be designed such that the 3' ligatable end of the probe is complementary to and capable of hybridizing to the nucleotide in the target molecule which is of interest (the variant nucleotide), and the nucleotide at the 3' end of the 5' additional sequence at the 5' end of the probe or at the 5' end of another, different, probe part is complementary to the same said nucleotide, but is prevented from hybridizing thereto by a 3' ligatable end (e.g., it is a displaced nucleotide). Cleavage of the probe to remove the additional sequence provides a 5' ligatable end, which may be ligated to the 3' ligatable end of the probe or probe part if the 3' ligatable end is hybridized correctly to (e.g. is complementary to) the target nucleic acid molecule. Probes designed according to this principle provide a high degree of discrimination between different variants at the position of interest, as only probes in which the 3' ligatable end is complementary to the nucleotide at the position of interest may participate in a ligation reaction. In one embodiment, the probe is provided in a single part, and the 3' and 5' ligatable ends are provided by the same probe. In some embodiments, an invader probe is a padlock probe (an invader padlock or "iLock"), e.g., as described in Krzywkowski et al., *Nucleic Acids Research* 45, e161, 2017, and US 2020/0224244, which are incorporated herein by reference in their entirety.

Other types of probe which result in circular molecules which can be detected by RCA and which comprise either a target analyte sequence or a complement thereof include selector-type probes described in US 2019/0144940 (herein incorporated by reference in its entirety), which comprise sequences capable of directing the cleavage of a target nucleic acid molecule (e.g. a target analyte) so as to release a fragment comprising a target sequence from the target analyte and sequences capable of templating the circularization and ligation of the fragment. US 2018/0327818, the content of which is herein incorporated by reference in its entirety, describes probes which comprise a 3' sequence capable of hybridizing to a target nucleic acid molecule (e.g. a target analyte) and acting as a primer for the production of a complement of a target sequence within the target nucleic acid molecule (e.g. by target templated extension of the primer), and an internal sequence capable of templating the circularization and ligation of the extended probe comprising the reverse complement of the target sequence within the target analyte and a portion of the probe. In the case of both such probes, target sequences or complements thereof are incorporated into a circularized molecule which acts as the template for the RCA reaction to generate the RCA product, which consequently comprises concatenated repeats of said target sequence. In some embodiments, said target sequence may act as, or may comprise a marker sequence within the RCA product indicative of the target analyte in question. Alternatively, a marker sequence (e.g., tag or barcode sequence) may be provided in the non-target complementary parts of the probes.

In some embodiments, a nucleic acid probe disclosed herein can be pre-assembled from multiple components, e.g., prior to contacting the nucleic acid probe with a target nucleic acid or a sample. In some embodiments, a nucleic acid probe disclosed herein can be assembled during and/or after contacting a target nucleic acid or a sample with multiple components. In some embodiments, a nucleic acid probe disclosed herein is assembled in situ in a sample. In some embodiments, the multiple components can be contacted with a target nucleic acid or a sample in any suitable order and any suitable combination. For instance, a first component and a second component can be contacted with a target nucleic acid, to allow binding between the components and/or binding between the first and/or second components with the target nucleic acid. Optionally a reaction involving either or both components and/or the target nucleic acid, between the components, and/or between either one or both components and the target nucleic acid can be performed, such as hybridization, ligation, primer extension and/or amplification, chemical or enzymatic cleavage, click chemistry, or any combination thereof. In some embodiments, a third component is added prior to, during, or after the reaction. In some embodiments, a third component is added prior to, during, or after contacting the sample with the first and/or second components. In some embodiments, the first, second, and third components are contacted with the sample in any suitable combination, sequentially or simultaneously. In some embodiments, the nucleic acid probe can be assembled in situ in a stepwise manner, each step with the addition of one or more components, or in a dynamic process where all components are assembled together. One or more removing steps, e.g., by washing the sample such as under stringent conditions, may be performed at any point during the assembling process to remove or destabilize undesired intermediates and/or components at that point and increase the chance of accurate probe assembly and specific target binding of the assembled probe.

In some embodiments, a nucleic acid probe disclosed herein is pre-assembled from multiple components, e.g., prior to contacting the nucleic acid probe with a target nucleic acid or a sample. In some embodiments, a nucleic acid probe disclosed herein is assembled in vitro prior to contacting with the sample. For example, a circular probe disclosed herein can be ligated and purified prior to contacting with the sample. In some embodiments, the 3' and 5' ends of a linear nucleic acid molecule are ligated to form a circular probe (e.g., using a nucleic acid splint that hybridizes to sequences at the 3' and 5' ends of a linear nucleic acid molecule). In some embodiments, a common splint is used to ligate a plurality of different linear nucleic acid molecules to generate a plurality of different circular probes for different target RNAs. In some embodiments, different linear nucleic acid molecules hybridize to a corresponding different splint for ligation. In some embodiments, the 3' and 5' ends of a linear nucleic acid molecule are ligated to form a circular probe without the use of a splint. In some embodiments, to generate a plurality of different circular probes for different target RNAs, the different circular probes are generated separately (e.g., in individual reactions) and then purified and pooled with other circular probes targeting different target RNAs to generate a pool of circular probes prior to contacting with the sample.

In some embodiments, the hybridization conditions include salt concentrations of approximately less than 1 M, e.g. less than about 500 mM and or less than about 200 mM. In some embodiments, hybridization is performed in a hybridization buffer that includes a buffered salt solution such as 5% SSPE, or other such buffers. Hybridization temperatures can be as low as 5° C., but are typically greater than 22° C., and more typically greater than about 30° C., and typically in excess of 37° C. Hybridizations are often performed under stringent conditions, e.g., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are available. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985), the content of which is herein incorporated by reference in its entirety). Other references (e.g., Allawi and SantaLucia, Jr., Biochemistry, 36:10581-94 (1997), the content of which is herein incorporated by reference in its entirety) include alternative methods of computation which take structural and environmental, as well as sequence characteristics into account for the calculation of $T_m$. In general, the stability of a hybrid is a function of the ion concentration and temperature. Typically, a hybridization reaction is performed under conditions of lower stringency, followed by washes of varying, but higher, stringency.

In some instances, the circular or circularizable probe is hybridized to the target nucleic acid (e.g., target RNA) and ligated to form a circular template for RCA. In some embodiments, the ligation comprises RNA-templated ligation using the target RNA as a template. In some embodiments, the ligation involves chemical ligation. In some embodiments, the ligation involves template dependent ligation. In some embodiments, the ligation involves template independent ligation. In some embodiments, the ligation involves enzymatic ligation. In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase or derivative thereof. In some embodiments, the ligase is a T4 RNA ligase 2 (Rnl2) or derivative thereof. In some embodiments, the ligase is a splintR ligase. In some embodiments, the ligase is a Chlorella virus DNA Ligase (PBCV-1 DNA ligase) or derivative thereof. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity. In some embodiments, the ligase is selected from the group consisting of a Chlorella virus DNA ligase (PBCV DNA ligase), a T4 RNA ligase, a T4 DNA ligase, and a single-stranded DNA (ssDNA) ligase. In some embodiments, the DNA ligase is SplintR® ligase (also known as *Chlorella* virus DNA ligase or PBCV-1 DNA ligase), T4 DNA ligase or T4 RNA ligase 2.

In some embodiments, a circular probe, circularizable probe, or circularizable probe set disclosed herein comprises a barcode sequence or complement thereof (e.g., such that the RCA product produced using the circular probe or circularized probe as a template comprises the barcode sequence). In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide. In any of the preceding embodiments, the methods provided herein can include analyzing the barcodes by sequential hybridization and detection with a plurality of labelled probes (e.g., detection oligos).

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence (45=1024), whereas 8 nucleotide barcodes can be used to identify up to 65,536 molecular species, a number greater than the total number of distinct genes in the human genome. In some embodiments, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and U.S. Pat. Pub 20210164039, all of which are herein incorporated by reference in their entireties.

In some embodiments, the ligation involves chemical ligation (e.g., click chemistry ligation). In some embodiments, the chemical ligation involves template dependent ligation. In some embodiments, the chemical ligation involves template independent ligation. In some embodiments, the click reaction is a template-independent reaction (see, e.g., Xiong and Seela (2011), J. Org. Chem. 76(14): 5584-5597, incorporated by reference herein in its entirety). In some embodiments, the click reaction is a template-dependent reaction or template-directed reaction. In some embodiments, the template-dependent reaction is sensitive to base pair mismatches such that reaction rate is significantly higher for matched versus unmatched templates. In some embodiments, the click reaction is a nucleophilic addition template-dependent reaction. In some embodiments, the click reaction is a cyclopropane-tetrazine template-dependent reaction.

In some embodiments, the ligation involves enzymatic ligation. In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, i.e., separated by one or more intervening nucleotides or "gaps". In some embodiments, said ends are not ligated directly to each other, but instead occurs either via the intermediacy of one or more intervening (so-called "gap" or "gap-filling" (oligo)nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, padlock probe, or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some embodiments, the ligation herein is a proximity ligation of ligating two (or more) nucleic acid sequences that are in proximity with each other, e.g., through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the content of which is herein incorporated by reference in its entirety). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

The target recognition sequences may be of any length, and multiple recognition sequences in the same or different circular probes or circularizable probes or probe sets may be of the same or different lengths. For instance, the target recognition sequence may be at least 20, at least 25, at least 30, at least 35, at least 40, or at least 50 nucleotides in length. In some embodiments, the target recognition sequence may be no more than 48, no more than 45, or no more than 40 nucleotides in length. Combinations of any of these are also possible, e.g., the recognition sequence may have a length of between 25 and 40, between 30 and 45, or between 20 and 48 nucleotides, etc. In some embodiments, the target recognition sequence is be at least 95%, at least 98%, at least 99%, or at least 100% complementary to the target sequence in the target RNA.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, e.g., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, a circularizable probe or probe set (e.g., padlock probe), or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high-fidelity ligase, such as a thermostable DNA ligase (e.g., a Taq DNA ligase), is used, for example, for ligating two or more probes to form a circular probe disclosed herein. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some embodiments, a ligation herein comprises ligating two (or more) nucleic acid termini that are in proximity with each other, e.g., that are brought into proximity upon hybridization to the target RNA and/or to a separate nucleic acid molecule (e.g., a splint oligonucleotide). In some embodiments, the circularizable probe comprises a 3' end and a 5' end that are brought into proximity upon hybridization to the target RNA (e.g., as shown for the circularizable probe in FIG. 1). In some embodiments, the circularizable probe is a padlock probe. In some embodiments, the 3' end and the 5' end of the circularizable probe do not hybridize to the target RNA (e.g., the target recognition sequence is in an internal region of the circularizable probe), and the 3' end and 5' end optionally hybridize to a separate nucleic acid molecule (e.g., a splint oligonucleotide) to bring the ends in proximity for ligation. In some embodiments, the ligation is with a ligase. In some embodiments, ligation includes a gap-filling step that involves incorporation of one or more nucleic acids by a polymerase, based on the nucleic acid sequence of a template nucleic acid molecule (e.g., a nucleic acid molecule such as a DNA splint).

D. Target RNA-Primed Rolling Circle Amplification

In some embodiments, the rolling circle amplification is performed in a buffer comprising a crowding agent. In some embodiments, the crowding agent is selected from the group consisting of poly(ethylene glycol) (PEG), glycerol, Ficoll®, and dextran sulfate. In any of the preceding embodiments, the crowding agent can be poly(ethylene glycol) (PEG). In some embodiments, the PEG is selected from the group consisting of PEG200, PEG8000, and PEG35000. In any of the preceding embodiments, the buffer may comprise between about 5% and about 15% PEG, optionally wherein the buffer comprises about 10% PEG. In some embodiments, the rolling circle amplification is performed in a buffer comprising PEG (e.g., from about PEG 2K to about PEG 16K). In some embodiments, the PEG is PEG 2K, 3K, 4K, 5K, 6K, 7K, 8K, 9K, 10K, 11K, 12K, 13K, 14K, 15K, or 16K. In some embodiments, the PEG is present at a concentration from about 2% to 25%, from about 4% to about 23%, from about 6% to about 21%, or from about 8% to about 20% (v/v). In some aspects, the crowding agent can be used to stabilize the nucleic acid probes (e.g., circular or circularizable probes) and/or amplification product in a location in the biological sample.

The methods for target-primed RCA provided herein can be used to detect and/or analyze one or more target RNAs (e.g., nucleic acid analytes). Examples of nucleic acid analytes include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaR-NAs), and the long ncRNAs such as Xist and HOTAIR. The RNA can be small (e.g., less than 200 nucleic acid bases in length) or large (e.g., RNA greater than 200 nucleic acid bases in length). The RNA can be circular RNA. In some embodiments, the RNA comprises one or more secondary structures. In some embodiments, the RNA is single-stranded.

Methods and compositions disclosed herein can be used to analyze any number of target RNAs. For example, the number of target RNAs that are analyzed using the target-primed RCA methods disclosed herein can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000 or more different target RNAs present in a region of the biological sample. In some instances, the number of target RNAs that are analyzed using the target-primed RCA methods disclosed herein is at least about 100, at least about 500, at least about 1,000, at least about 10,000 or more different target RNAs present in a region of the biological sample.

In some instances, amplification of probes bound to a subset of target RNAs in the biological sample are primed using the target RNA while amplification of an additional subset of target RNAs are primed with an exogenous primer. In some instances, the exogenous primer binds to a sequence in the arm(s) of the circularizable probe or probe set (e.g., padlock probe). In some cases, the additional subset of target RNAs are short in length and are amplified with the exogenous primer.

In any embodiment described herein, the target RNA (e.g., target RNA analyte such as an mRNA) comprises a target sequence for a circular or circularizable probe or probe set. In some embodiments, the target sequence is endogenous to the sample. In some embodiments, the target sequence is a single-stranded target sequence in the target RNA. In some embodiments, the target sequence uniquely identifies the target RNA among the target RNAs present in the biological sample, or among the target RNAs detectably expressed in the biological sample. In some embodiments, the target sequence uniquely identifies the gene encoding the target RNA among the detectably expressed genes in the biological sample. In some embodiments, a target RNA or each target RNA comprises a single target sequence. In some embodiments, a first target RNA comprises a first target sequence, a second target RNA comprises a second target sequence, and an Nth target RNA comprises an Nth target sequence, wherein the first, second, and Nth target sequence are different.

In some embodiments the target RNA(s) is/are attached directly or indirectly to the biological sample or to a matrix embedding the biological sample. In some embodiments, the target RNA(s) is/are crosslinked in the biological sample or in a matrix embedding the biological sample. In some embodiments, the RCP is covalently linked to the cleaved target RNA or a portion thereof. For example, priming of the RCA by the cleaved target RNA results in formation of an RCP comprising the cleaved target RNA or a portion thereof covalently attached to the RCP. In some embodiments, the analytes (e.g., target RNAs), probes and/or amplification products (e.g., RCPs) described herein are anchored to a polymer matrix (e.g., as described in Section IV). For example, the polymer matrix can be a hydrogel. In some embodiments, cross-linking of the matrix or components to be anchored to the matrix are performed chemically and/or photochemically, or alternatively by any other suitable hydrogel-formation method.

In some embodiments, performing the rolling circle amplification comprises incubating the biological sample with a polymerase for a duration of between about 10 minutes and about 4 hours, between about 10-120, 30-120, 20-90, 60-90, 30-90, 30-60, 60-120, or 60-135 minutes. In some embodiments, performing the RCA comprises incubating the biological sample at a temperature between about 20° C. and about 60° C. In some embodiments, performing the rolling circle amplification comprises incubating the biological sample with a polymerase for about 30 minutes at about 30-40° C. (e.g., at about 37° C.). In some embodiments, performing the rolling circle amplification comprises incubating the biological sample with a polymerase for about 1 hour at about 30-40° C. (e.g., at about 37° C.). In some embodiments, performing the rolling circle amplification comprises incubating the biological sample with a polymerase for about 2 hours minutes at about 30-40° C. (e.g., at about 37° C.). In some embodiments, performing the rolling circle amplification comprises incubating the biological sample with a polymerase for about 30 minutes at about 40-50° C. (e.g., at about 45° C.). In some embodiments, performing the rolling circle amplification comprises incubating the biological sample with a polymerase for about 1 hour at about 40-50° C. (e.g., at about 45° C.).

In some embodiments, the polymerase is a Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, or a variant or derivative of any of the foregoing polymerases. In some embodiments, the polymerase is a Phi29 polymerase.

In some embodiments, the RCA is synchronized by synchronizing polymerase activity. In various embodiments, the method comprises contacting the biological sample with the polymerase in a first reaction mixture that reduces or inhibits polymerase activity, and then contacting the sample with a second reaction mixture that allows polymerase activity. For example, in some instances the first reaction mixture comprises $Ca^{2+}$. In some embodiments, the second reaction mixture comprises $Mg^{2+}$. In some embodiments, the synchronization of polymerase activity leads to more homogeneously sized RCPs and/or brighter RCP signal spots. In some embodiments, an increase in RCP homogeneity leads to a reduction in amplification time. Overall, the synchronization of polymerase activity can improve RCP detection during in situ analysis of a biological sample.

In some embodiments, the method comprises contacting the biological sample with a polymerase in a first reaction mixture comprising a di-cation that is not a co-factor of the polymerase or a di-cation that is a non-catalytic cofactor of the polymerase, and then contacting the biological sample with a second reaction mixture comprising a cofactor (e.g., catalytic cofactor) of the polymerase to perform the rolling circle amplification. In some embodiments, the di-cation that is not a catalytic co-factor of the polymerase is $Ca^{2+}$. In some embodiments, the second reaction mixture does not provide additional polymerase. In some embodiments, the di-cation that is not a catalytic co-factor of the polymerase stabilizes the polymerase, thereby inhibiting the polymerase activity and/or an exonuclease activity of the polymerase. In some cases, the first reaction mixture is substantially free of a catalytic cofactor of the polymerase, optionally wherein the catalytic cofactor is selected from the group consisting of $Mg^{2+}$, $Co^{2+}$, and $Mn^{2+}$. In some embodiments, the first reaction mixture comprises a chelating agent. Exemplary chelating agents include but are not limited to EDTA, EGTA, BAPTA, DTPA, and combinations thereof. In some embodiments, the second reaction mixture comprises deoxynucleotide triphosphates (dNTPs) and/or nucleotide triphosphates (NTPs). In some embodiments, the second reaction mixture comprises a catalytic cofactor of the polymerase. In some cases, the second reaction mixture is substantially free of additional polymerase. In some cases, additional polymerase is not provided to the biological sample after contacting the biological sample with a polymerase in a first reaction mixture. Exemplary polymerase cofactors include di-cations such as $Mg^{2+}$, $Co^{2+}$, and $Mn^{2+}$. In some embodiments, the cofactor of the polymerase is $Mg^{2+}$.

In some embodiments, the first reaction mixture (e.g., "OFF" buffer) comprises one or more cofactors that interact with a polymerase, but that do not promote the polymerization reaction, and in some cases act to arrest or prevent polymerization and/or inhibit one or more other activities of the polymerase, such as the 3'→5' exonuclease activity. In some embodiments, the first reaction mixture comprises one or more non-catalytic metal ions, such as calcium, barium, strontium, iron, cobalt, nickel, tin, zinc, and europium. In some embodiments, the metals are added to the reaction mixture and/or the sample in salt form such as $Sr(OAc)_2$, $Sr(OAc)_2$, $SrCl_2$, $CoCl_2$, $SnCl_2$, $CaCl_2$, or $ZnSO_4$.

A first metal co-factor that might be deemed to be catalytic under a first set of reaction conditions or relative to second metal co-factor, may be deemed to be a non-catalytic metal under another different set of reaction conditions, or with respect to a third metal co-factor. For instance, magnesium is generally known to support DNA polymerization. However, under certain conditions, and/or relative to manganese, magnesium can operate as a non-catalytic co-factor. In some embodiments herein, a catalytic co-factor supports polymerization to a greater degree than the non-catalytic metal under the same reaction conditions. In some embodiments, the relative catalytic impact is a function of the reactant turnover rate of the polymerization complex, with catalytic metal co-factors promoting a turnover that is at least two times, more preferably at least 5 times, still more preferably, at least 10 times, and in some cases 20 times, 50 times or more than that of the non-catalytic metal co-factor under the same reaction conditions. In some embodiments, the presence of a non-catalytic metal in the polymerase complex, through binding in or around the active site, results in the inability for the synthesis reaction to proceed out of the complexed state. In particular, the presence of calcium ions can modulate both the forward progress of the polymerase reaction, as well as the reverse progress of the reaction. As a result, in the presence of calcium or other non-catalytic metals, the complexed nucleotide is effectively sequestered in the polymerase complex. The reaction is an unproductive nucleotide binding event, that is, it is unable to proceed forward to incorporation, or in reverse to the release of the unincorporated nucleotide to yield a free polymerase.

In some embodiments, the non-catalytic metal is selected from $Ca^{2+}$, $Zn^{2+}$, $Co^{2+}$, $Ni^{2+}$, $Eu^{2+}$, $Sr^{2+}$, $Ba^{2+}$, $Fe^{2+}$, $Eu^{2+}$ and mixtures thereof. In some embodiments, the non-catalytic metal is $Ca^{2+}$ or $Sr^{2+}$. In some embodiments, the catalytic metal is selected from $Mg^{2+}$, $Mn^{2+}$ and mixtures thereof, and the non-catalytic metal is selected from $Ca^{2+}$, $Zn^{2+}$, $Co^{2+}$, $Ni^{2+}$, $Eu^{2+}$, $Sr^{2+}$, $Ba^{2+}$, $Fe^{2+}$, $Eu^{2+}$ and mixtures thereof. In some embodiments, the first reaction mixture (e.g., OFF buffer) comprises one or more of $Ca^{2+}$, $Zn^{2+}$, $Co^{2+}$, $Ni^{2+}$, $Eu^{2+}$, $Sr^{2+}$, $Ba^{2+}$, $Fe^{2+}$, and $Eu^{2+}$, and is substantially free of $Mg^{2+}$ and/or $Mn^{2+}$.

In some embodiments, the method further comprises, between the contacting with the first reaction mixture and with the primer extension reaction mixture (e.g., amplification reaction mixture), a step of removing molecules of the polymerase and/or the polynucleotide that are not bound to the circular nucleic acid from the biological sample. In some embodiments, the method further comprises one or more stringency washes between the contacting steps.

In some embodiments, a reaction mixture comprising a deoxynucleoside triphosphate (dNTP) or derivative, variant, or analogue thereof is used and the primer extension reaction mixture comprises a catalytic cofactor of the polymerase. In some embodiments, the primer extension reaction mixture comprises a catalytic di-cation, such as $Mg^{2+}$ and/or $Mn^{2+}$. In some embodiments, the primer extension reaction mixture is substantially free of a non-catalytic cation, such as $Ca^{2+}$, $Zn^{2+}$, $Co^{2+}$, $Ni^{2+}$, $Eu^{2+}$, $Sr^{2+}$, $Ba^{2+}$, $Fe^{2+}$, $Eu^{2+}$ and mixtures thereof. In some embodiments, a catalytic cation in the primer extension reaction mixture can replace a non-catalytic cation in complex with the polymerase that is bound to the circular nucleic acid or the RCA primer, thus turning on the polymerase activity of the polymerase. In some embodiments, when the sample is contacted with a primer extension reaction mixture comprising a catalytic di-cation (such as $Mg^{2+}$ and/or $Mn^{2+}$), a non-catalytic cation (such as $Ca^{2+}$, $Zn^{2+}$, $Co^{2+}$, $Ni^{2+}$, $Eu^{2+}$, $Sr^{2+}$, $Ba^{2+}$, $Fe^{2+}$, and/or $Eu^{2+}$) bound to Phi29 is displaced, thereby activating the 5'→3' polymerase activity and the 3'→5' exonuclease (proofreading) activity of Phi29.

E. Detection and Analysis

In some embodiments, a method disclosed herein comprises detecting one or more target nucleic acids (e.g., target RNA) in a sample using a plurality of primary probes (e.g., circular or circularizable probes) configured to hybridize to the one or more target nucleic acids, wherein each primary probe comprises hybridization region configured to hybridize to a different target region in the corresponding target nucleic acid, and a barcode region.

In some embodiments, the sample is contacted with a plurality of detectable probes, wherein each detectable probe is configured to hybridize to a complement of a barcode sequence in the barcode regions of the plurality of primary probes. In some embodiments, the complement of the barcode sequence is present in multiple copies in a nucleic acid concatemer, such as a rolling circle amplification (RCA) product. In some embodiments, the method further comprises detecting a signal associated with the plurality of detectable probes or absence thereof at one or more locations in the sample. In some embodiments, the sample is contacted with a subsequent plurality of detectable probes, wherein each detectable probe in the subsequent plurality is configured to hybridize to a complement of the subsequent barcode sequence in the barcode regions of the plurality of primary probes. In some embodiments, the complement of the subsequent barcode sequence is present in multiple copies in a nucleic acid concatemer, such as a rolling circle amplification (RCA) product. In some embodiments, the method further comprises detecting a subsequent signal associated with the subsequent plurality of detectable probes or absence thereof at the one or more locations in the sample. In some embodiments, the method further comprises generating a signal code sequence comprising signal codes corresponding to the signal or absence thereof and the subsequent signal or absence thereof, respectively, at the one or more locations, wherein the signal code sequence corresponds to one of the one or more target nucleic acids, thereby identifying the target nucleic acid at the one or more locations in the sample. In some embodiments, the RCA products for multiple target nucleic acids (e.g., target RNA) are generated in the sample, and the RCA products are generated using fragments of the target nucleic acids (e.g., generated by RNase H1 and/or RNase H2 treatment) and/or externally provided DNA oligonucleotides as RCA primers.

In some embodiments, the method comprises generating a signal code sequence at one or more locations in a sample, the signal code sequence comprising signal codes corresponding to the signals (or absence thereof) associated with detectable probes for in situ hybridization that are sequentially applied to the sample, wherein the signal code sequence corresponds to an analyte in the sample, thereby detecting the analyte at the one or more of the multiple locations in the sample.

In some embodiments, a method disclosed herein comprises generating rolling circle amplification (RCA) products associated with one or more target nucleic acids (e.g., target RNA) in a sample. In some embodiments, the RCA products are detected in situ in a sample, thereby detecting the one or more target nucleic acids. In some embodiments, each of the RCA products comprises multiple complementary copies of a barcode sequence, wherein the barcode sequence is associated with a target nucleic acid in the sample and is assigned a signal code sequence. In some embodiments, the method comprises contacting the sample with a first detectable probe comprising (i) a recognition sequence complementary to a sequence in the complementary copies of the barcode sequence and (ii) a reporter. In some embodiments, the method comprises detecting a first signal or absence thereof from the reporter of the first detectable probe hybridized to its corresponding sequence of the complementary copies of the barcode sequence in the RCA product, wherein the first signal or absence thereof corresponds to a first signal code in the signal code sequence. In some embodiments, the method comprises contacting the sample with a subsequent detectable probe comprising (i) a recognition sequence complementary to a sequence of the complementary copies of the barcode sequence and (ii) a reporter. In some embodiments, the method comprises detecting a subsequent signal or absence thereof from the reporter of the subsequent detectable probe hybridized to its corresponding sequence of the complementary copies of the barcode sequence in the RCA product, wherein the subsequent signal or absence thereof corresponds to a subsequent signal code in the signal code sequence. In some embodiments, the signal code sequence comprising the first signal code and the subsequent signal code is determined at a location in the sample, thereby decoding the barcode sequence and identifying the target nucleic acid (e.g., target RNA) at the location in the sample. In some embodiments, the RCA products for multiple target nucleic acids (e.g., target RNA) are generated in the sample, and the RCA products are generated using fragments of the target nucleic acids (e.g., generated by RNase H1 and/or RNase H2 treatment) and externally provided DNA oligonucleotides as RCA primers.

In some embodiments, the method comprises imaging the biological sample to detect the RCP. In some embodiments, the imaging comprises detecting a signal associated with a fluorescently labeled probe that directly or indirectly binds to the RCP. In some instances, the fluorescently labeled probe directly binds to the RCP (e.g., to a barcode sequence or subunit thereof in the RCP). In some embodiments, the fluorescently labeled probe indirectly binds to the RCP (e.g., the fluorescently labeled probe binds to one or more intermediate probes that bind to the RCP). In some embodiments, one or more intermediate probes binds to a barcode sequence or subunit thereof in the RCP, and the one or more intermediate probes comprise one or more barcode sequences corresponding to one or more fluorescently labeled probes. In some embodiments, the fluorescently labeled probe hybridizes to a corresponding barcode sequence in the intermediate probe.

In some embodiments, a sequence of the RCP is analyzed at a location in the biological sample or a matrix embedding the biological sample. In some embodiments, the sequence of the RCP is analyzed by sequential hybridization, sequencing by hybridization, sequencing by ligation, sequencing by synthesis, sequencing by binding, or a combination thereof. In some embodiments, the sequence of the RCP product comprises one or more barcode sequences or complements thereof (e.g., one or more barcode sequences or complements thereof that individually or in combination identify the target RNA).

In some embodiments, a target RNA described herein can be associated with one or more barcode(s) present in a circular probe or circularizable probe or probe set. In some embodiments, a circular probe or circularizable probe or probe set comprises at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner. In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, the barcode sequence comprises one or more barcode positions each comprising one or more barcode subunits. In some embodiments, a barcode position in the barcode sequence partially overlaps an adjacent barcode position in the barcode sequence. In some embodiments, the first detectable probe and the subsequent detectable probe are in a set of detectable probes each comprising the same recognition sequence and a reporter. In some embodiments, the reporter of each detectable probe in the set comprises a binding site for a reporter probe comprising a detectable moiety. In some embodiments, the reporter probe binding site of the first detectable probe and the reporter probe binding site of the subsequent detectable probe are the same. In some embodiments, the reporter probe binding site of the first detectable probe and the reporter probe binding site of the subsequent detectable probe are different. In some embodiments, the detectable moiety is a fluorophore and the signal code sequence is a fluorophore sequence uniquely assigned to the target nucleic acid (e.g., target RNA). In some embodiments, the detectable probes in the set are contacted with the sample sequentially in a pre-determined sequence which corresponds to the signal code sequence assigned to the barcode sequence. In some embodiments, the detectable probes in the set are contacted with the sample to determine signal codes in the signal code sequence until sufficient signal codes have been determined to decode the barcode sequence, thereby identifying the target nucleic acid (e.g., target RNA).

In some aspects, the provided methods involve analyzing, e.g., detecting or determining, one or more sequences present in the polynucleotides and/or in a product or derivative thereof, such as in an amplified circular probe or circularizable probe or probe set (e.g., padlock probe). In some cases, the analysis is performed on one or more images captured, and may comprise processing the image(s) and/or quantifying signals observed. For example, the analysis may comprise processing information of one or more cell types, one or more types of biomarkers, a number or level of a biomarker, and/or a number or level of cells detected in a particular region of the sample. In some embodiments, the analysis comprises detecting a sequence e.g., a barcode present in the sample. In some embodiments, the analysis includes quantification of puncta (e.g., if amplification products are detected). In some cases, the analysis includes determining whether particular cells and/or signals are present that correlate with one or more biomarkers from a particular panel. In some embodiments, the obtained information may be compared to a positive and negative control, or to a threshold of a feature to determine if the sample exhibits a certain feature or phenotype. In some cases, the information may comprise signals from a cell, a region, and/or comprise readouts from multiple detectable labels. In some case, the analysis further includes displaying the information from the analysis or detection step. In some embodiments, software may be used to automate the processing, analysis, and/or display of data.

In any of the embodiments herein, a sequence associated with the target nucleic acid or the circular probe(s) can comprise one or more barcode sequences or complements thereof. In any of the embodiments herein, the sequence of the rolling circle amplification product can comprise one or more barcode sequences or complements thereof. In any of the embodiments herein, a circular or circularizable probe can comprise one or more barcode sequences or complements thereof. In any of the embodiments herein, the one or more barcode sequences can comprise a barcode sequence corresponding to the target nucleic acid. In any of the embodiments herein, the one or more barcode sequences can comprise a barcode sequence corresponding to the sequence of interest, such as variant(s) of a single nucleotide of interest.

In some embodiments, a nucleic acid probe, such as a primary or a secondary nucleic acid probe, may also comprise 1, 2, 3, 4, 5, 6, 7, 8, 9, 10, 11, 12, 13, 14, 15 or more, 20 or more, 32 or more, 40 or more, or 50 or more barcode sequences. The barcode sequences may be positioned anywhere within the nucleic acid probe. If more than one barcode sequences are present, the barcode sequences may be positioned next to each other, and/or interspersed with other sequences. In some embodiments, two or more of the barcode sequences may also at least partially overlap. In some embodiments, two or more of the barcode sequences in the same probe do not overlap. In some embodiments, all of the barcode sequences in the same probe are separated from one another by at least a phosphodiester bond (e.g., they may be immediately adjacent to each other but do not overlap), such as 1, 2, 3, 4, 5, 6, 7, 8, 9, 10 or more nucleotides apart.

The barcode sequences, if present, may be of any length. If more than one barcode sequence is used, the barcode sequences may independently have the same or different lengths, such as at least 5, at least 10, at least 15, at least 20, at least 25, at least 30, at least 35, at least 40, at least 50 nucleotides in length. In some embodiments, the barcode sequence may be no more than 120, no more than 112, no more than 104, no more than 96, no more than 88, no more than 80, no more than 72, no more than 64, no more than 56, no more than 48, no more than 40, no more than 32, no more than 24, no more than 16, or no more than 8 nucleotides in length. Combinations of any of these are also possible, e.g., the barcode sequence may be between 5 and 10 nucleotides, between 8 and 15 nucleotides, etc.

The barcode sequence may be arbitrary or random. In certain cases, the barcode sequences are chosen so as to reduce or minimize homology with other components in a sample, e.g., such that the barcode sequences do not themselves bind to or hybridize with other nucleic acids suspected of being within the cell or other sample. In some embodiments, between a particular barcode sequence and another sequence (e.g., a cellular nucleic acid sequence in a sample or other barcode sequences in probes added to the sample), the homology may be less than 10%, less than 8%, less than 7%, less than 6%, less than 5%, less than 4%, less than 3%, less than 2%, or less than 1%. In some embodiments, the homology may be less than 20, 19, 18, 17, 16, 15, 14, 13, 12, 11, 10, 9, 8, 7, 6, 5, 4, 3, or 2 bases, and in some embodiments, the bases are consecutive bases.

In any of the embodiments herein, the detecting step comprises contacting the biological sample with one or more detectably labeled probes that directly or indirectly hybridize to the rolling circle amplification product, and dehybridizing the one or more detectably labeled probes from the rolling circle amplification product. In any of the embodiments herein, the contacting and dehybridizing steps can be repeated with the one or more detectably labeled probes and/or one or more other detectably labeled probes that directly or indirectly hybridize to the rolling circle amplification product.

In any of the embodiments herein, the detecting step comprises contacting the biological sample with one or more intermediate probes that directly or indirectly hybridize to the rolling circle amplification product, wherein the one or more intermediate probes are detectable using one or more detectably labeled probes. In any of the embodiments herein, the detecting step further comprises dehybridizing the one or more intermediate probes and/or the one or more detectably labeled probes from the rolling circle amplification product. In any of the embodiments herein, the contacting and dehybridizing steps are repeated with the one or more intermediate probes, the one or more detectably labeled probes, one or more other intermediate probes, and/or one or more other detectably labeled probes.

In some embodiments, the detection may be spatial, e.g., in two or three dimensions. In some embodiments, the detection may be quantitative, e.g., the amount or concentration of a primary nucleic acid probe (and of a target nucleic acid) may be determined. In some embodiments, the primary probes, secondary probes, higher order probes, and/or detectably labeled probes may comprise any of a variety of entities able to hybridize a nucleic acid, e.g., DNA, RNA, LNA, and/or PNA, etc., depending on the application.

In some embodiments, a method disclosed herein may also comprise one or more signal amplification components. In some embodiments, the present disclosure relates to the detection of nucleic acids sequences in situ using probe hybridization and generation of amplified signals associated with the probes (e.g., using RCA), wherein background signal is reduced and sensitivity is increased.

In some embodiments, the methods comprise detecting the sequence of all or a portion of the RCP, such as one or more barcode sequences present in the RCP. In some embodiments, the analysis and/or sequence determination comprises detecting all or a portion of the RCP(s) and/or in situ hybridization to the RCP(s). In some embodiments, the sequencing step involves sequencing by hybridization, sequencing by ligation, and/or fluorescent in situ sequencing, hybridization-based in situ sequencing and/or wherein the in situ hybridization comprises sequential fluorescent in situ hybridization. In some embodiments, the detection or determination comprises hybridizing to the RCP a detection oligonucleotide labeled with a fluorophore, an isotope, a mass tag, or a combination thereof. In some embodiments, the detection or determination comprises imaging the RCP. In some embodiments, the target nucleic acid is an mRNA in a tissue sample, and the detection or determination is performed when the target nucleic acid and/or the RCP is in situ in the tissue sample. In some embodiments, the RCP comprises (e.g., is covalently attached to) the cleaved target RNA that is used as a primer, or a portion thereof at a location in the biological sample. In some embodiments, the analytes (e.g., target RNAs), probes and/or amplification products (e.g., RCPs) described herein are anchored to a polymer matrix (e.g., as described in Section IV). For example, the polymer matrix can be a hydrogel. In some embodiments, cross-linking of the matrix or components to be anchored to the matrix can be performed chemically and/or photochemically, or alternatively by any other suitable hydrogel-formation method.

In some aspects, the provided methods comprise imaging the RCP, for example, via binding of the detectably labeled probe detecting the detectable label. In some embodiments, the detectably labeled probe comprises a detectable label that can be measured and quantitated. The detectable label can be any label that can be measured, e.g., fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. In some embodiments, a detectable probe containing a detectable label can be used to detect one or more RCPs according to the methods described herein. In some embodiments, the methods involve incubating the detectable probe containing the detectable label with the sample, washing unbound detectable probe, and detecting the label, e.g., by imaging.

In some embodiments, the detectable label is a fluorophore that comprises a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, cyanine-3 (Cy3), cyanine-5 (Cy5), cyanine-7 (Cy7), rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenicol acetyl transferase, and urease.

Fluorescence detection in tissue samples can often be hindered by the presence of strong background fluorescence. Background fluorescence can arise from a variety of sources, including aldehyde fixation, extracellular matrix components, red blood cells, lipofuscin, and the like. Tissue background fluorescence (or autofluorescence) can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), True-Black Lipofuscin Autofluorescence Quencher (Biotium), MaxBlock Autofluorescence Reducing Reagent Kit (MaxVision Biosciences), and/or a very intense black dye (e.g., Sudan Black, or comparable dark chromophore).

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as $^{125}I$, $^{35}S$, $^{14}C$, or $^3H$. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091,519, all of which are herein incorporated by reference in their entireties. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes), all of which are herein incorporated by reference in their entireties. Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264, all of which are herein incorporated by reference in their entireties. As used herein, the term "fluorescent label" comprises a signaling moiety that conveys information through the fluorescent absorption and/or emission properties of one or more molecules. Exemplary fluorescent properties comprise fluorescence intensity, fluorescence lifetime, emission spectrum characteristics and energy transfer.

Examples of commercially available fluorescent nucleotide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.).

Other fluorophores available for post-synthetic attachment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, and Cy7 (Amersham Biosciences, Piscataway, N.J.). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

Biotin, or a derivative thereof, may also be used as a label on a nucleotide and/or a polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. In any of the embodiments herein, an antibody can be an antibody molecule of any class, or any sub-fragment thereof, such as a Fab.

Other suitable labels for a polynucleotide sequence may comprise fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, a nucleotide and/or a polynucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, all of which are herein incorporated by reference in their entireties, and PCT publication WO 91/17160. Many different hapten-capture agent pairs are available for use. Exemplary haptens comprise, but are not limited to, biotin, des-biotin and other derivatives, dinitrophenol, dansyl, fluorescein, Cy5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some aspects, the detecting involves using detection methods such as flow cytometry; sequencing; probe binding and electrochemical detection; pH alteration; catalysis induced by enzymes bound to DNA tags; quantum entanglement; Raman spectroscopy; terahertz wave technology; and/or scanning electron microscopy. In some aspects, the flow cytometry is mass cytometry or fluorescence-activated flow cytometry. In some aspects, the detecting comprises performing microscopy, scanning mass spectrometry or other imaging techniques described herein. In such aspects, the detecting comprises determining a signal, e.g., a fluorescent signal.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a simpler set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity, so long exposures are often required. As only one point in the sample is illuminated at a time, 2D or 3D imaging requires scanning over a regular raster (e.g., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large, clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequencing or sequence detection is performed in situ. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55-65, and Lee et al., (2014) *Science,* 343(6177), 1360-1363, all of which are herein incorporated by reference in their entireties. In addition, examples of methods and systems for performing in situ sequencing are described in US 2016/0024555, US 2019/0194709, and in U.S. Pat. Nos. 10,138,509, 10,494, 662 and 10,179,932, all of which are herein incorporated by reference in their entireties. Exemplary techniques for in situ sequencing comprise, but are not limited to, STARmap (described for example in Wang et al., (2018) *Science,* 361(6499) 5691, the content of which is herein incorporated by reference in its entirety), MERFISH (described for example in Moffitt, (2016) *Methods in Enzymology,* 572, 1-49, the content of which is herein incorporated by reference in its entirety), hybridization-based in situ sequencing (HybISS) (described for example in Gyllborg et al., Nucleic Acids Res (2020) 48(19):e112, the content of which is herein incorporated by reference in its entirety), and FISSEQ (described for example in US 2019/0032121, the content of which is herein incorporated by reference in its entirety). In some cases, sequencing can be performed after the analytes are released from the biological sample.

In some embodiments, analyzing, e.g., detecting or determining, one or more sequences present in the biological sample is performed using a base-by-base sequencing method, e.g., sequencing-by-synthesis (SBS), sequencing-by-avidity (SBA) or sequencing-by-binding (SBB). In some embodiments, the biological sample is contacted with a sequencing primer and base-by-base sequencing using a cyclic series of nucleotide incorporation or binding, respectively, thereby generating extension products of the sequencing primer is performed followed by removing, cleaving, or blocking the extension products of the sequencing primer.

Generally in sequencing-by-synthesis methods, a first population of detectably labeled nucleotides (e.g., dNTPs) are introduced to contact a template nucleotide (e.g., a barcode sequence in the RCP) hybridized to a sequencing primer, and a first detectably labeled nucleotide (e.g., A, T, C, or G nucleotide) is incorporated by a polymerase to extend the sequencing primer in the 5' to 3' direction using a complementary nucleotide (a first nucleotide residue) in the template nucleotide as template. A signal from the first detectably labeled nucleotide can then be detected. The first population of nucleotides may be continuously introduced, but in order for a second detectably labeled nucleotide to incorporate into the extended sequencing primer, nucleotides in the first population of nucleotides that have not incorporated into a sequencing primer are generally removed (e.g., by washing), and a second population of detectably labeled nucleotides are introduced into the reaction. Then, a second detectably labeled nucleotide (e.g., A, T, C, or G nucleotide) is incorporated by the same or a different polymerase to extend the already extended sequencing primer in the 5' to 3' direction using a complementary nucleotide (a second nucleotide residue) in the template nucleotide as template. Thus, in some embodiments, cycles of introducing and removing detectably labeled nucleotides are performed.

In some embodiments, the base-by-base sequencing comprises using a polymerase that is fluorescently labeled. In some embodiments, the base-by-base sequencing comprises using a polymerase-nucleotide conjugate comprising a fluorescently labeled polymerase linked to a nucleotide moiety that is not fluorescently labeled. In some embodiments, the base-by-base sequencing comprises using a multivalent polymer-nucleotide conjugate comprising a polymer core, multiple nucleotide moieties, and one or more fluorescent labels.

In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US 2011/005986, US 2005/0100900, U.S. Pat. No. 9,217,178, US 2009/0118128, US 2012/0270305, US 2013/0260372, and US 2013/0079232, all of which are herein incorporated by reference in their entireties.

In some embodiments, sequencing is performed by sequencing-by-binding (SBB). Various aspects of SBB are described in U.S. Pat. No. 10,655,176 B2, the content of which is herein incorporated by reference in its entirety. In some embodiments, SBB comprises performing repetitive cycles of detecting a stabilized complex that forms at each position along the template nucleic acid to be sequenced (e.g. a ternary complex that includes the primed template nucleic acid, a polymerase, and a cognate nucleotide for the position), under conditions that prevent covalent incorporation of the cognate nucleotide into the primer, and then extending the primer to allow detection of the next position along the template nucleic acid. In the sequencing-by-binding approach, detection of the nucleotide at each position of the template occurs prior to extension of the primer to the next position. Generally, the methodology is used to distinguish the four different nucleotide types that can be present at positions along a nucleic acid template by uniquely labelling each type of ternary complex (i.e. different types of ternary complexes differing in the type of nucleotide it contains) or by separately delivering the reagents needed to form each type of ternary complex. In some instances, the labeling may comprise fluorescence labeling of, e.g., the cognate nucleotide or the polymerase that participate in the ternary complex.

In some embodiments, sequencing is performed by sequencing-by-avidity (SBA). Some aspects of SBA approaches are described in U.S. Pat. No. 10,768,173 B2, the content of which is herein incorporated by reference in its entirety. In some embodiments, SBA comprises detecting a multivalent binding complex formed between a fluorescently-labeled polymer-nucleotide conjugate, and a one or more primed target nucleic acid sequences (e.g., barcode sequences). Fluorescence imaging is used to detect the bound complex and thereby determine the identity of the N+1 nucleotide in the target nucleic acid sequence (where the primer extension strand is N nucleotides in length). Following the imaging step, the multivalent binding complex is disrupted and washed away, the correct blocked nucleotide is incorporated into the primer extension strand, and the sequencing cycle is repeated.

In some embodiments, sequencing is performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309: 1728-1732, and in U.S. Pat. Nos. 5,599,675; 5,750,341; 6,969,488; 6,172,218; and 6,306,597, all of which are herein incorporated by reference in their entireties.

In some embodiments, nucleic acid hybridization is used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004), all of which are herein incorporated by reference in their entireties. In some embodiments, detection of the barcode sequences is performed by sequential hybridization of probes to the barcode sequences or complements thereof and detecting complexes formed by the probes and barcode sequences or complements thereof. In some cases, each barcode sequence or complement thereof is assigned a sequence of signal codes that identifies the barcode sequence or complement thereof (e.g., a temporal signal signature or code that identifies the analyte), and detecting the barcode sequences or complements thereof can comprise decoding the barcode sequences of complements thereof by detecting the corresponding sequences of signal codes detected from sequential hybridization, detection, and removal of sequential pools of intermediate probes and the universal pool of detectably labeled probes. In some cases, the sequences of signal codes comprise fluorophore sequences assigned to the corresponding barcode sequences or complements thereof. In some embodiments, the detectably labeled probes are fluorescently labeled. In some embodiments, the barcode sequence or complement thereof is performed by sequential probe hybridization as described in US 2021/0340618, the content of which is herein incorporated by reference in its entirety.

In some embodiments, real-time monitoring of DNA polymerase activity can be used during sequencing. For example, nucleotide incorporations can be detected through fluorescence resonance energy transfer (FRET), as described for example in Levene et al., Science (2003), 299, 682-686, Lundquist et al., Opt. Lett. (2008), 33, 1026-1028, and Korlach et al., Proc. Natl. Acad. Sci. USA (2008), 105, 1176-1181, all of which are herein incorporated by reference in their entireties.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

III. Compositions and Kits

In some aspects, provided herein are compositions comprising any of the nucleic acid oligonucleotides, RNase H, primary probes (e.g., circular probes or circularizable probes or probe sets), detectably labeled probes, and/or intermediate probes described herein. Also provided herein are kits, for analyzing an analyte in a biological sample according to any of the methods described herein. In some embodiments, provided herein is a kit comprising any of the nucleic acid oligonucleotides described herein (e.g., for duplex formation with target RNA and RNase H cleavage of the target RNA). In some embodiments, the kit further comprises any of the circular probes and/or circularizable probes or probe sets disclosed herein. In some embodiments, the kit comprises RNase H. In some embodiments, the kit comprises a polymerase for rolling circle amplification. The various components of the kit may be present in separate containers or certain compatible components may be pre-combined into a single container. In some embodiments, the kits further contain instructions for using the components of the kit to practice the provided methods. In some embodiments, the kit comprises a plurality of circular probes and/or circularizable probes or probe sets and a corresponding plurality of nucleic acid oligonucleotides for cleaving and analyzing a plurality of target RNAs. In some embodiments, the plurality of nucleic acid oligonucleotides comprises at least 2, at least 5, at least 10, at least 25, at least 50, at least 75, at least 100, at least 300, at least 1,000, at least 3,000, at least 10,000, at least 30,000, at least 50,000, at least 100,000, at least 250,000, at least 500,000, or at least 1,000,000 distinguishable nucleic acid oligonucleotides (as described in Section II.A). In some embodiments, the kit comprises at least 2, at least 5, at least 10, at least 25, at least 50, at least 75, at least 100, at least 300, at least 1,000, at least 3,000, at least 10,000, at least 30,000, at least 50,000, at least 100,000, at least 250,000, at least 500,000, or at least 1,000,000 distinguishable nucleic acid probes (circular or circularizable probes as described in Section II.C).

In some aspects, provided herein is a kit or system for analyzing a biological sample, comprising: a) a nucleic acid oligonucleotide, wherein the oligonucleotide is complementary to an oligonucleotide hybridization region in a target ribonucleic acid (RNA); b) a circular probe, wherein the circular probe comprises a target recognition sequence complementary to a target sequence in the target RNA, wherein the target sequence in the target RNA overlaps with the oligonucleotide hybridization region in the target RNA by between 1 and 20 nucleotides; and c) an RNase H for cleaving the oligonucleotide hybridization region of the target RNA when hybridized to the oligonucleotide. In some embodiments, the kit or system further comprises a polymerase for performing rolling circle amplification of the circular probe, using the cleaved target RNA as a primer. In some embodiments, the oligonucleotide hybridization region and the target sequence overlap by about 8 to about 10 nucleotides. In various embodiments, the oligonucleotide hybridization region and the target sequence overlap by at least 8 nucleotides, at least 9 nucleotides, or at least 10 nucleotides. In some embodiments, the oligonucleotide hybridization region and the target sequence overlap by no more than 15 nucleotides, no more than 12 nucleotides, or no more than 10 nucleotides.

In some aspects, provided herein is a kit or system for analyzing a biological sample, comprising: a) a nucleic acid oligonucleotide, wherein the oligonucleotide is complementary to an oligonucleotide hybridization region in a target ribonucleic acid (RNA); b) a circularizable probe, the circularizable probe comprises a target recognition sequence complementary to a target sequence in the target RNA, wherein the target sequence in the target RNA overlaps with the oligonucleotide hybridization region in the target RNA by between 1 and 20 nucleotides; and c) an RNase H for cleaving the oligonucleotide hybridization region of the target RNA when hybridized to the oligonucleotide. In some embodiments, the kit or system further comprises a polymerase for performing rolling circle amplification of a circularized probe generated from the circularizable probe, using the cleaved target RNA as a primer. In some embodiments, the kit further comprises a ligase for generating the circularized probe by ligating the ends of the circularizable probe together. In some embodiments, the oligonucleotide hybridization region and the target sequence overlap by about 8 to about 10 nucleotides. In various embodiments, the oligonucleotide hybridization region and the target sequence overlap by at least 8 nucleotides, at least 9 nucleotides, or at least 10 nucleotides. In some embodiments, the oligonucleotide hybridization region and the target sequence overlap by no more than 15 nucleotides, no more than 12 nucleotides, or no more than 10 nucleotides. In some embodiments, the target recognition sequence of the circularizable probe comprises a first hybridization region having a ligatable 5' end and a second hybridization region having a ligatable 3' end, wherein the first hybridization region is complementary to a 5' portion of the target sequence, and the second hybridization region is complementary to a 3' portion of the target sequence.

In some aspects, provided herein is a kit or system for analyzing a biological sample, comprising: a) a nucleic acid oligonucleotide, wherein the oligonucleotide is complementary to an oligonucleotide hybridization region in a target ribonucleic acid (RNA); b) a circularizable probe set, wherein the circularizable probe set comprises a target recognition sequence complementary to a target sequence in the target RNA, wherein the target sequence in the target RNA overlaps with the oligonucleotide hybridization region in the target RNA by between 1 and 20 nucleotides; and c) an RNase H for cleaving the oligonucleotide hybridization region of the target RNA when hybridized to the oligonucleotide. In some embodiments, the kit or system further comprises a polymerase for performing rolling circle amplification of a circularized probe generated from the circularizable probe set, using the cleaved target RNA as a primer. In some embodiments, the kit further comprises a ligase for generating the circularized probe by ligating ends of the circularizable probe set together. In some embodiments, the oligonucleotide hybridization region and the target sequence overlap by about 8 to about 10 nucleotides. In various embodiments, the oligonucleotide hybridization region and the target sequence overlap by at least 8 nucleotides, at least 9 nucleotides, or at least 10 nucleotides. In some embodiments, the oligonucleotide hybridization region and the target sequence overlap by no more than 15 nucleotides, no more than 12 nucleotides, or no more than 10 nucleotides. In some embodiments, the target recognition sequence of the circularizable probe set comprises a first hybridization region having a ligatable 5' end and a second hybridization region having a ligatable 3' end, wherein the first hybridization region is complementary to a 5' portion of the target sequence, and the second hybridization region is complementary to a 3' portion of the target sequence. In some embodiments, the first hybridization region is in a first nucleic acid molecule, and the second hybridization region is in a second nucleic acid molecule. In various embodiments, the 3' end of the first nucleic acid molecule and the 5' end of the second nucleic acid molecule can also be ligated together to form a circularized probe from the circularizable probe set (e.g., using a nucleic acid splint that hybridizes to the 3' end of the first nucleic acid molecule and the 5' end of the second nucleic acid molecule).

In any of the embodiments of the kit or system, the 5' portion of the target sequence and the 3' portion of the target sequence can individually be about 15 to about 30 nucleotides in length. In some embodiments, the 5' portion of the target sequence is about 15 to 25 nucleotides in length, or about 20 nucleotides in length. In some embodiments, the 3' portion of the target sequence is about 15 to 25 nucleotides in length, or about 20 nucleotides in length. In some embodiments, the oligonucleotide hybridization region and the 3' portion of the target sequence overlap by about 8 to about 10 nucleotides. In any of the embodiments of the kit or system, the nucleic acid oligonucleotide can comprise at least 4, 5, 6, 7, or 8 consecutive deoxyribonucleotides. In some embodiments, the nucleic acid oligonucleotide is a deoxyribonucleic acid (DNA) oligonucleotide.

In some aspects, the polymerase of the kit or system is in a first reaction mixture comprising a non-catalytic metal of the polymerase and the kit or system further comprises a second reaction mixture comprising a catalytic cofactor of the polymerase to perform the rolling circle amplification. In some instances, the non-catalytic metal is barium, strontium, iron, cobalt, nickel, tin, zinc, or europium. In some instances, the non-catalytic metal is calcium or strontium. In some instances, the first reaction mixture is substantially free of a catalytic cofactor of the polymerase, optionally wherein the catalytic cofactor is selected from the group consisting of $Mg^{2+}$, $Co^{2+}$, and $Mn^{2+}$. In some instances, the catalytic cofactor is a di-cation selected from the group consisting of $Mg^{2+}$, $Co^{2+}$, and $Mn^{2+}$.

In some instances, the kit or system further comprises reagents for performing sequencing by ligation, sequencing by synthesis, sequencing by binding, or a combination thereof. In some instances, the kit or system further comprises one or more intermediate probes and a universal pool of detectably labeled probes (e.g., as described in Section II.E).

In some embodiments, the kit or system contains reagents and/or consumables required for performing one or more steps of the provided methods. In some embodiments, the kit or system contains reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as detectably labeled probes for binding to one or more barcode sequences or complements thereof, or detectable labels.

IV. Biological Sample Preparation

A sample disclosed herein can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can include nucleic acids (such as DNA or RNA), proteins/polypeptides, carbohydrates, and/or lipids. The biological sample can be obtained as a tissue sample, such as a tissue section, biopsy, a core biopsy, a cell pellet, a cell block, a needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Biological samples can be derived from a homogeneous culture or population of the subjects or organisms mentioned herein or alternatively from a collection of several different organisms. Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose. In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Preparation

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick. More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes). In some embodiments, the biological sample (e.g., FFPE sample) is permeable after deparaffinization. In some embodiments, processing of the biological sample, such as de-waxing, allows the biological sample to become permeabilized.

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or circularizable probe or probe set (e.g., padlock probe). In some embodiments, one or more post-fixing step is performed after a hybridization complex comprising a probe and a target is formed in a sample. In some embodiments, one or more post-fixing step is performed prior to a ligation reaction disclosed herein.

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked.

In some embodiments, a biological sample can be permeabilized to facilitate transfer of species (such as probes) into the sample. If a sample is not permeabilized sufficiently, the transfer of species (such as probes) into the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the content of which is herein incorporated by reference in its entirety. Any suitable method for sample permeabilization can generally be used in connection with the samples described herein.

In some embodiments, the biological sample can be permeabilized by any suitable methods. For example, one or more lysis reagents can be added to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes. Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to open up DNA in a cell for hybridization by a probe. For example, proteinase K treatment may be used to free up DNA with proteins bound thereto.

(ii) Embedding

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample. Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some aspects, a biological sample can be embedded in any of a variety of other embedding materials to provide structural substrate to the sample prior to sectioning and other handling steps. In some cases, the embedding material can be removed e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other suitable hydrogel-formation method.

In some embodiments, the biological sample is reversibly cross-linked prior to or during an in situ assay. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible or irreversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other suitable hydrogel-formation method. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 m to about 2 mm.

Additional methods and aspects of hydrogel embedding of biological samples are described for example in Chen et al., *Science* 347(6221):543-548, 2015, the entire content of which is incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible. In some embodiments, HTC reagents are added to the hydrogel before, contemporaneously with, and/or after polymerization. In some embodiments, a cell labeling agent is added to the hydrogel before, contemporaneously with, and/or after polymerization. In some embodiments, a cell-penetrating agent is added to the hydrogel before, contemporaneously with, and/or after polymerization.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, ligase, proteinase K, and DNAse. Additional reagents can also include reverse transcriptase enzymes, including enzymes with terminal transferase activity, primers, and oligonucleotides. In some embodiments, optical labels are added to the hydrogel subunits before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a biological sample embedded in a matrix (e.g., a hydrogel) can be isometrically expanded. Isometric expansion methods that can be used include hydration, a preparative step in expansion microscopy, as described in, e.g., Chen et al., *Science* 347(6221):543-548, 2015 and U.S. Pat. No. 10,059,990, all of which are herein incorporated by reference in their entireties. Isometric expansion of the sample can increase the spatial resolution of the subsequent analysis of the sample. The increased resolution in spatial profiling can be determined by comparison of an isometrically expanded sample with a sample that has not been isometrically expanded. In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(iii) Staining and Immunohistochemistry (IHC)

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DiR, DiD). Other cell membrane stains may include FM and RH dyes or immunohistochemical reagents specific for cell membrane proteins. In some examples, the stain may include but is not limited to, acridine orange, acid fuchsin, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine, or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Any suitable methods of destaining or discoloring a biological sample may be utilized and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

V. Opto-Fluidic Instruments for Analysis of Biological Samples

Provided herein is an instrument having integrated optics and fluidics modules (an "opto-fluidic instrument" or "opto-fluidic system") for detecting target molecules (e.g., nucleic acids, proteins, antibodies, etc.) in biological samples (e.g., one or more cells or a tissue sample) as described herein. In an opto-fluidic instrument, the fluidics module is configured to deliver one or more reagents (e.g., nucleic acid oligonucleotides for RNase H cutting and RNase H) to the biological sample and/or remove spent reagents therefrom. In some embodiments, the fluidics module is configured to deliver one or more nucleic acid oligonucleotides (e.g., any as described in Section II.A) sequentially or simultaneously with an RNase H for cleavage of one or more target RNAs. In some cases, the fluidics module is configured to remove the nucleic acid oligonucleotide(s) and/or RNase H after allowing the RNase H to cleave the target RNA(s) hybridized to the nucleic acid oligonucleotide(s). For example, one or more wash steps can be performed to remove the RNase H and/or nucleic acid oligonucleotide(s). In some embodiments, RNase H for cleavage of one or more target RNAs is performed prior to the sample being placed on the instrument. In some embodiments, the fluidics module is configured to deliver one or more further reagents (e.g., primary probe(s) such as circular probe(s) or circularizable probe(s) or probe set(s)) and/or to remove non-specifically hybridized probe(s). In some embodiments, the fluidics module is configured to deliver one or more detectably labeled probes and optionally intermediate probes to detect the RCP(s) in the biological sample.

Additionally, the optics module is configured to illuminate the biological sample with light having one or more spectral emission curves (over a range of wavelengths) and subsequently capture one or more images of emitted light signals from the biological sample during one or more probing cycles (e.g., as described in Section II.E). In various embodiments, the captured images may be processed in real time and/or at a later time to determine the presence of the one or more target molecules in the biological sample, as well as three-dimensional position information associated with each detected target molecule. Additionally, the opto-fluidics instrument includes a sample module configured to receive (and, optionally, secure) one or more biological samples. In some instances, the sample module includes an X-Y stage configured to move the biological sample along an X-Y plane (e.g., perpendicular to an objective lens of the optics module).

In various embodiments, the opto-fluidic instrument is configured to analyze one or more target RNAs (e.g., as described in Section II.D) in their naturally occurring place (i.e., in situ) within the biological sample. In some embodiments, the opto-fluidic instrument is configured to analyze one or more target RNAs (e.g., as described in Section II.D) in relative spatial locations within the biological sample. For example, an opto-fluidic instrument may be an in-situ analysis system used to analyze a biological sample and detect target molecules including but not limited to DNA, RNA, proteins, antibodies, and/or the like. In some embodiments, the in situ analysis system is used to detect one or more target RNAs using target-primed RCA according to the methods disclosed herein.

It is to be noted that, although the above discussion relates to an opto-fluidic instrument that can be used for in situ target molecule detection using target-primed RCA according to the methods disclosed herein, the discussion herein equally applies to any opto-fluidic instrument that employs any imaging or target molecule detection technique. That is, for example, an opto-fluidic instrument may include a fluidics module that includes fluids needed for establishing the experimental conditions required for the probing of target molecules in the sample. Further, such an opto-fluidic instrument may also include a sample module configured to receive the sample, and an optics module including an imaging system for illuminating (e.g., exciting one or more fluorescent probes within the sample) and/or imaging light signals received from the probed sample. The in-situ analysis system may also include other ancillary modules configured to facilitate the operation of the opto-fluidic instrument, such as, but not limited to, cooling systems, motion calibration systems, etc.

In various embodiments, the sample can be a biological sample (e.g., a tissue) that includes molecules such as DNA, RNA, proteins, antibodies, etc. For example, the sample can be a sectioned tissue that is treated to access the RNA thereof for hybridization of nucleic acid oligonucleotides and primary probes described herein (e.g., in Section II). Ligation of a primary probe or probe set hybridized to the target RNA may generate a circularized probe which can be enzymatically amplified and bound with detectably labeled probes, which can create bright signal that is convenient to image and has a high signal-to-noise ratio.

In various embodiments, the sample may be placed in the opto-fluidic instrument for analysis and detection of the molecules (e.g., target RNAs) in the sample. In various embodiments, the opto-fluidic instrument can be a system configured to facilitate the experimental conditions conducive for the detection of the target molecules. For example, the opto-fluidic instrument can include a fluidics module, an optics module, a sample module, and an ancillary module, and these modules may be operated by a system controller to create the experimental conditions for the probing of the molecules in the sample by selected probes (e.g., circularizable DNA probes), as well as to facilitate the imaging of the probed sample (e.g., by an imaging system of the optics module). In various embodiments, the various modules of the opto-fluidic instrument may be separate components in communication with each other, or at least some of them may be integrated together.

In various embodiments, the sample module may be configured to receive the sample into the opto-fluidic instrument. For instance, the sample module may include a sample interface module (SIM) that is configured to receive a sample device (e.g., cassette) onto which the sample can be deposited. That is, the sample may be placed in the opto-fluidic instrument by depositing the sample (e.g., the sectioned tissue) on a sample device that is then inserted into the SIM of the sample module. In some instances, the sample module may also include an X-Y stage onto which the SIM is mounted. The X-Y stage may be configured to move the SIM mounted thereon (e.g., and as such the sample device containing the sample inserted therein) in perpendicular directions along the two-dimensional (2D) plane of the opto-fluidic instrument.

The experimental conditions that are conducive for the detection of the RCPs in the sample may depend on the target molecule detection technique that is employed by the opto-fluidic instrument. For example, in various embodiments, the opto-fluidic instrument can be a system that is configured to detect RCPs in the sample via hybridization of probes. In such cases, the experimental conditions can include molecule hybridization conditions that result in the intensity of hybridization of the RCP to a probe (e.g., detectably labeled probe) being significantly higher when the detectably labeled probe sequence is complementary to the target RCP (e.g., to a barcode sequence or subunit in the target RCP) than when there is a single-base mismatch. The hybridization conditions include the preparation of the sample using reagents such as washing/stripping reagents, hybridizing reagents, etc., and such reagents may be provided by the fluidics module.

In various embodiments, the fluidics module may include one or more components that may be used for storing the reagents, as well as for transporting said reagents to and from the sample device containing the sample. For example, the fluidics module may include reservoirs configured to store the reagents, as well as a waste container configured for collecting the reagents (e.g., and other waste) after use by the opto-fluidic instrument to analyze and detect the molecules of the sample. Further, the fluidics module may also include pumps, tubes, pipettes, etc., that are configured to facilitate the transport of the reagent to the sample device (e.g., and as such the sample). For instance, the fluidics module may include pumps ("reagent pumps") that are configured to pump washing/stripping reagents to the sample device for use in washing/stripping the sample (e.g., as well as other washing functions such as washing an objective lens of the imaging system of the optics module).

In various embodiments, the ancillary module can be a cooling system of the opto-fluidic instrument, and the cooling system may include a network of coolant-carrying tubes that are configured to transport coolants to various modules of the opto-fluidic instrument for regulating the temperatures thereof. In such cases, the fluidics module may include coolant reservoirs for storing the coolants and pumps (e.g., "coolant pumps") for generating a pressure differential, thereby forcing the coolants to flow from the reservoirs to the various modules of the opto-fluidic instrument via the coolant-carrying tubes. In some instances, the fluidics module may include returning coolant reservoirs that may be configured to receive and store returning coolants, e.g., heated coolants flowing back into the returning coolant reservoirs after absorbing heat discharged by the various modules of the opto-fluidic instrument. In such cases, the fluidics module may also include cooling fans that are configured to force air (e.g., cool and/or ambient air) into the returning coolant reservoirs to cool the heated coolants stored therein. In some instances, the fluidics module may also include cooling fans that are configured to force air directly into a component of the opto-fluidic instrument so as to cool said component. For example, the fluidics module may include cooling fans that are configured to direct cool or ambient air into the system controller to cool the same.

As discussed above, the opto-fluidic instrument may include an optics module which include the various optical components of the opto-fluidic instrument, such as but not limited to a camera, an illumination module (e.g., LEDs), an objective lens, and/or the like. The optics module may include a fluorescence imaging system that is configured to image the fluorescence emitted by the probes (e.g., oligonucleotides) in the sample after the probes are excited by light from the illumination module of the optics module.

In some instances, the optics module may also include an optical frame onto which the camera, the illumination module, and/or the X-Y stage of the sample module may be mounted.

In various embodiments, the system controller may be configured to control the operations of the opto-fluidic instrument (e.g., and the operations of one or more modules thereof). In some instances, the system controller may take various forms, including a processor, a single computer (or computer system), or multiple computers in communication with each other. In various embodiments, the system controller may be communicatively coupled with data storage, set of input devices, display system, or a combination thereof. In some cases, some or all of these components may be considered to be part of or otherwise integrated with the system controller, may be separate components in communication with each other, or may be integrated together. In other examples, the system controller can be, or may be in communication with, a cloud computing platform.

In various embodiments, the opto-fluidic instrument may analyze the sample and may generate the output that includes indications of the presence of the target molecules (e.g., target RNAs, the presence of which can be indicated by detecting target primed-RCPs associated with the target RNAs) in the sample. For instance, with respect to the example embodiment discussed above where the opto-fluidic instrument employs a hybridization technique for detecting RCPs, the opto-fluidic instrument may cause the sample to undergo successive rounds of detectably labeled probe hybridization (e.g., using two or more sets of fluorescent probes, where each set of fluorescent probes is excited by a different color channel) and be imaged to detect target molecules in the probed sample. In such cases, the output may include optical signatures (e.g., a codeword) specific to each gene, which allow the identification of the target RNAs.

VI. Terminology

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms "polynucleotide," "polynucleotide," and "nucleic acid molecule," used interchangeably herein, refer to polymeric forms of nucleotides of any length, either ribonucleotides or deoxyribonucleotides. Thus, this term comprises, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups.

A "primer" as used herein, in some embodiments, is an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

In some instances, "ligation" refers to the formation of a covalent bond or linkage between the termini of two or more nucleic acids, e.g., oligonucleotides and/or polynucleotides, in a template-driven reaction. The nature of the bond or linkage may vary widely and the ligation, in some embodiments, is carried out enzymatically or chemically. As used herein, ligations are usually carried out enzymatically to form a phosphodiester linkage between a 5' carbon terminal nucleotide of one oligonucleotide with a 3' carbon of another nucleotide.

The term "about" as used herein refers to the usual error range for the respective value readily known to the skilled person in this technical field. Reference to "about" a value or parameter herein comprises (and describes) embodiments that are directed to that value or parameter per se.

As used herein, the singular forms "a," "an," and "the" comprise plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be comprised in the smaller ranges, and are also encompassed within the claimed subject matter, subject to any specifically excluded limit in the stated range. Where the stated range comprises one or both of the limits, ranges excluding either or both of those comprised limits are also comprised in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

Exemplary Embodiments

Among the provided embodiments are:
1. A method of analyzing a biological sample, comprising:
   a) contacting the biological sample with a nucleic acid oligonucleotide, wherein the nucleic acid oligonucleotide hybridizes to an oligonucleotide hybridization region in a target ribonucleic acid (RNA);
   b) contacting the biological sample with an RNase H to cleave the target RNA in the oligonucleotide hybridization region to generate a cleaved target RNA;
   c) contacting the biological sample with a circular probe or a circularizable probe or probe set, wherein the circular probe or the circularizable probe or probe set comprises a target recognition sequence complementary to a target sequence in the target RNA, wherein the circular probe or the circularizable probe or probe set hybridizes to the target RNA;
   wherein the oligonucleotide hybridization region is adjacent to the 3' end of the target sequence or is overlapping with the 3' end of the target sequence;
   d) performing rolling circle amplification of the circular probe or of a circularized probe generated from the circularizable probe or probe set to generate a rolling circle amplification product (RCP) using the cleaved target RNA as a primer; and
   e) detecting the RCP in the biological sample.
2. The method of embodiment 1, wherein the biological sample is contacted with the nucleic acid oligonucleotide and with the RNase H simultaneously before contacting the biological sample with the circular probe or the circularizable probe or probe set.
3. The method of embodiment 1 or 2, wherein the method comprises washing the biological sample after contacting the biological sample with the RNase H and before contacting the biological sample with the circular probe or the circularizable probe or probe set.
4. The method of any of embodiments 1-3, wherein the oligonucleotide hybridization region and the target sequence overlap by about 1 to about 20 nucleotides.
5. The method of any of embodiments 1-4, wherein the oligonucleotide hybridization region and the target sequence overlap by about 8 to about 12 nucleotides.
6. The method of any of embodiments 1-5, wherein the oligonucleotide hybridization region and the target sequence overlap by at least 8 nucleotides, at least 9 nucleotides, or at least 10 nucleotides.
7. The method of any of embodiments 1-6, wherein the oligonucleotide hybridization region and the target sequence overlap by no more than 15 nucleotides, no more than 12 nucleotides, or no more than 10 nucleotides.
8. The method of any of embodiments 1-7, wherein the method does not comprise contacting the biological sample with a DNA primer that hybridizes to the circular probe or the circularized probe.

9. The method of any of embodiments 1-8, wherein the target recognition sequence of the circularizable probe or probe set is a split recognition sequence comprising a first hybridization region having a first ligatable end and a second hybridization region having a second ligatable end, wherein the first hybridization region hybridizes to a 5' portion of the target sequence, and the second hybridization region hybridizes to a 3' portion of the target sequence, and the method comprises ligating the first ligatable end to the second ligatable end to generate the circularized probe.

10. The method of embodiment 9, wherein the 5' portion of the target sequence and the 3' portion of the target sequence are each about 15 to about 30 nucleotides in length, optionally wherein the 5' portion of the target sequence and the 3' portion of the target sequence are each about 20 nucleotides in length.

11. The method of embodiment 9 or 10, wherein the oligonucleotide hybridization region and the 3' portion of the target sequence overlap by about 8 to about 10 nucleotides.

12. The method of any of embodiments 1-11, wherein the target RNA is attached directly or indirectly to the biological sample or to a matrix embedding the biological sample.

13. The method of any of embodiments 1-12, wherein the target RNA is crosslinked in the biological sample or in a matrix embedding the biological sample.

14. The method of any of embodiments 1-13, wherein the RCP is covalently linked to the target RNA.

15. The method of any of embodiments 1-14, wherein the RNase H comprises an RNase H1 and/or an RNase H2.

16. The method of any of embodiments 1-15, wherein contacting the biological sample with the RNase H comprises contacting the biological sample with between about 0.5 enzyme units (U) and about 50 U of the RNase H.

17. The method of any of embodiments 1-16, wherein the oligonucleotide hybridization region comprises an AA or AU sequence, wherein the AA or AU sequence is 1, 2, 3, 4, 5, or 6 nucleotides downstream of a cytosine or a guanine.

18. The method of embodiment 17, wherein the oligonucleotide hybridization region comprises a sequence of at least 2, 3, 4, or more cytosines and/or guanines beginning at a position 2, 3, 4, 5, or 6 nucleotides upstream of the AA or AU sequence.

19. The method of any of embodiments 1-18, wherein the oligonucleotide hybridization region comprises a CAAG sequence.

20. The method of any of embodiments 1-19, wherein the oligonucleotide hybridization region is about 10 to about 20 nucleotides in length, or about 15 to about 20 nucleotides in length.

21. The method of any of embodiments 1-20, wherein the nucleic acid oligonucleotide is about 10 to about 20 nucleotides in length, or about 15 to about 20 nucleotides in length.

22. The method of any of embodiments 1-21, wherein the oligonucleotide hybridization region comprises 1, 2, 3, 4, or more guanines and/or cytosines within 5-8 nucleotides of its 3' end.

23. The method of any of embodiments 1-22, wherein the nucleic acid oligonucleotide is single-stranded.

24. The method of any of embodiments 1-23, wherein performing the rolling circle amplification comprises incubating the biological sample with a polymerase for a duration of between about 30 minutes and about 2 hours.

25. The method of any of embodiments 1-24, wherein the method comprises contacting the biological sample with a polymerase in a first reaction mixture comprising a di-cation that is not a co-factor of the polymerase, and then contacting the biological sample with a second reaction mixture comprising a cofactor of the polymerase to perform the rolling circle amplification.

26. The method of embodiment 25, wherein the di-cation that is not a co-factor of the polymerase is barium, strontium, iron, cobalt, nickel, tin, zinc, or europium.

27. The method of embodiment 25, wherein the di-cation that is not a co-factor of the polymerase is calcium or strontium.

28. The method of embodiment 25, wherein the di-cation that is not a co-factor of the polymerase is strontium.

29. The method of embodiment 25, wherein the di-cation that is not a co-factor of the polymerase is $Ca^{2+}$.

30. The method of any of embodiments 25-29, wherein the di-cation that is not a co-factor of the polymerase stabilizes the polymerase, thereby inhibiting the polymerase activity and/or an exonuclease activity of the polymerase.

31. The method of any of embodiments 25-30, wherein the first reaction mixture is substantially free of a cofactor of the polymerase, optionally wherein the cofactor is selected from the group consisting of $Mg^{2+}$, $Co^{2+}$, and $Mn^{2+}$.

32. The method of any of embodiments 25-31, wherein the first reaction mixture comprises a chelating agent, optionally wherein the chelating agent comprises EDTA, EGTA, BAPTA, DTPA, or a combination thereof.

33. The method of any of embodiments 25-32, wherein the second reaction mixture comprises deoxynucleotide triphosphates (dNTPs) and/or nucleotide triphosphates (NTPs).

34. The method of any of embodiments 25-33, wherein the second reaction mixture comprises a cofactor of the polymerase, optionally wherein the cofactor is a di-cation selected from the group consisting of $Mg^{2+}$, $Co^{2+}$, and $Mn^{2+}$.

35. The method of any of embodiments 1-34, wherein the circularizable probe or probe set comprises one or more ribonucleotides.

36. The method of embodiment 35, wherein the one or more ribonucleotides are at and/or near a ligatable 3' end of the circularizable probe or probe set.

37. The method of embodiment 36, wherein a 3' terminal nucleotide of the circularizable probe or probe set hybridized to the target RNA is a ribonucleotide.

38. The method of any of embodiments 1-37, wherein a 3' end and a 5' end of the circularizable probe or probe set are ligated using the target RNA as a template.

39. The method of embodiment 38, wherein the 3' end and the 5' end of the circularizable probe or probe set are ligated without gap filling prior to ligation.

40. The method of embodiment 38, wherein the ligation of the 3' end and the 5' end is preceded by gap filling, and optionally wherein the gap is 1, 2, 3, 4, or 5 nucleotides.

41. The method of any of embodiments 1-40, wherein the circularizable probe or probe set is circularized by ligation selected from the group consisting of enzymatic ligation, chemical ligation, template dependent ligation, and template independent ligation.

42. The method of embodiment 41, wherein the ligation is template dependent ligation.

43. The method of embodiment 41, wherein the ligation is enzymatic ligation, wherein the enzymatic ligation comprises using a ligase having an RNA-templated DNA ligase activity and/or an RNA-templated RNA ligase activity.

44. The method of embodiment 42 or 43, wherein the enzymatic ligation comprises using a ligase selected from the group consisting of a *Chlorella* virus DNA ligase (PBCV DNA ligase), a T4 RNA ligase, a T4 DNA ligase, and a single-stranded DNA (ssDNA) ligase.

45. The method of any of embodiments 1-44, wherein the RCP is generated using a polymerase selected from the group consisting of Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof.

46. The method of any of embodiments 1-45, wherein the RCP is immobilized in the biological sample and/or cross-linked to one or more other molecules in the biological sample.

47. The method of any of embodiments 1-46, wherein the method comprises imaging the biological sample to detect the RCP.

48. The method of embodiment 47, wherein the imaging comprises detecting a signal associated with a fluorescently labeled probe that directly or indirectly binds to the RCP.

49. The method of any of embodiments 1-48, wherein a sequence of the RCP is analyzed at a location in the biological sample or a matrix embedding the biological sample.

50. The method of embodiment 49, wherein the sequence of the RCP is analyzed by sequential hybridization, sequencing by hybridization, sequencing by ligation, sequencing by synthesis, sequencing by binding, or a combination thereof.

51. The method of embodiment 50, wherein the sequence of the RCP comprises one or more barcode sequences or complements thereof.

52. The method of embodiment 51, wherein the one or more barcode sequences or complements thereof correspond to the target RNA.

53. A method of analyzing a biological sample, comprising:
a) contacting the biological sample with a plurality of nucleic acid oligonucleotides, wherein a first oligonucleotide of the plurality hybridizes to a first oligonucleotide hybridization region in a first target ribonucleic acid (RNA) in the biological sample, and a second oligonucleotide of the plurality hybridizes to a second oligonucleotide hybridization region in a second target RNA in the biological sample;
b) contacting the biological sample with an RNase H, wherein the RNase H cleaves the first and second target RNAs in their respective oligonucleotide hybridization regions to generate a first cleaved target RNA and a second cleaved target RNA;
c) contacting the biological sample with a plurality of circular probes or circularizable probes or probe sets, wherein a first circular probe or first circularizable probe or probe set of the plurality comprises a first target recognition sequence complementary to a first target sequence in the first target RNA,
wherein a second circular probe or second circularizable probe or probe set of the plurality comprises a second target recognition sequence complementary to a second target sequence in the second target RNA,
wherein the first and second circular probe or the first and second circularizable probe or probe set hybridize to their respective target RNAs,
wherein the first oligonucleotide hybridization region is adjacent to the 3' end of the first target sequence or is overlapping with the 3' end of the first target sequence, and
wherein the second oligonucleotide hybridization region is adjacent to the 3' end of the second target sequence or is overlapping with the 3' end of the second target sequence;
d) performing rolling circle amplification of the first and second circular probe or of a first and second circularized probe generated from the first and second circularizable probes or probe sets to generate a first and second rolling circle amplification product (RCP) using the first cleaved target RNA and the second cleaved target RNA as primers; and
e) detecting the first and second RCPs in the biological sample.

54. The method of embodiment 53, wherein detecting the first and second RCPs in the biological sample comprises detecting barcode sequences or complements thereof in the first and second RCPs.

55. The method of embodiment 54, wherein detecting the barcode sequences or complement thereof comprises:
contacting the biological sample with a universal pool of detectably labeled probes and a first pool of intermediate probes, wherein the intermediate probes of the first pool of intermediate probes comprise hybridization regions complementary to the barcode sequences or complements thereof and reporter regions complementary to a detectably labeled probe of the universal pool of detectably labeled probes;
detecting complexes formed between the barcode sequences or complements thereof, the intermediate probes of the first pool of intermediate probes, and the detectably labeled probes; and
removing the intermediate probes of the first pool of intermediate probes and the detectably labeled probes.

56. The method of embodiment 55, wherein detecting the barcode sequences or complements thereof further comprises:
contacting the biological sample with the universal pool of detectably labeled probes and a second pool of intermediate probes, wherein the intermediate probes of the second pool of intermediate probes comprise hybridization regions complementary to the barcode sequences or complements thereof and reporter regions complementary to a detectably labeled probe of the universal pool of detectably labeled probes; and
detecting complexes formed between the barcode sequences or complements thereof, the intermediate probes of the second pool of intermediate probes, and the detectably labeled probes.

57. The method of any of embodiments 54-56, wherein each barcode sequence or complement thereof is assigned a series of signal codes that identifies the barcode sequence or complement thereof, and
wherein detecting the barcode sequences or complements thereof comprises decoding the barcode sequences of complements thereof by detecting the corresponding sequences of signal codes detected from sequential hybridization, detection, and removal of sequential pools of intermediate probes and the universal pool of detectably labeled probes.

58. The method of embodiment 57, wherein the series of signal codes are fluorophore sequences assigned to the corresponding barcode sequences or complements thereof.

59. The method of any of embodiments 54-58, wherein the detectably labeled probes are fluorescently labeled.

60. The method of any of embodiments 1-59, wherein the biological sample is a fixed and/or permeabilized biological sample.

61. The method of any of embodiments 1-60, wherein the biological sample is a tissue sample.

62. The method of any of embodiments 1-61, wherein the biological sample is a frozen tissue sample or a fresh tissue sample.

63. The method of embodiment 61 or 62, wherein the tissue sample is a tissue slice between about 1 µm and about 50 µm in thickness, optionally wherein the tissue slice is between about 5 µm and about 35 µm in thickness.

64. The method of any of embodiments 1-63, wherein the biological sample is crosslinked.

65. The method of any of embodiments 1-64, wherein the biological sample is embedded in a hydrogel matrix.

66. The method of any of embodiments 1-65, wherein the biological sample is cleared.

67. The method of any of embodiments 1-64, wherein the biological sample is not embedded in a hydrogel matrix.

68. The method of any of embodiments 1-52 and 60-67, wherein the nucleic acid oligonucleotide comprises at least 4, 5, 6, 7, or 8 consecutive deoxyribonucleotides.

69. The method of any of embodiments 1-52 and 60-67, wherein the nucleic acid oligonucleotide is a deoxyribonucleic acid (DNA) oligonucleotide.

70. The method of any of embodiments 53-66, wherein the nucleic acid oligonucleotides individually comprise at least 4, 5, 6, 7, or 8 consecutive deoxyribonucleotides.

71. The method of any of embodiments 53-66, wherein the nucleic acid oligonucleotides are deoxyribonucleic acid (DNA) oligonucleotides.

72. The method of any of embodiments 1-71, comprising reacting at least one RNA in the biological sample with a polynucleotide kinase (PNK).

73. The method of embodiment 72, wherein the method comprises reacting at least one RNA in the biological sample with the PNK before contacting the biological sample with the circular probe or the circularizable probe or probe set.

74. The method of embodiment 72 or 73, wherein the method comprises reacting at least one RNA in the biological sample with the PNK before contacting the biological sample with the nucleic acid oligonucleotide and the RNase H.

75. The method of embodiment 73, wherein the method comprises reacting at least one RNA in the biological sample with the PNK after contacting the biological sample with the nucleic acid oligonucleotide and the RNase H.

76. The method of any of embodiments 72-75, wherein the PNK is a T4 Polynucleotide Kinase (T4 PNK) or a T7 Polynucleotide Kinase (T7-PNK).

77. The method of embodiment 76, wherein the PNK is a T4 PNK.

78. A method of analyzing a biological sample, comprising:
a) contacting the biological sample with a nucleic acid oligonucleotide, wherein the nucleic acid oligonucleotide hybridizes to an oligonucleotide hybridization region in a target ribonucleic acid (RNA);
b) contacting the biological sample with an RNase H, wherein the RNase H cleaves the target RNA in the oligonucleotide hybridization region to generate a cleaved target RNA;
c) incubating the biological sample with a polynucleotide kinase (PNK);
d) contacting the biological sample with a circular probe or a circularizable probe or probe set, wherein the circular probe or the circularizable probe or probe set comprises a target recognition sequence complementary to a target sequence in the target RNA, wherein the circular probe or the circularizable probe or probe set hybridizes to the target RNA;
wherein the oligonucleotide hybridization region is adjacent to the 3' end of the target sequence or is overlapping with the 3' end of the target sequence;
e) performing rolling circle amplification of the circular probe or of a circularized probe generated from the circularizable probe or probe set to generate a rolling circle amplification product (RCP) using the cleaved target RNA as a primer; and
f) detecting the RCP in the biological sample.

79. The method of embodiment 78, wherein performing the rolling circle amplification comprises contacting the biological sample with a polymerase in a first reaction mixture comprising a di-cation that is not a co-factor of the polymerase, and then contacting the biological sample with a second reaction mixture comprising a cofactor of the polymerase to perform the rolling circle amplification.

80. The method of embodiment 79, wherein the di-cation that is not a co-factor of the polymerase is barium, strontium, iron, cobalt, nickel, tin, zinc, or europium.

81. A kit for analyzing a biological sample, comprising:
a) a nucleic acid oligonucleotide, wherein the nucleic acid oligonucleotide is complementary to an oligonucleotide hybridization region in a target ribonucleic acid (RNA);
b) a circular probe or a circularizable probe or probe set, wherein the circular probe or the circularizable probe or probe set comprises a target recognition sequence complementary to a target sequence in the target RNA, wherein the target sequence in the target RNA overlaps with the oligonucleotide hybridization region in the target RNA by between 1 and 20 nucleotides; and
c) an RNase H for cleaving the oligonucleotide hybridization region of the target RNA when hybridized to the nucleic acid oligonucleotide.

82. A system for analyzing a biological sample, comprising:
a) a nucleic acid oligonucleotide, wherein the nucleic acid oligonucleotide is complementary to an oligonucleotide hybridization region in a target ribonucleic acid (RNA);
b) a circular probe or a circularizable probe or probe set, wherein the circular probe or the circularizable probe or probe set comprises a target recognition sequence complementary to a target sequence in the target RNA, wherein the target sequence in the target RNA overlaps with the oligonucleotide hybridization region in the target RNA by between 1 and 20 nucleotides;
c) an RNase H for cleaving the oligonucleotide hybridization region of the target RNA when hybridized to the nucleic acid oligonucleotide; and
d) a polymerase for performing rolling circle amplification of the circular probe or a circularized probe generated from the circularizable probe or probe set, using the cleaved target RNA as a primer.

83. The kit of embodiment 81 or the system of embodiment 82, wherein the oligonucleotide hybridization region and the target sequence overlap by about 8 to about 12 nucleotides.

84. The kit or system of any of embodiments 81-83, wherein the oligonucleotide hybridization region and the target sequence overlap by at least 8 nucleotides, at least 9 nucleotides, or at least 10 nucleotides.

85. The kit or system of any of embodiments 81-84, wherein the oligonucleotide hybridization region and the target sequence overlap by no more than 15 nucleotides, no more than 12 nucleotides, or no more than 10 nucleotides.

86. The kit or system of any of embodiments 81-85, wherein the target recognition sequence of the circularizable probe or probe set is a split recognition sequence comprising a first hybridization region having a first ligatable end and a second hybridization region having a second ligatable end, wherein the first hybridization region is complementary to a 5' portion of the target sequence, and the second hybridization region is complementary to a 3' portion of the target sequence.

87. The kit or system of embodiment 86, wherein the 5' portion of the target sequence and the 3' portion of the target sequence are each about 15 to about 30 nucleotides in length, optionally wherein the 5' portion of the target sequence and the 3' portion of the target sequence are each about 20 nucleotides in length.

88. The kit or system of embodiment 86 or 87, wherein the oligonucleotide hybridization region and the 3' portion of the target sequence overlap by about 8 to about 10 nucleotides.

89. The kit or system of any of embodiments 81-87, further comprising a polynucleotide kinase (PNK).

90. The kit or system of any of embodiments 81-89, wherein the polymerase is in a first reaction mixture comprising a non-catalytic metal of the polymerase and the kit or system further comprises a second reaction mixture comprising a catalytic cofactor of the polymerase to perform the rolling circle amplification.

91. The kit or system of embodiment 90, wherein the non-catalytic metal is barium, strontium, iron, cobalt, nickel, tin, zinc, or europium.

92. The kit or system of embodiment 90, wherein the non-catalytic metal is calcium or strontium.

93. The kit or system of embodiment 90, wherein the non-catalytic metal is strontium.

94. The kit or system of embodiment 90, wherein the non-catalytic metal is $Ca^{2+}$.

95. The kit or system of any of embodiments 81-94, wherein the first reaction mixture is substantially free of a catalytic cofactor of the polymerase, optionally wherein the catalytic cofactor is selected from the group consisting of $Mg^{2+}$, $Co^{2+}$, and $Mn^{2+}$.

96. The kit or system of any one of embodiments 90-95, wherein the catalytic cofactor is a di-cation selected from the group consisting of $Mg^{2+}$, $Co^{2+}$, and $Mn^{2+}$.

97. The kit or system of any of embodiments 81-96, further comprising reagents for performing sequencing by ligation, sequencing by synthesis, sequencing by binding, or a combination thereof.

98. The kit or system of any of embodiments 81-96, further comprising a universal pool of detectably labeled probes.

EXAMPLES

The following examples are included for illustrative purposes only and are not intended to limit the scope of the present disclosure.

Example 1: Target-Primed RCA (tpRCA) Using RNase H and a Nucleic Acid Oligonucleotide for Target RNA Cleavage Results in Improved Sensitivity, Signal Intensity and RCP Homogeneity This example provides results demonstrating that signal intensity for detected RCA products (RCPs) increases when a nucleic acid oligonucleotide and RNase H are used to cleave target RNA prior to hybridization of a circularizable probe.

Methods

Mouse brains were, right after surgical removal and without any fixation, embedded into OCT medium and directly frozen on dry ice, and thereafter stored at −80° C. until usage. Thin sections were then cut with a cryostat and sections were collected on glass slides (an optically transparent substrate). Sections were then shortly fixated in formaldehyde in PBS and washed, after which they were permeabilized. After the permeabilization, slides were washed in PBS.

Figure 2:
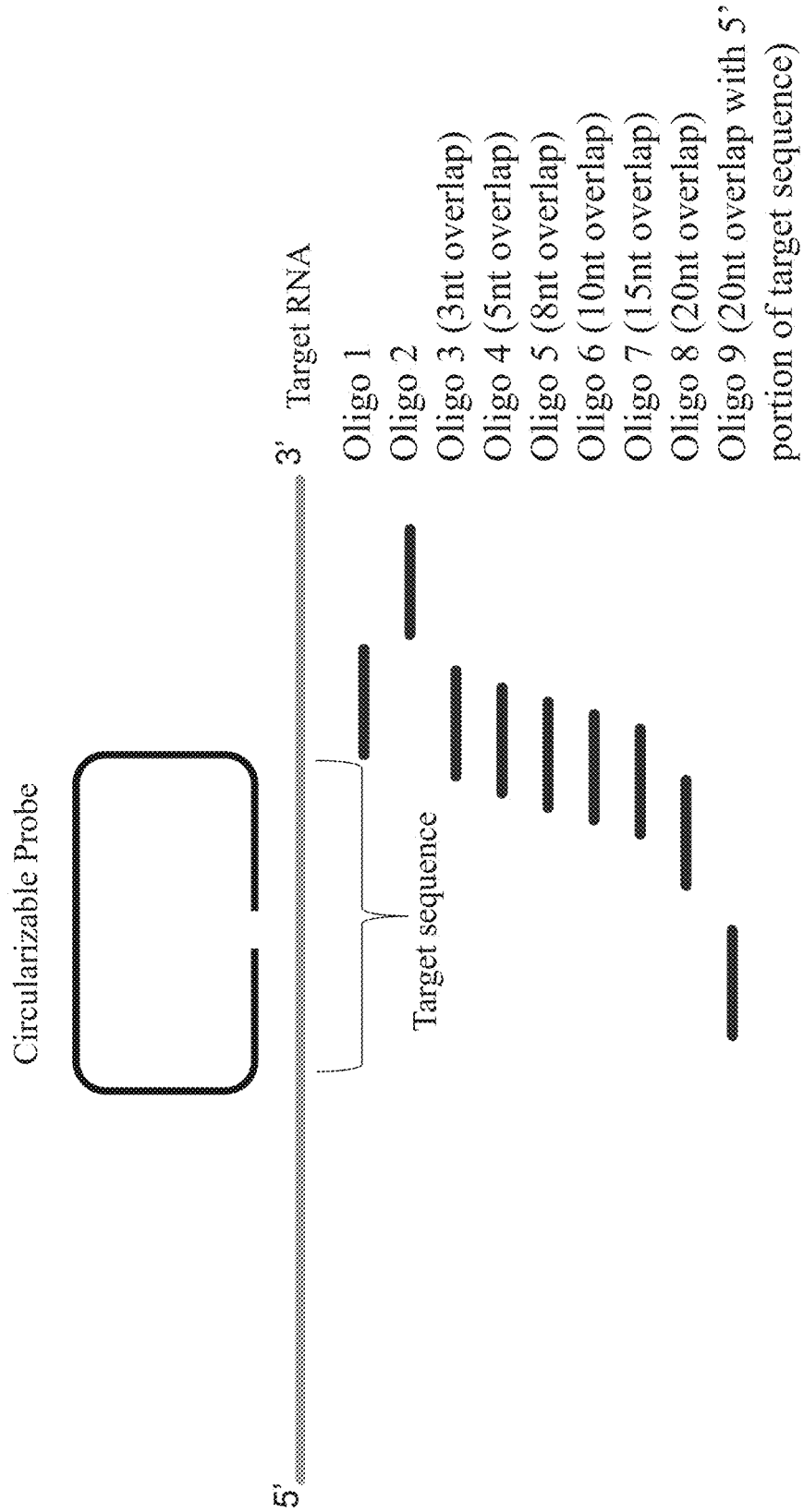
FIG. 2 provides a schematic illustration of the various nucleic acid oligonucleotides tested for RNase H cutting to facilitate target-primed RCA, and their overlaps with the target sequence for the circularizable probe tested.

For target-primed (primer-free) RCA experiments, a single-stranded DNA oligonucleotide complementary to an oligonucleotide hybridization region in Prox1 was contacted with the tissue section and allowed to hybridize. The tissue section was contacted with 1 U RNase H and incubated for 30 minutes at 37° C. in a buffer comprising magnesium chloride, potassium chloride, dithiothreitol (DTT), and Tris-HCL. The tissue section was washed to remove RNase H and DNA oligonucleotide. After the wash, the sample was immersed into a circularizable probe hybridization mixture including SSC and formamide and the circularizable (padlock) probe complementary to a target sequence in Prox1 and incubated. After that the section was washed. Following the washes performed after hybridization, ligation reaction mix including ligase buffer and ligase was added to the section. A wash was performed after the ligation. The tissue section was then immersed in rolling circle amplification mixture, containing Phi29 polymerase buffer, dNTPs, and Phi29 polymerase and incubated. Subsequently, the section was washed. The RCPs associated with Prox1 were then detected in the biological sample by hybridization of detectably labeled probes and imaging the biological sample. As shown in FIG. 2, DNA oligonucleotides (Oligo 1-9) were tested with varying degrees of overlap between the complementary oligonucleotide hybridization region in the target RNA and the target sequence for the circularizable probe in the target RNA. The tested DNA oligonucleotides were as shown in Table 1 below (illustrated schematically in FIG. 2):

TABLE 1

DNA oligonucleotide overlaps tested for RNase H cleavage and target-primed RCA.

| DNA Oligonucleotide | Description |
|---|---|
| Oligo 1 | oligonucleotide hybridization region adjacent to the 3' end of the padlock probe target sequence |
| Oligo 2 | oligonucleotide hybridization region 20 nucleotides downstream of the 3' end of the target sequence |
| Oligo 3 | 3 nucleotide overlap between the oligonucleotide hybridization region and the 3' end of the target sequence |
| Oligo 4 | 5 nucleotide overlap between the oligonucleotide hybridization region and the 3' end of the target sequence |
| Oligo 5 | 8 nucleotide overlap between the oligonucleotide hybridization region and the 3' end of the target sequence |
| Oligo 6 | 10 nucleotide overlap between the oligonucleotide hybridization region and the 3' end of the target sequence |

TABLE 1-continued

DNA oligonucleotide overlaps tested for
RNase H cleavage and target-primed RCA.

| DNA Oligonucleotide | Description |
|---|---|
| Oligo 7 | 15 nucleotide overlap between the oligonucleotide hybridization region and the 3' end of the target sequence |
| Oligo 8 | 20 nucleotide overlap between the oligonucleotide hybridization region and the 3' end of the target sequence |
| Oligo 9 | 20 nucleotide overlap between the oligonucleotide hybridization region and the 5' end of the target sequence |

For control (separate primer) RCA experiments, a circularizable probe was hybridized to the target RNA as described above and ligated, and the oligonucleotide hybridization and RNase H cleavage step were not carried out. The sample was then immersed in rolling circle amplification mixture with a separate RCA primer designed to hybridize to a primer region in the circularizable probe, Phi29 polymerase buffer, dNTPs, and Phi29 polymerase and incubated. Subsequently, the section was washed and the RCPs associated with Prox1 were detected in the biological sample by hybridization of detectably labeled probes and imaging the biological sample.

As an additional test condition, (separate primer with RNase H), RCA was tested in the presence of 1 U RNase H and a separate primer that hybridizes to the circularizable probe, but without a separate DNA oligonucleotide that hybridizes to the target RNA. For this additional control, the RNase H was present during the RCA. A circularizable probe was hybridized to the target RNA and ligated as described above. The sample was then contacted with rolling circle amplification mixture with the separate primer. RNase H, Phi29 polymerase buffer, dNTPs, and Phi29 polymerase, and incubated. Subsequently, the section was washed and the RCPs associated with Prox1 were detected in the biological sample by hybridization of detectably labeled probes and imaging the biological sample.

As an additional test condition (RNase H; no oligonucleotide and no separate primer), a primer-free RCA was tested in the presence of 0.1 U or 1 U RNase H but without adding a separate DNA oligonucleotide that hybridizes to the target RNA, or a separate primer that hybridizes to the circularizable probe. For this additional control, the RNase H was present during the RCA. A circularizable probe was hybridized to the target RNA and ligated as described above. The sample was then immersed in rolling circle amplification mixture, this time containing RNase H, Phi29 polymerase buffer, dNTPs, and Phi29 polymerase, and incubated. Subsequently, the section was washed and the RCPs associated with Prox1 were detected in the biological sample by hybridization of detectably labeled probes and imaging the biological sample.

Figure 3B:
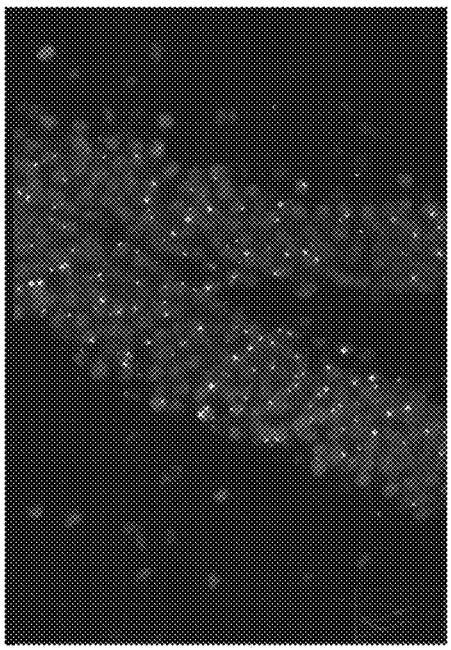
Figure 3D:
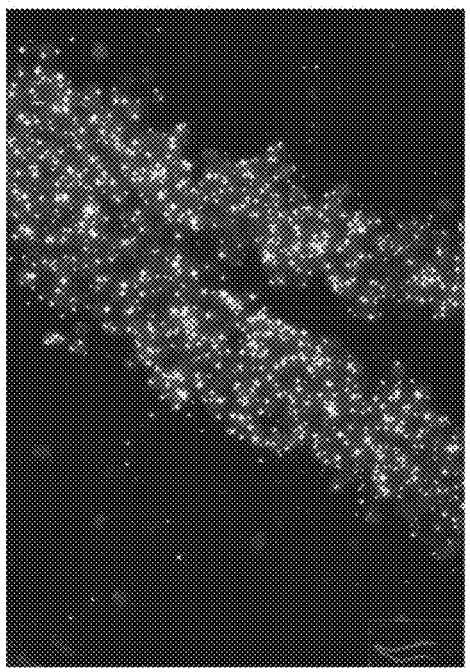
Figure 3A:
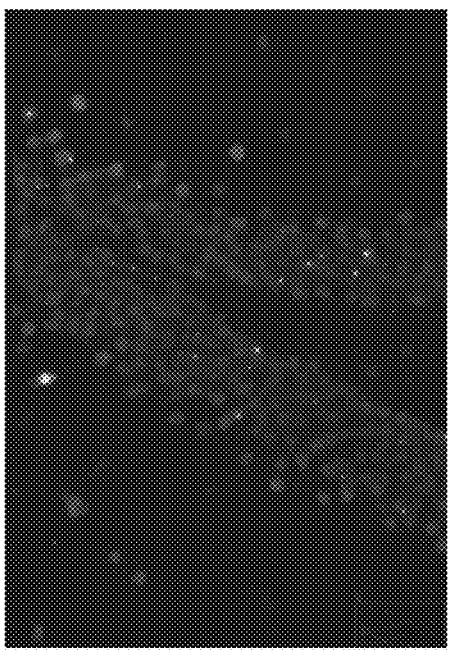
Figure 3C:
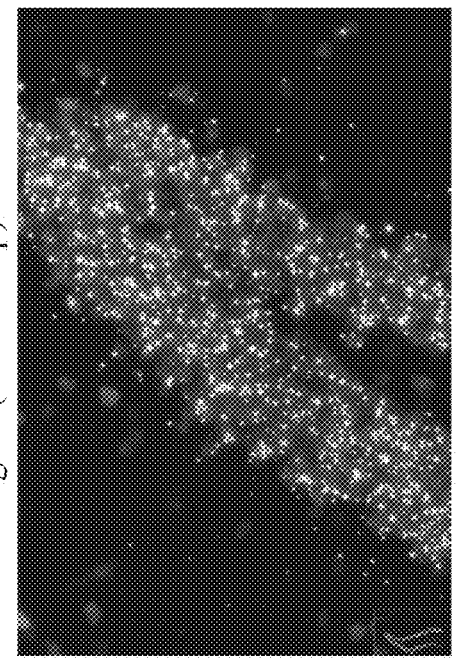
Figure 3F:
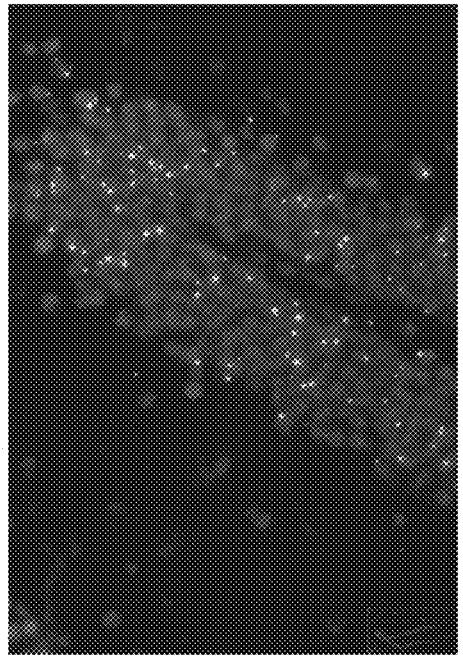
Figure 3E:
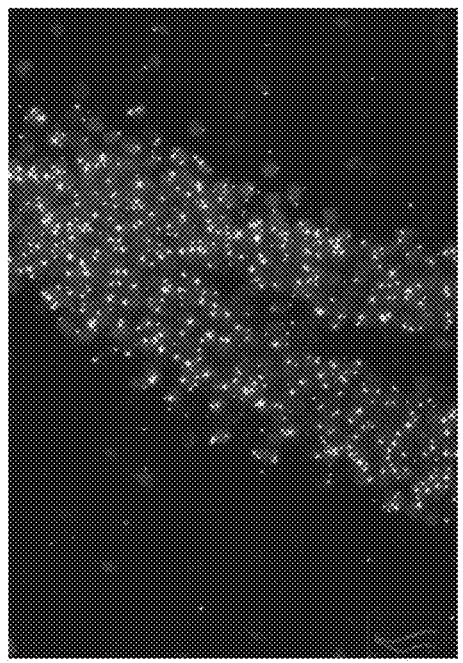

Results:

The total detected RCP counts for the Prox1 target RNA gradually increased as the overlap between the oligonucleotide hybridization region and the target sequence of the padlock probe increased from 0 to 8 or 10 nucleotide overlap. FIGS. 3A-3J are a fluorescent image of a mouse brain tissue section showing detected RCPs using the indicated oligonucleotides for target-primed RCA, or for the control with a separate primer and no RNase H (FIG. 3G), RNase H present during RCA with no separate oligonucleotide and with a separate primer (FIG. 3H), RNase H present during RCA with no separate oligonucleotide and no separate primer FIGS. 3I and 3J). As can be seen by comparing FIGS. 3A-3J, the best results (greatest signal intensity and number of RCPs detected) were obtained with an overlap of about 8-10 nucleotides between the oligonucleotide hybridization region and the target sequence (Oligo 5 and Oligo 6). After that, further increases in the overlap between the oligonucleotide hybridization region and the target sequence reduced the signal intensity and/or number of detected RCPs (FIGS. 3E-3F). Generally, the RCP homogeneity seemed to be improved for target-primed RCA relative to the control (separate primer, FIG. 3G) conditions. The target-primed (primer-free) RCA conditions also seemed to have fewer nonspecific blobs detected outside desired tissue area.

When RNase H was introduced during the RCA process (separate primer with RNase H), the RCP counts and intensity increased compared to control (separate primer). When RNase H was introduced during the RCA process without a separate primer or a nucleic acid oligonucleotide step (RNase H; no oligonucleotide and with separate primer, FIG. 3H), fewer RCP spots were observed. Without being bound by theory, this may be because Phi29 needs to wait until some RNase H cuts the mRNA at the correct position, then use the cleaved RNA to initiate the RCA. When higher concentrations of RNase H were used, fewer RCP spots were observed. Without being bound by theory, this may be because RNase cuts too much at higher concentrations, so that the circularized probes may no longer be localized at the target RNA, thus, reducing the number of RCPs that can be produced and/or observed.

Example 2: Target-Primed RCA (tpRCA) Improves Sensitivity, Signal Intensity and RCP Homogeneity with Various Durations of RCA This example demonstrates the unexpected benefits of target-primed RCA at various different RCA durations. RCA incubation times of 10 minutes, 30 minutes, 60 minutes, and 120 minutes were tested. Oligo 5 (8 nucleotide overlap between the oligonucleotide hybridization region and the 3' end of the target sequence) was used for each different incubation time.

Methods

For target-primed (primer-free) RCA experiments, a single-stranded DNA oligonucleotide complementary to an oligonucleotide hybridization region in Prox1 was contacted with the tissue section and allowed to hybridize. The tissue section was contacted with 1 U RNase H and incubated for 30 minutes at 37° C. in a buffer comprising magnesium chloride, potassium chloride, dithiothreitol (DTT), and Tris-HCL. The tissue section was washed to remove RNase H and DNA oligonucleotide. After the wash, the sample was immersed into a circularizable probe hybridization mixture including SSC and formamide and the circularizable (padlock) probe complementary to a target sequence in Prox1 and incubated. For this experiment, the oligonucleotide was Oligo 5, with an 8 nucleotide overlap between the oligonucleotide hybridization region and the 3' end of the target sequence. After that the section was washed. Following the washes performed after hybridization, ligation reaction mix including T4 ligase buffer and T4 ligase was added to the section. The tissue section was then immersed in rolling circle amplification mixture, containing Phi29 polymerase buffer, dNTPs, and Phi29 polymerase and incubated for 10 minutes, 30 minutes, 60 minutes, or 120 minutes at 30° C. Subsequently, the section was washed. The RCP associated with Prox1 was then detected in the biological sample by hybridization of detectably labeled probes and imaging the biological sample.

For control (separate primer) RCA experiments, a circularizable probe was hybridized to the target RNA and ligated as described above. The sample was then immersed in rolling circle amplification mixture, this time containing a separate RCA primer designed to hybridize to a primer region in the circularizable probe, Phi29 polymerase buffer, dNTPs, and Phi29 polymerase and incubated for 10 minutes, 30 minutes, 60 minutes, or 120 minutes. Subsequently, the section was washed and the RCPs associated with Prox1 were detected in the biological sample by hybridization of detectably labeled probes and imaging the biological sample.

Additional test conditions were also performed as described above (RNase H with no oligonucleotide and no separate primer; or separate primer with RNase H). RCA without RNase H or a separate primer was tested as a negative control.

Results

Signal intensity of the detected RCPs were lower for the 10 minute RCA duration, but target-primed RCA produced more detectable RCP spots (higher sensitivity) and higher signal intensity compared to control with 10 minutes RCA. With 30 minutes RCA, signal intensity was higher, and target-primed RCA again resulted in more detectable RCP spots (higher sensitivity) and higher signal intensity compared to control.

FIGS. 4A-4H show the sigma (size) and amplitude (signal intensity) distributions for double positive detected RCPs ("DP blobs") and false positives ("FP blobs") detected using each of the indicated target-primed or control (separate primer) RCA conditions. At shorter time points (10 minutes and 30 minutes), target-primed RCA produced smaller and narrower RCP spots (FIG. 4B, showing 10 minutes target-primed RCA, and FIG. 4D, showing 30 minutes target-primed RCA) compared to control (separate primer, no RNase H) (FIG. 4A, showing 10 minutes control RCA, and FIG. 4B, showing 30 minutes control RCA). By around 1 hour RCA duration, the RCP spot sizes were comparable for target-primed RCA (FIG. 4F) and control (FIG. 4E), but were still smaller than for the control RCA conditions (separate primer, no RNase H) with a 2 hour RCA incubation (FIG. 4G). Collectively, these results demonstrate the advantages of target-primed RCA for increased sensitivity and increased signal intensity relative to RCA using a separate primer.

Figure 5A:
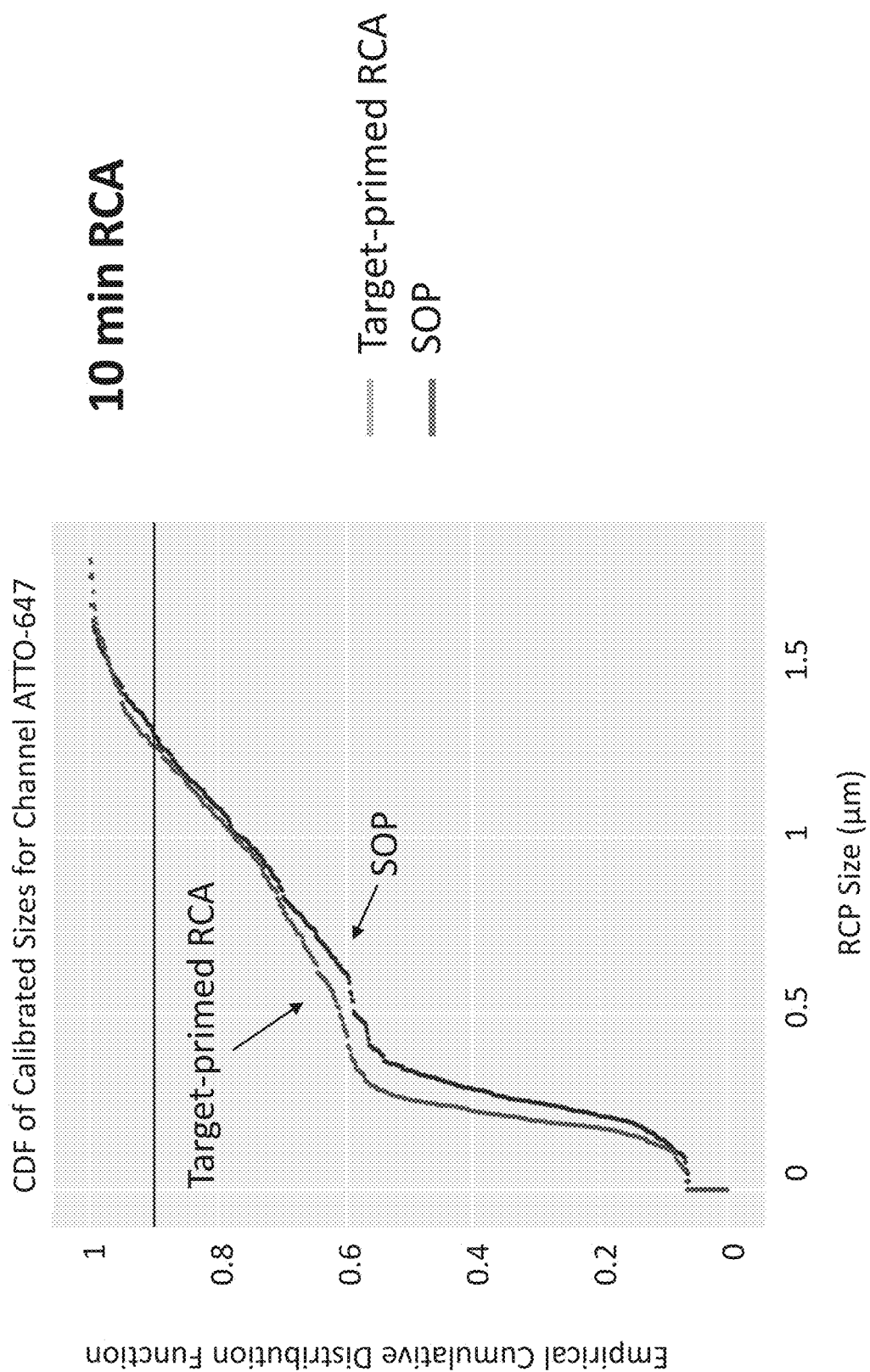
FIGS. 5A-5C provide cumulative distribution function curves for detected RCP sizes for target-primed RCA compared to control with 10 minutes, 30 minutes, or 1 hour RCA incubation.
Figure 5B:
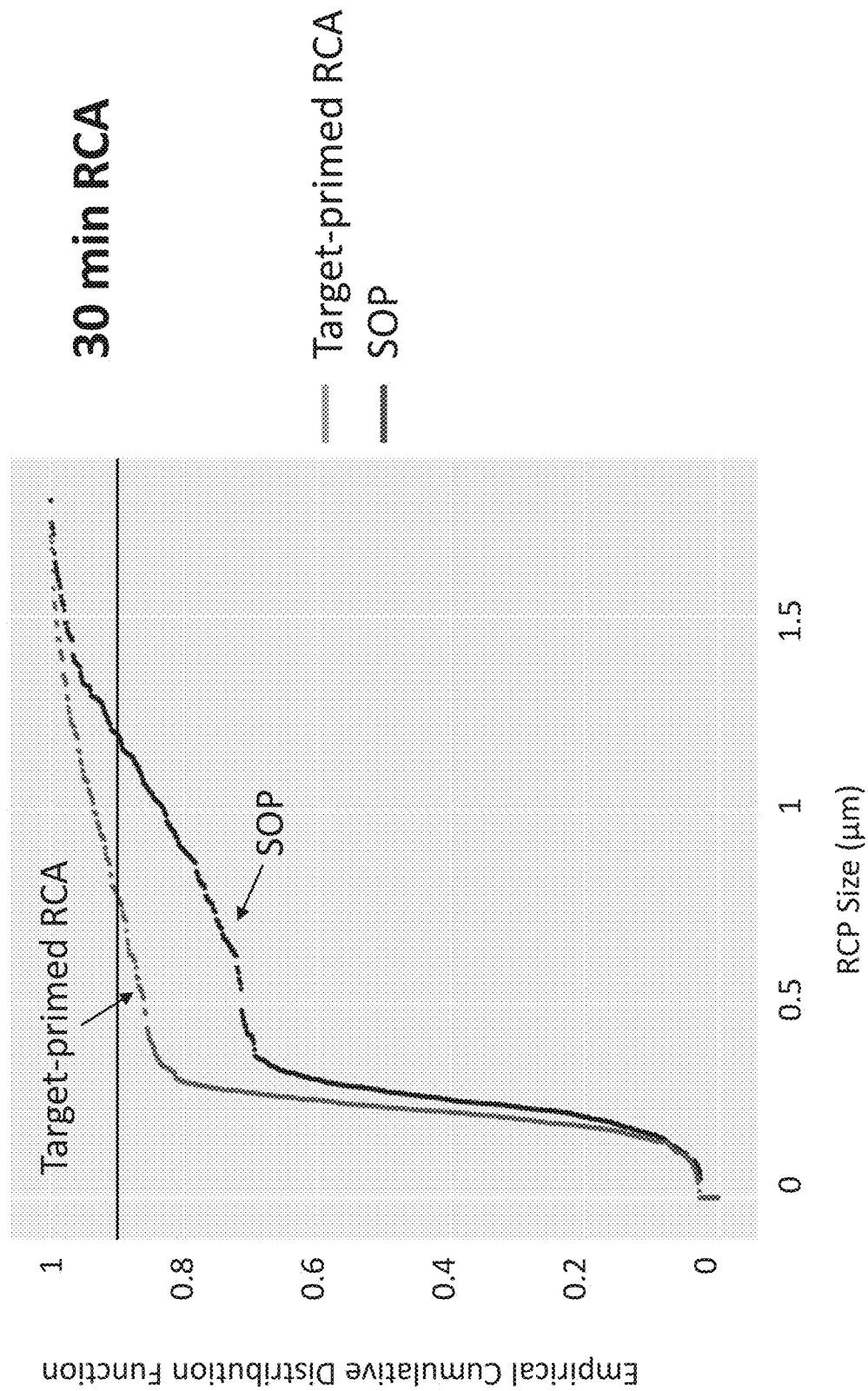
Figure 5C:
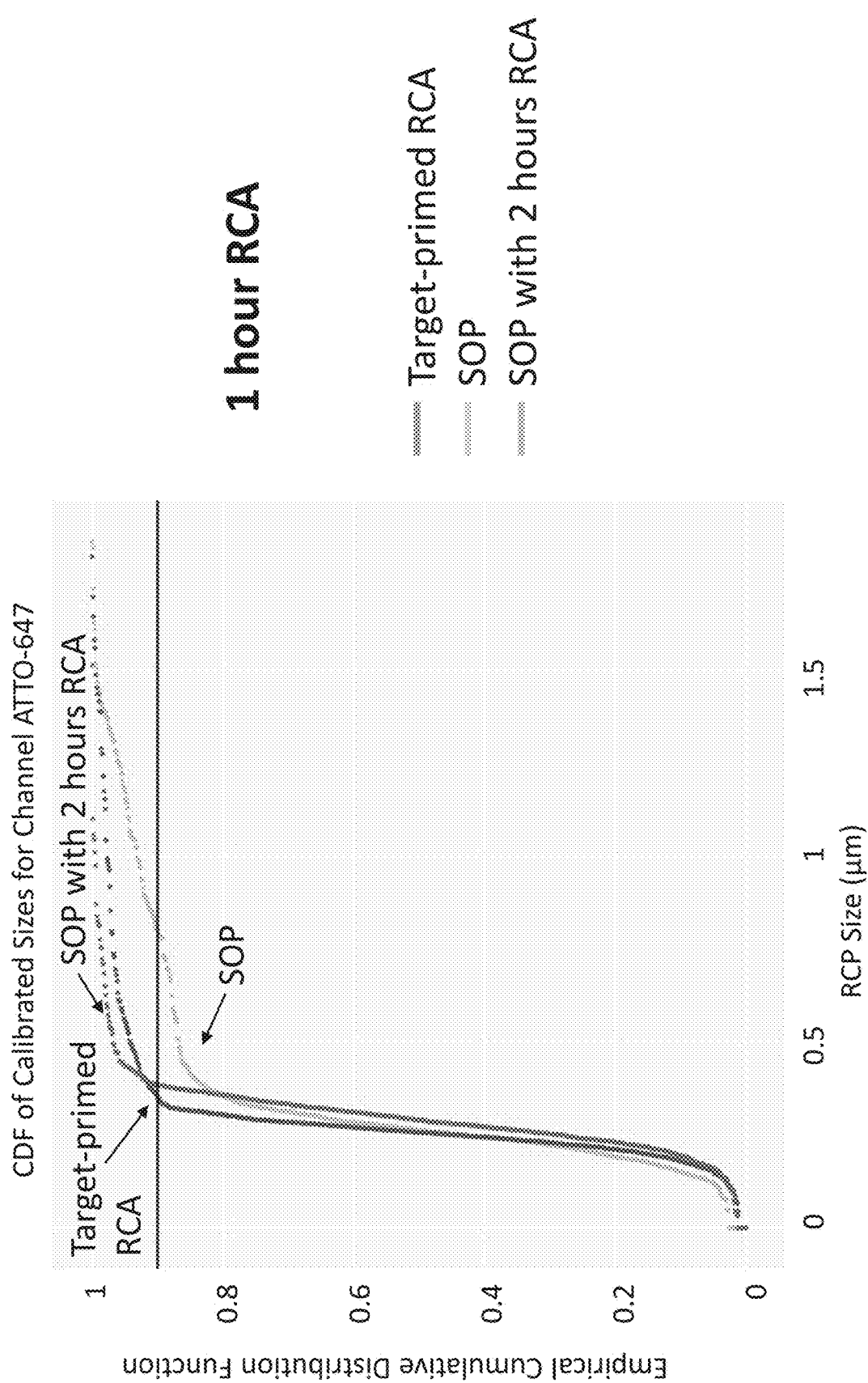

Notably, target-primed RCA provided RCPs with a narrower distribution in sigma (size) in all conditions that have a RCA duration less than two hours (see FIGS. 5A-5C, providing cumulative distribution function curves for detected RCP sizes for target-primed RCA compared to control with 10 minutes, 30 minutes, or 1 hour RCA incubation). The target-primed RCPs were brighter than the control RCPs, and the signal intensity distribution was also narrower. Double positive counts for RCPs produced using target-primed RCA was around 3-5 times of that of control with the same RCA duration, across conditions. Also notably, 30 minute incubation for target-primed RCA already produced a similar number of double positive counts for RCPs as the positive control (separate primer, no RNase H) with two hours RCA incubation. In some cases, such benefits may be due to target-primed RCA allowing more efficient and/or uniform amplification as the substrate (e.g., circularized probe) is in a relaxed state as compared to amplification performed with a separate primer where the RNA is interlocked with circularized probe, which may provide a more constrained substrate slowing down the polymerase.

Without performing a separate step for RNA cleavage using a nucleic acid oligonucleotide and RNase H, adding RNase H during the RCA step (2h) yielded a similar pattern as target-primed RCA (RNase H with no oligonucleotide and no separate primer). But the sigma (size) had a wider distribution compared to target-primed RCA using a nucleic acid oligonucleotide for RNase H cutting.

As expected, negative control (no primer and no RNase H) did not produce a significant number of detected fluorescent spots.

Example 3: Target-Primed RCA (tpRCA) with $Ca^{2+}$ Synchronization of Polymerase Activity This example provides results demonstrating that $Ca^{2+}$ synchronization of polymerase activity improves signal intensity compared to non-synchronized target-primed RCA under the same conditions.

Target-primed RCA (tpRCA) was performed as described in Example 2 above, except that the Phi29 polymerase was initially contacted with the sample in an "OFF" buffer comprising dNTPs and $Ca^{2+}$, a dication that is not a cofactor of the polymerase. The sample was then contacted with an "ON" buffer comprising dNTPs and $Mg^{2+}$, a dication that is a cofactor of the polymerase.

Figure 6:
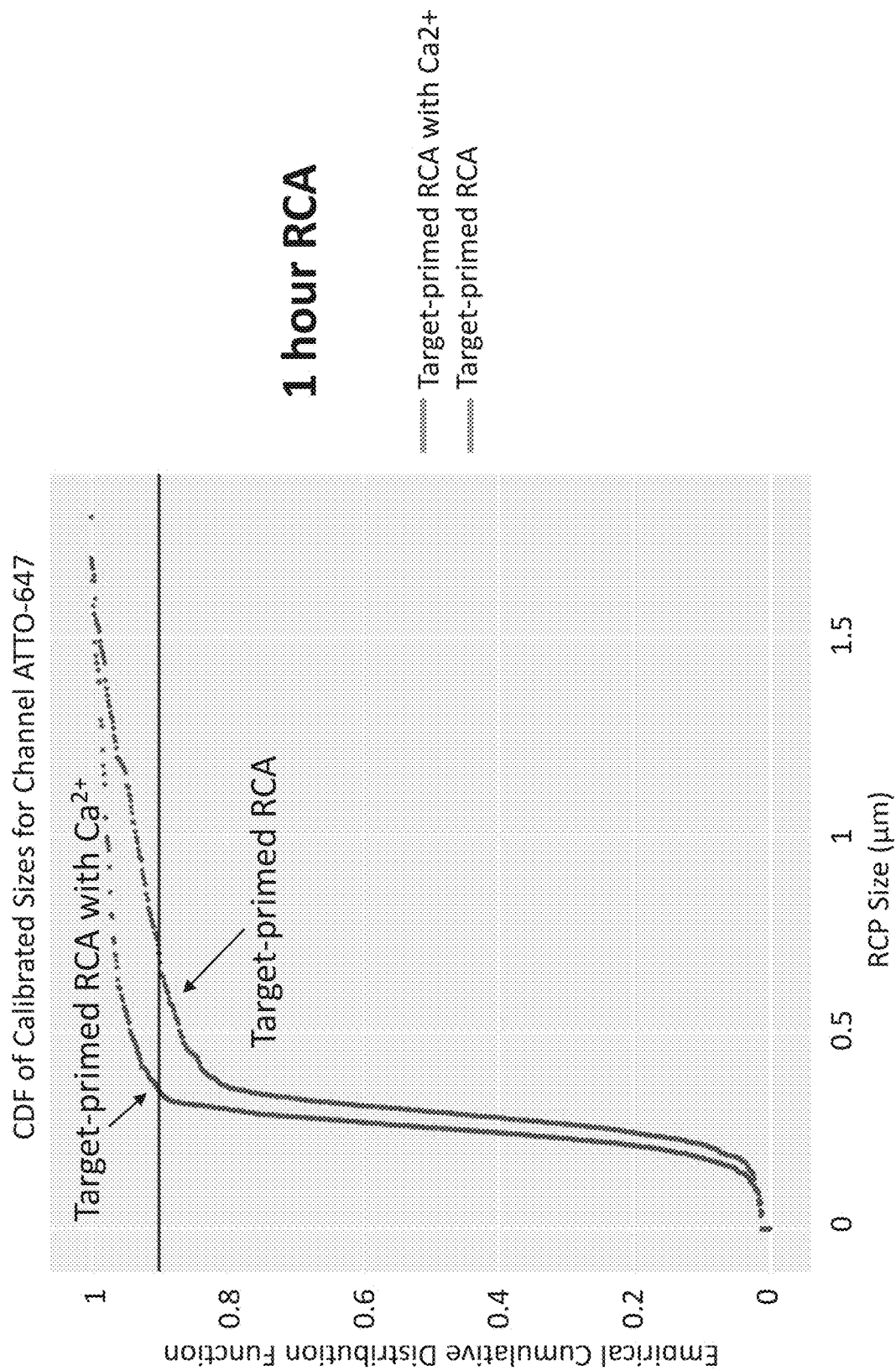
FIG. 6 provides cumulative distribution function curves for detected RCP sizes for target-primed RCA with or without $Ca^{2+}$ synchronization.
Figure 7B:
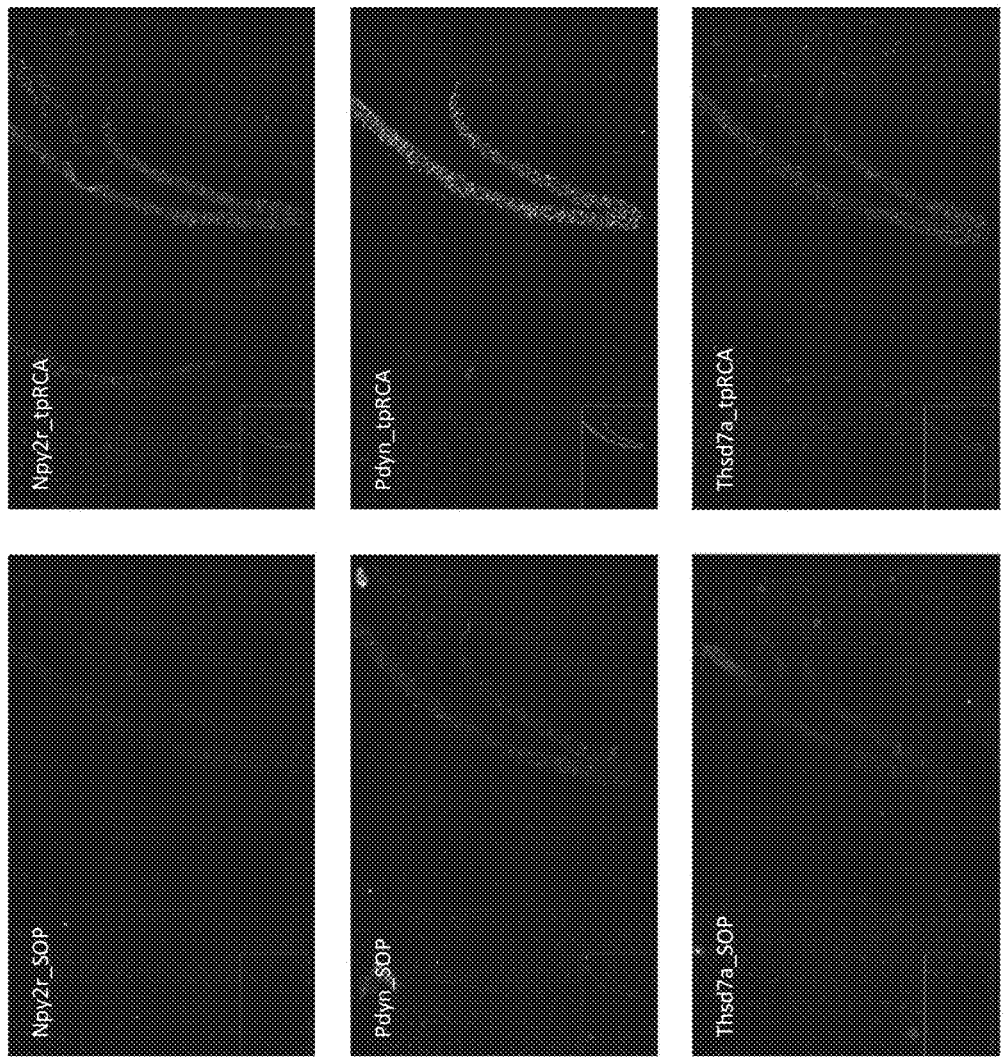
Figure 8:
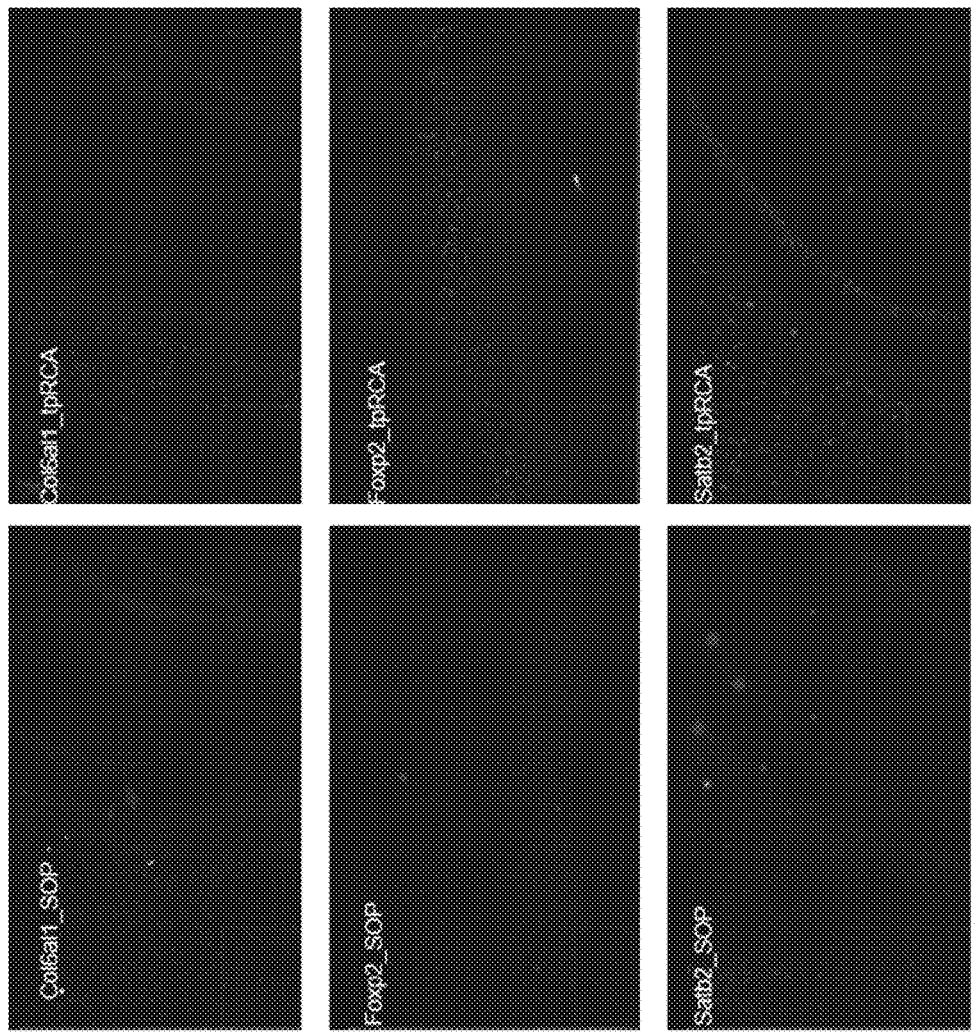
FIG. 8 provides fluorescent images of mouse brain tissue sections showing the results of target-primed RCA compared to control (separate primer) for detection of a panel of genes in the cortex, detected using a single probe per target RNA.
Figure 9:
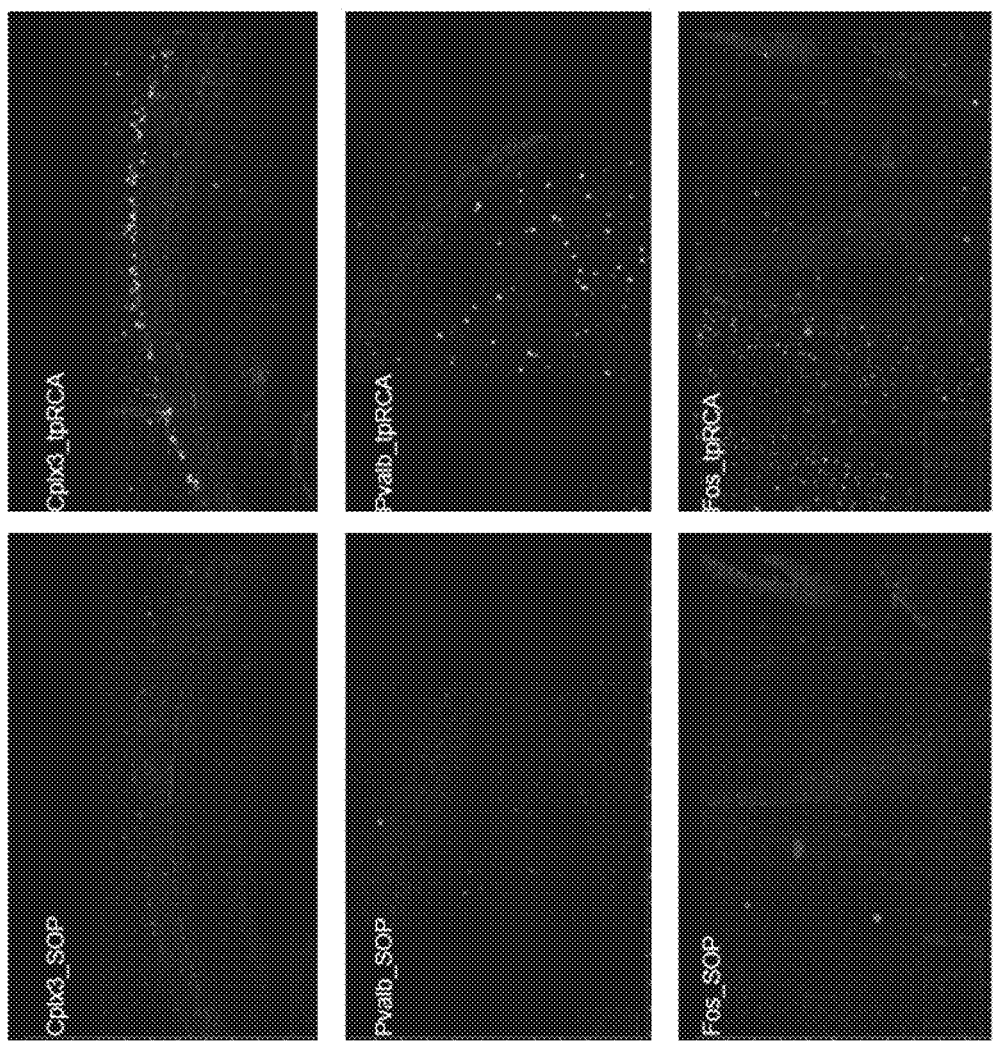
FIG. 9 provides fluorescent images of mouse brain tissue sections showing the results of target-primed RCA compared to control (separate primer) for detection of a panel of genes in the cortex, detected using a single probe per target RNA.

Compared to target-primed RCA performed under the same conditions but without $Ca^{2+}$ synchronization, the synchronization resulted in higher brightness, slightly more counts, and a larger size for detected RCPs (FIG. 6).

Example 4: Target-Primed RCA (tpRCA) Detection of a Panel of 12 Different Target RNAs This example demonstrates the advantages of target-primed RCA for detection of a panel of 12 different genes, detected using a single probe per target RNA. Six of the genes (Bdnf, Npy2r, Pde7b, Pdyn, Rasgrf2, and Thsd7a) are mainly expressed in the dentate gyrus (DG), and six of the genes (Col6a11, Cplx3, Foxp2, Pvalb, Satb2, and Fos) are mainly expressed in Cortex.

Mouse brain tissue sections were provided on an optically transparent substrate as described in Example 1 above. Individual tissue sections were each contacted with one of 12 different circularizable probes corresponding to the panel of 12 different target RNAs. RCA using a separate primer without adding RNase H ("Control," labeled "SOP" in FIGS. 7A-7B and FIGS. 8-9) was performed for 2 hours as described in Example 1. Target-primed RCA was also performed for 2 hours. Nucleic acid oligonucleotides having 8 nt overlap with the circularizable probe were tested for all 12 genes.

Overall, compared to Control, tpRCA has brighter signal, as demonstrated by an upshift in the distribution of signal amplitude for detected RCA products. The increase in signal amplitude is more pronounced for some genes than for others (ranging from ~0% to ~300% increase in signal intensity), as can be seen in FIGS. 7A-7B and FIGS. 8-9. Additionally, tpRCA had a higher signal-to-noise ratio (SNR) than Control, ranging from a ~0% to ~90% increase.

The sigma distribution was tighter in tpRCA compare to Control, to different degrees for different genes. These results demonstrate that tpRCA provided more uniform RCP size compared to Control. At two hours RCA, tpRCA resulted in a larger average RCP size than Control, ranging from ~0% to ~70% increase for a majority of the genes.

To evaluate sensitivity of target detection, the total number of detected RCP counts was analyzed for tpRCA compared to Control. For most genes tested, target-primed RCA ("tpRCA") resulted in more double positive RCP counts ("DP blob counts") compared to Control. For both tpRCA and Control, the expression patterns detected for the 12 genes in the dentate gyrus were as expected, demonstrating that tpRCA provides good specificity. For example, Cplx3, Foxp2, and Pvalb were not detected in the dentate gyrus.

Example 5: Target-Primed RCA Detection with Multiple Nucleic Acid Oligonucleotides Per Target RNA This example demonstrates the use of multiple nucleic acid oligonucleotides to cleave each target RNA for detection of 6 tested different genes such that each gene can be detected using multiple probes per target RNA. The six tested genes were Cplx3, Prox1, Wfs1, Pvalb, Igf2, and Thsd7a. The purpose is to test the limit of tpRCA and determine the minimal distance between the oligonucleotide hybridization regions for two nucleic acid oligonucleotides without losing the target mRNA fragments (e.g., after cleavage), and thus without losing sensitivity.

Figure 10:
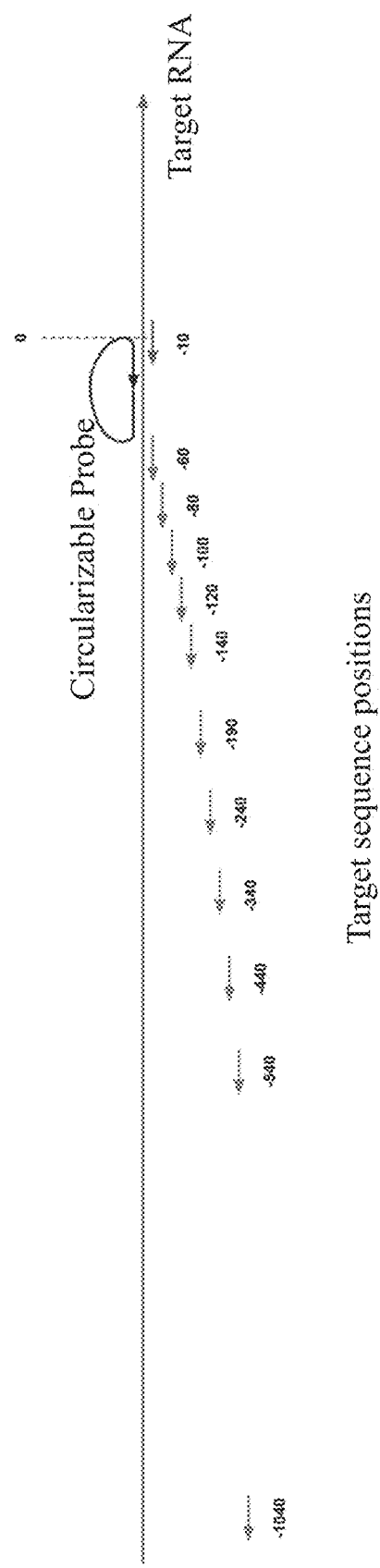
FIG. 10 provides a schematic illustration of the various nucleic acid oligonucleotides positions for RNase H cutting to test the limits of target-primed RCA.

Each gene was detected separately on mouse brain tissue sections provided on an optically transparent substrate as described in Example 1 above. The sections were contacted with a nucleic acid oligonucleotide at the −10 position (having 10 nt overlap with the circularizable probe) and an additional nucleic acid oligonucleotide at a position from −60 to −1040 position as illustrated in FIG. 10. RCA performed without adding RNase H either with or without a separate primer (labeled "SOP") was performed for 2 hours as described in Example 1. Target-primed RCA was also performed for 2 hours.

RCP counts were detected using the various nucleic acid oligonucleotide positions indicated in FIG. 10 for performing target-primed RCA. Overall, among six genes tested, the additional nucleic acid oligonucleotide targeting 200-300 nt from the nucleic acid oligonucleotide was observed to be the minimal distance between the two cutting sites. In some cases, probes closer than about 300 nucleotides apart may result in loss of mRNA and affect sensitivity of the detection. With the nucleic acid oligonucleotide at a distance of >500 nt distance between two nucleic acid oligonucleotides, some variable detection levels were observed and may be due to non-specificity and potentially cleaving at unexpected locations or cleaving at specific positions that disturb secondary structures.

Example 6: Detection of Signal Mislocalization

This example describes an experiment performed to test specificity and mislocalization of signals in a sample where RCA was performed using an added primer ("SOP") compared to target-primed RCA using nucleic acid oligonucleotides for cleavage.

Samples were prepared containing either pure GFP cells, pure RFP cells, a mixture of GP and RFP cells at different ratios. GFP or RFP transcripts were detected using a single probe per target. Target-primed RCA was performed using nucleic acid oligonucleotides having 10 nt overlap with the circularizable probe. In this experiment, GFP transcripts are only expected in GFP cells and RFP transcripts are only expected in RFP cells. The detection of GFP transcripts in RFP cells would indicate that non-specific binding, ligations, or ligation of the circularizable probe has occurred or that the detected signal is associated with a generated product (RCP) that has been mislocalized throughout the assay. The detection of either GFP or RFP transcripts outside the cells suggests a mislocalization of a generated product (RCP).

In a sample where the cells are diluted at the ratio of 9:1 for GFP:RFP cells to reduce the effect of the highly clustered cells, signals associated with RFP transcripts were assessed and a ratio was calculated to determine the signal mislocalization rate=RFP probes inside all cells/RFP probes outside of all cells. This ratio represents the signal mislocalized from inside the cells to outside the cell. As shown in Table 2, for the samples where RCA was performed using an added primer, the calculated ratio is 23.19 (for every 23 double positive (DP) blobs detected inside the cells, there is 1 DP blob mis-localized to outside of the cells) compared to 190.12 (for every 190 DP blobs we detected inside the cells, there is 1 DP blob mislocalized to outside the cells) for target-primed RCA samples indicating much fewer signals are mislocalized in tpRCA condition. These results are consistent with target priming being able to reduce signal mislocalization since the generated amplification product is securely held in place since it is generated using the target as primer whereas an external primer may not remain bound via hybridization to the target throughout the detection assay.

TABLE 2

| | Signal Mislocalization Rate | | |
|---|---|---|---|
| Sample | Ratio | DP in cells | DP outside cells |
| SOP - with primer | 23.19 | 5845.0 | 252.0 |
| Target primed | 190.12 | 3042.0 | 16.0 |

Figures 11A, 11B:
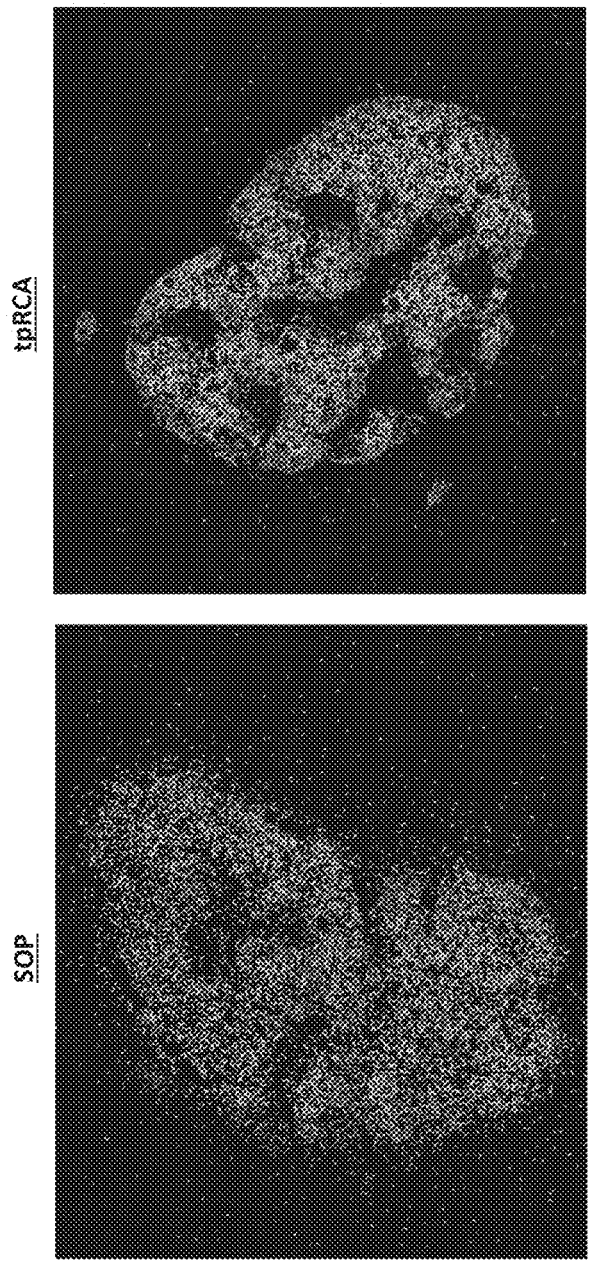
FIGS. 11A-11B provide fluorescent images of human pancreas tissue sections showing the results of target-primed RCA compared to control (separate primer) for detection of a panel of 1,000 genes.
Figure 11D:
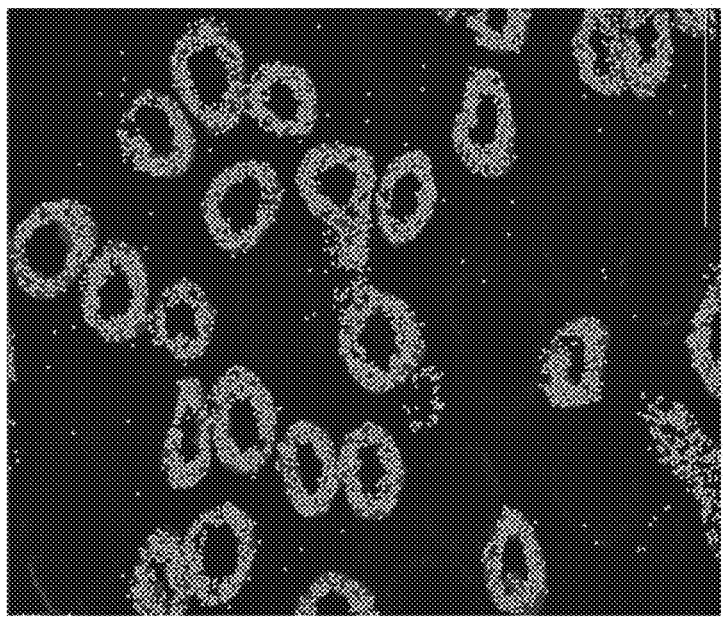
FIGS. 11C-11D provide fluorescent images of human kidney tissue sections showing the results of target-primed RCA compared to control (separate primer) for detection of a panel of 5,000 genes.
Figure 11C:
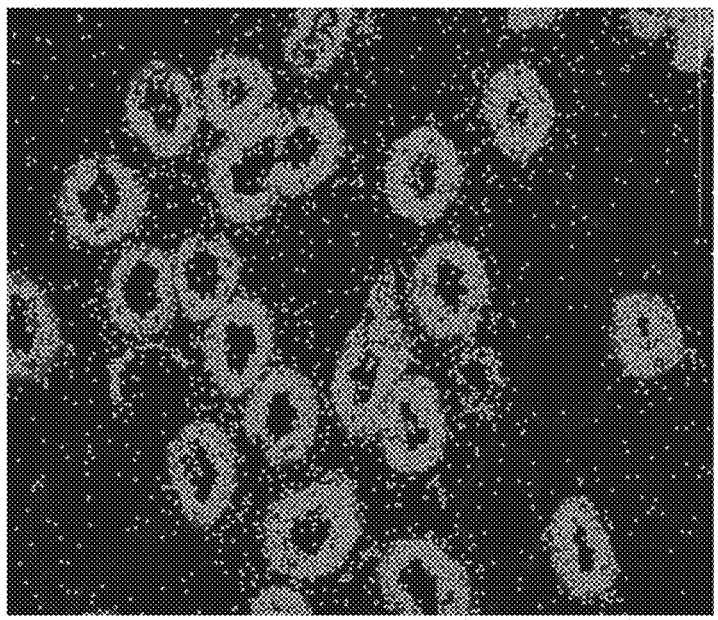

Assay specificity and mislocalization of signals were evaluated in samples where RCA was performed using an added primer ("SOP") compared to target-primed RCA using nucleic acid oligonucleotides for cleavage, for detection of a panel of 1,000 genes in various human tissue samples using a tissue array sample (including lung, skin, colon, pancreas, and liver, and kidney). As an example, signals associated with DAPI, insulin (INS) as a marker for endocrine beta cells, and glucagon (GCG) as a marker for endocrine alpha cells were detected (FIG. 11A and FIG. 11B) in a pancreatic endocrine islet in the human pancreas tissue sections. Comparing the two images in FIG. 11A and FIG. 11B, target priming (FIG. 11B) was observed to improve specificity, reduce signal mislocalization and allow for improved assignment of detected transcripts to cells. For example, in FIG. 11A, mislocalized transcripts may not be assigned to cells with proper cell segmentation. Similar increased specificity and reduced signal mislocalization were observed across the various tissue samples tested and for detection of a panel of 5,000 genes in various human FFPE tissue array samples. For example, results from an FFPE human kidney sample showed signal mislocalization in SOP RCA conditions (FIG. 11C) compared to target-primed RCA (FIG. 11D).

Example 7: Phosphatase (PNK)-Treated RNA for Target-Primed RCA Detection

This example demonstrates the benefits of polynucleotide kinase (e.g., T4 PNK) treatment to repair RNA before target-primed RCA. RNases may be present in the biological sample during the assay or prior to the assay and digest target RNAs and leave 3' phosphates. In some cases, chemical degradation can cause damage (e.g., to target RNAs) in ambient conditions. One way to circumvent this issue is to include a phosphatase treatment step to repair and leave 3' OH groups for phi29 to initiate from for target primed RCA.

Target-primed (primer-free) RCA was performed essentially as described in Example 4, in addition, some of the biological samples were treated after RNase H cleavage with T4 PNK (in a MES buffer comprising $MgCl_2$) prior to hybridization of the circularizable probe. Following hybridization, ligation of the circularizable probes was performed and the sample was then immersed in rolling circle amplification mixture and incubated at 30° C. for 1.5 hours. Subsequently, the section was washed and the generated RCPs were detected in the biological sample by hybridization of detectably labeled probes and imaging the biological sample.

Figure 12:
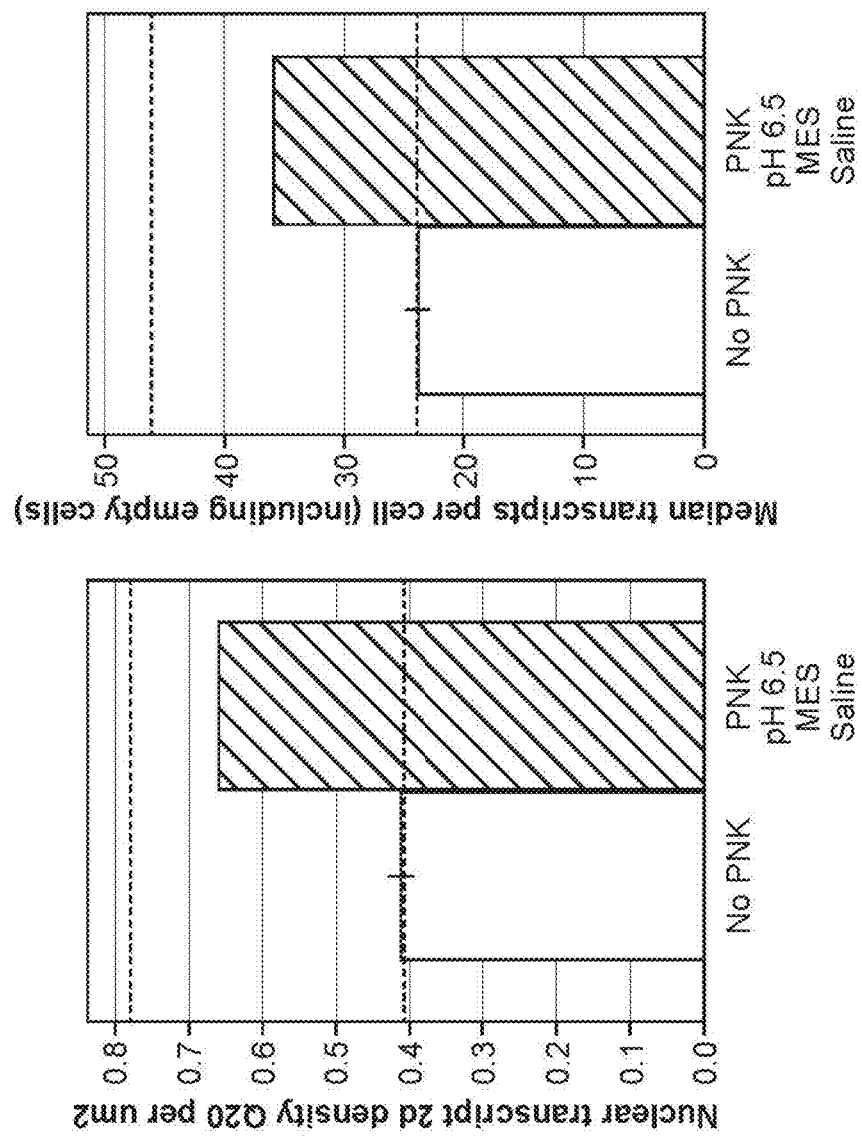
FIG. 12 provides the results of target-primed RCA performed on samples prepared with and without PNK treatment.

Overall, as shown in FIG. 12, compared to Control without PNK treatment, target-primed (primer-free) RCA performed on samples that were treated with T4 PNK showed increased sensitivity in FFPE tissue samples.

Example 8: Target-Primed RCA with Polymerase Synchronization

This example provides results demonstrating that synchronization of polymerase activity improves assay sensitivity compared to non-synchronized target-primed RCA under the same conditions. An assay for detecting a panel of 377 genes was performed on human pancreas tissue samples.

Target-primed RCA was performed as described in Example 3 above. After ligation of the circularized probes to form circular templates for RCA, the Phi29 polymerase was initially contacted with the sample in an "OFF" buffer comprising dNTPs and calcium $CaCl_2$ (a dication that is not an enzymatic cofactor of the polymerase) and incubated at 4° C. for 2 hours. The "OFF" buffer mixture was then removed and a buffer containing no Phi29 enzyme and no metals was added to the sample. This wash buffer was removed from the sample, and the sample was then contacted with an "ON" buffer comprising dNTPs and $Mg^{2+}$, and incubated for 1 hour at 30° C.

Figure 13:
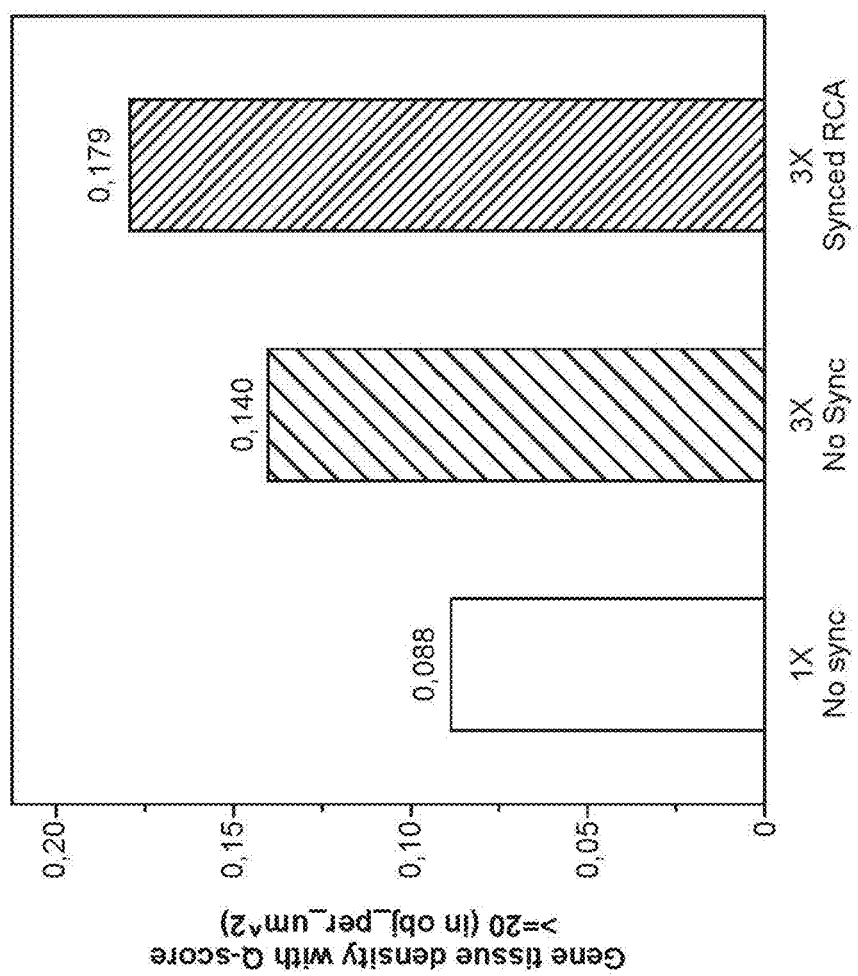
FIG. 13 provides a graph of gene tissue density showing the results of synchronized target-primed RCA (with $CaCl_2$) compared to target-primed RCA performed without synchronization.
Figure 14:
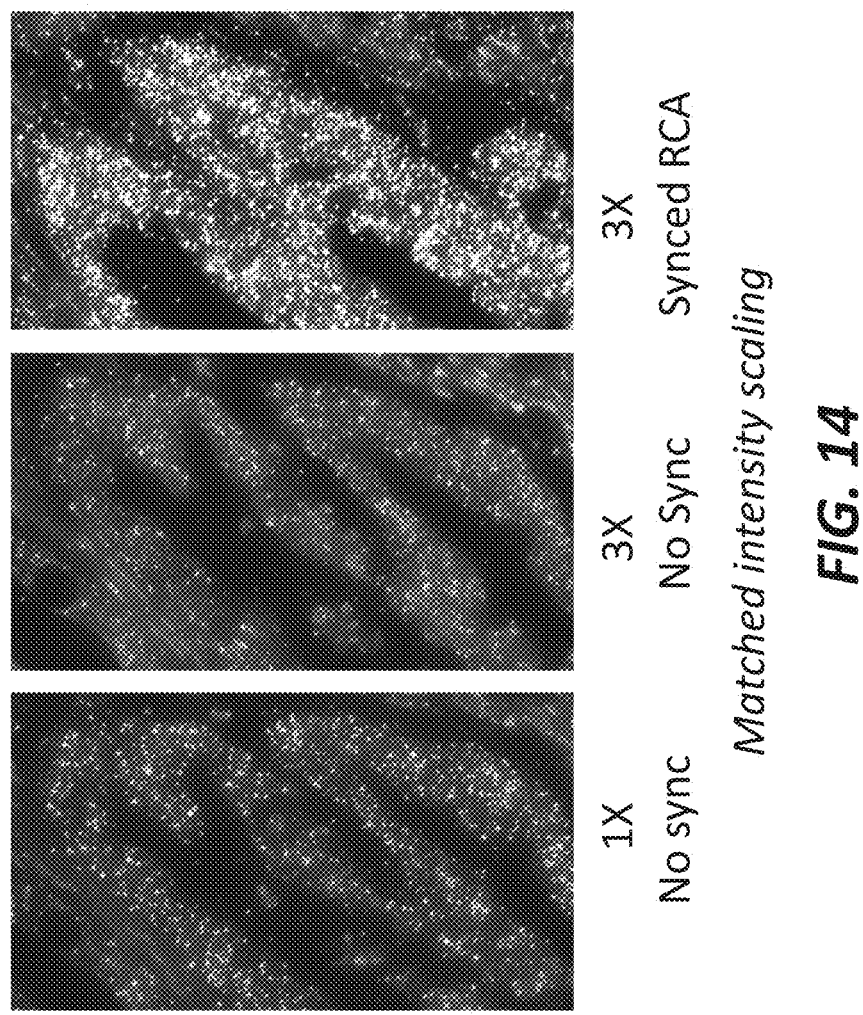
FIG. 14 provides fluorescent images of human pancreas tissue sections showing the results of synchronized target-primed RCA (with $CaCl_2$) compared to target-primed RCA performed without synchronization.

Overall, as shown in FIG. 13 and FIG. 14, compared to Control without a synchronization procedure (performed with 1× and 3× Phi29 enzyme), the synchronized target-primed (primer-free) RCA samples (performed with 3× Phi29 enzyme) showed an increase in RCP intensity and assay sensitivity. Similar observations were made in an experiment comparing synchronized RCA and RCA performed without synchronization on a tissue array sample with brain, heart, colon, pancreas, lymph node, liver and kidney samples and using strontium $SrCl_2$ instead of calcium in the "OFF" buffer.

The present disclosure is not intended to be limited in scope to the particular disclosed embodiments, which are provided, for example, to illustrate various aspects of the present disclosure. Various modifications to the compositions and methods described herein will become apparent from the description and teachings herein. Such variations may be practiced without departing from the true scope and spirit of the disclosure and are intended to fall within the scope of the present disclosure.

The invention claimed is:

1. A method of analyzing a biological sample, comprising:
   a) hybridizing a nucleic acid oligonucleotide to an oligonucleotide hybridization region in a target ribonucleic acid (RNA) in the biological sample, wherein the oligonucleotide hybridization region is adjacent to the 3' end of a target sequence in the target RNA or is overlapping with the 3' end of a target sequence in the target RNA;
   b) cleaving the target RNA with an RNase H in the oligonucleotide hybridization region to generate a cleaved target RNA, wherein the cleaved target RNA comprises at least a portion of the target sequence;
   c) subsequent to b), hybridizing a circular probe or a circularizable probe or probe set to the cleaved target RNA, wherein the circular probe or circularizable probe or probe set comprises a target recognition sequence complementary to the target sequence;
   d) performing rolling circle amplification of the circular probe or of a circularized probe generated from the circularizable probe or probe set to generate a rolling circle amplification product (RCP) using the cleaved target RNA as a primer; and
   e) detecting the RCP in the biological sample.

2. The method of claim 1, wherein the biological sample is contacted with the nucleic acid oligonucleotide and with the RNase H simultaneously before contacting the biological sample with the circular probe or the circularizable probe or probe set.

3. The method of claim 1, wherein the method comprises washing the biological sample after cleaving the target RNA with the RNase H and before contacting the biological sample with the circular probe or the circularizable probe or probe set.

4. The method of claim 1, wherein the oligonucleotide hybridization region and the target sequence overlap by between 1 and 20 nucleotides.

5. The method of claim 1, wherein the method does not comprise contacting the biological sample with a DNA primer that hybridizes to the circular probe or the circularized probe.

6. The method of claim 1, wherein the target recognition sequence of the circularizable probe or probe set is a split recognition sequence comprising a first hybridization region having a first ligatable end and a second hybridization region having a second ligatable end,
   wherein the first hybridization region hybridizes to a 5' portion of the target sequence, and the second hybridization region hybridizes to a 3' portion of the target sequence, and the method comprises ligating the first ligatable end to the second ligatable end to generate the circularized probe.

7. The method of claim 1, wherein the RNase H comprises an RNase H1 and/or an RNase H2.

8. The method of claim 1, wherein contacting the biological sample with the RNase H comprises contacting the biological sample with between 0.5 enzyme units (U) and 50 U of the RNase H.

9. The method of claim 1, wherein the method comprises imaging the biological sample to detect the RCP.

10. The method of claim 9, wherein the imaging comprises detecting a signal associated with a fluorescently labeled probe that directly or indirectly binds to the RCP.

11. The method of claim 10, wherein a sequence of the RCP is analyzed by sequential hybridization, sequencing by hybridization, sequencing by ligation, sequencing by synthesis, sequencing by binding, or a combination thereof.

12. The method of claim 1, wherein the oligonucleotide hybridization region and the 3' portion of the target sequence overlap by about 6 to about 10 nucleotides.

13. The method of claim 1, wherein the method comprises contacting the biological sample with a polymerase in a first reaction mixture comprising a non-catalytic metal of the polymerase, and then contacting the biological sample with a second reaction mixture comprising a catalytic cofactor of the polymerase to perform the rolling circle amplification.

14. The method of claim 13, wherein the non-catalytic metal of the polymerase is barium, strontium, iron, cobalt, nickel, tin, zinc, or europium.

15. The method of claim 13, wherein the non-catalytic cofactor of the polymerase is calcium or strontium.

16. The method of claim 13, wherein the non-catalytic cofactor of the polymerase is strontium.

17. The method of claim 1, wherein a sequence of the RCP is analyzed at a location in the biological sample or a matrix embedding the biological sample.

18. The method of claim 1, comprising reacting at least one RNA in the biological sample with a polynucleotide kinase (PNK).

19. The method of claim 18, wherein the method comprises reacting at least one RNA in the biological sample with the PNK after contacting the biological sample with the nucleic acid oligonucleotide and the RNase H.

20. The method of claim 19, wherein the PNK is a T4 Polynucleotide Kinase (T4 PNK) or a T7 Polynucleotide Kinase (T7-PNK).

21. The method of claim 1, wherein the nucleic acid oligonucleotide is 20 to 35 nucleotides in length.

22. A method of analyzing a biological sample, comprising:
a) contacting the biological sample with a plurality of nucleic acid oligonucleotides, wherein a first oligonucleotide of the plurality hybridizes to a first oligonucleotide hybridization region in a first target ribonucleic acid (RNA) in the biological sample, and a second oligonucleotide of the plurality hybridizes to a second oligonucleotide hybridization region in a second target RNA in the biological sample;
b) cleaving the first and second target RNAs with an RNase H in their respective oligonucleotide hybridization regions to generate a first cleaved target RNA and a second cleaved target RNA;
c) contacting the biological sample with a plurality of circular probes or circularizable probes or probe sets, wherein a first circular probe or first circularizable probe or probe set of the plurality comprises a first target recognition sequence complementary to a first target sequence in the first target RNA,
wherein a second circular probe or second circularizable probe or probe set of the plurality comprises a second target recognition sequence complementary to a second target sequence in the second target RNA,
wherein the first and second circular probe or the first and second circularizable probe or probe set hybridize to their respective target RNAs,
wherein the first oligonucleotide hybridization region is overlapping with the 3' end of the first target sequence, and
wherein the second oligonucleotide hybridization region is overlapping with the 3' end of the second target sequence;
d) performing rolling circle amplification of the first and second circular probe or of a first and second circularized probe generated from the first and second circularizable probes or probe sets to generate a first and second rolling circle amplification product (RCP) using the first cleaved target RNA and the second cleaved target RNA as primers; and
e) detecting the first and second RCPs in the biological sample.

23. The method of claim 22, wherein the method comprises imaging the biological sample to detect the first and second RCPs.

24. The method of claim 22, wherein a sequence of the first and second RCPs is analyzed by sequential hybridization, sequencing by hybridization, sequencing by ligation, sequencing by synthesis, sequencing by binding, or a combination thereof.

25. The method of claim 22, wherein the first oligonucleotide hybridization region and the 3' portion of the first target RNA overlap by about 6 to about 10 nucleotides and the second oligonucleotide hybridization region and the 3' portion of the second target RNA overlap by about 6 to about 10 nucleotides.

26. The method of claim 22, wherein the first oligonucleotide and the second oligonucleotide are each 20 to 35 nucleotides in length.

27. The method of claim 22, wherein the method comprises contacting the biological sample with a polymerase in a first reaction mixture comprising a non-catalytic cofactor of the polymerase, and then contacting the biological sample with a second reaction mixture comprising a catalytic cofactor of the polymerase to perform the rolling circle amplification.

* * * * *